United States Patent
Singh et al.

(10) Patent No.: US 8,338,465 B2
(45) Date of Patent: Dec. 25, 2012

(54) CYCLIC CARBOXYLIC ACID RHODANINE DERIVATIVES FOR THE TREATMENT AND PREVENTION OF TUBERCULOSIS

(75) Inventors: Jasbir Singh, Naperville, IL (US); Carl F. Nathan, Larchmont, NY (US); Ruslana Bryk, New York, NY (US); Raghu Samy, Aurora, IL (US); Krzysztof Pupek, Plainfield, IL (US); Mark Gurney, Grand Rapids, MI (US)

(73) Assignee: Cornell Research Foundation, Inc., Ithaca, NY (US)

( * ) Notice: Subject to any disclaimer, the term of this patent is extended or adjusted under 35 U.S.C. 154(b) by 637 days.

(21) Appl. No.: 12/303,896

(22) PCT Filed: Jun. 8, 2007

(86) PCT No.: PCT/US2007/070707
§ 371 (c)(1),
(2), (4) Date: Sep. 2, 2009

(87) PCT Pub. No.: WO2008/005651
PCT Pub. Date: Jan. 10, 2008

(65) Prior Publication Data
US 2010/0210577 A1  Aug. 19, 2010

Related U.S. Application Data

(60) Provisional application No. 60/804,181, filed on Jun. 8, 2006, provisional application No. 60/804,185, filed on Jun. 8, 2006, provisional application No. 60/804,187, filed on Jun. 8, 2006.

(51) Int. Cl.
*A61K 31/425* (2006.01)
*C07D 277/00* (2006.01)
(52) U.S. Cl. ........................................ 514/369; 548/183
(58) Field of Classification Search .................. 514/369; 548/183
See application file for complete search history.

(56) References Cited

U.S. PATENT DOCUMENTS 7,799,782 B2 * 9/2010 Munson et al. ............ 514/234.5
2003/0190325 A1 * 10/2003 Nathan et al. ............. 424/190.1

FOREIGN PATENT DOCUMENTS

WO        2005/020990 A1    3/2005
WO   WO-2005/020990 A1 * 3/2005
WO        2005/041951 A3    5/2005

OTHER PUBLICATIONS

Nathan et al. CAS: 139:302015, 2003.*
International Preliminary Report on Patentability and Written Opinion for International Patent Application No. PCT/US2007/070707 (Dec. 24, 2008).
International Search Report for International Patent Application No. PCT/US2007/070707 (Jan. 30, 2008).

* cited by examiner

*Primary Examiner* — Rei-tsang Shiao
(74) *Attorney, Agent, or Firm* — LeClairRyan, a Professional Corporation

(57) ABSTRACT

Disclosed are methods for the prevention or treatment of tuberculosis in a subject infected with *Mycobacterium tuberculosis* by administering rhodanine derivatives of formula (I), as well as some novel such compounds. Other embodiments are also disclosed.

33 Claims, 9 Drawing Sheets

FIGURE 7

CYCLIC CARBOXYLIC ACID RHODANINE DERIVATIVES FOR THE TREATMENT AND PREVENTION OF TUBERCULOSIS

RELATED APPLICATIONS

This application is a national stage application under 35 U.S.C. §371 from PCT Application No. PCT/US2007/070707, filed 8 Jun. 2007, which claims the priority benefit of U.S. Provisional Application Nos. 60/804,181, 60/804,185 and 60/804,187 all filed 8 Jun. 2006.

This invention was made with government support under grant number HL72718 awarded by National Heart and Lung Institute and grant number UC1 A1062559 awarded by National Institutes of Health. The government has certain rights in this invention

FIELD OF THE INVENTION

The invention relates to a method and compositions for prevention and treatment of tuberculosis.

BACKGROUND OF THE INVENTION

Tuberculosis has reemerged as one of the leading causes of death, and *Mycobacterium tuberculosis* (Mtb) is the major etiologic agent of tuberculosis in humans. Another etiologic agent of tuberculosis in humans is *Mycobacterium bovis*. Also, a tuberculosis-like disease in humans may be caused by so-called atypical mycobacteria, such as but not limited to *Mycobacterium avium intracellulare*. The major cause of tuberculosis in ecomically important animals such as cattle is *Mycobacterium bovis*. *Mycobacterium tuberculosis* infects about one-third of the human population, persists for decades, and causes disease in a small fraction of those infected. Despite the low disease rate, *Mycobacterium tuberculosis* is the single leading cause of death of humans from bacterial infection and accounts for an extraordinary proportion of the chronic infectious morbidity and mortality of humankind. Resistance to each clinically approved anti-tuberculous drug is widespread among clinical isolates of *M. tuberculosis*. Thus, chemotherapy directed against new classes of targets is an urgent need.

It is known that *Mycobacterium tuberculosis* persists for prolonged periods in macrophages, that the host immune system responds to *Mycobacterium tuberculosis* with both oxidative and nitosative stress, and that *Mycobacterium tuberculosis* evades these insults. In *Mycobacterium tuberculosis*, dihydrolipoamide acyltransferase (DlaT; formerly termed succinyl transferase) is a component of the peroxynitrite reductase complex, and encodes one component of pyruvate dehydrogenase (PDH). DlaT has been shown to take part in protecting *Mycobacterium tuberculosis* from oxidative and nitrosative stress in macrophages. Mutant *M. tuberculosis* strains lacking DlaT are readily killed by mouse macrophages, and DlaT is necessary for full virulence of *M. tuberculosis* in mice [Shi and Ehrt, *Infection and Immunity* 74, 56-63 (2006)]. Compounds that inhibit DlaT or its expression are useful for the treatment of tuberculosis.

SUMMARY OF THE INVENTION

There is provided in accordance with some embodiments of the present invention a method of treating or preventing infection with *Mycobacterium tuberculosis* comprising administering to a subject a therapeutically or prophylactically effective amount of a compound of formula I:

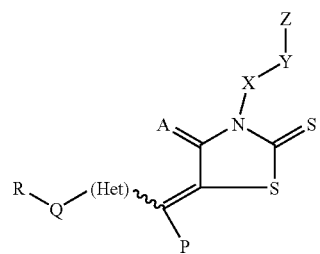

wherein:

A is chosen from oxygen and sulfur;

X is chosen from the group consisting of a direct bond, $(C_1-C_6)$alkylene in which one of the hydrogens is optionally replaced with a group —$(CH_2)_q$COOH wherein q is 0-6, —NH—, —NHSO$_2$—, and —NHC(=O)—;

Y is chosen from the group consisting of:
- $(C_1-C_{10})$alkylene,
- $(C_1-C_{10})$oxaalkylene,
- $(C_1-C_{10})$alkylene in which one or more hydrogens is replaced with $(C_1-C_6)$alkyl, substituted $(C_1-C_6)$alkyl, aryl, substituted aryl or heteroaryl,
- aryl,
- substituted aryl,
- heterocyclyl, and
- cycloalkyl;

Z is $(CH_2)_p$—$R^1$ where p is 0-6;

Q is chosen from the group consisting of a direct bond, -oxygen-, —CH$_2$—, —CH$_2$O—, —CH$_2$S—, —O—C(=O)—, —C(=O)O— and —C(=O)—NR$^{13}$—;

$R^1$ is chosen from the group consisting of —COOR$^3$, —OR$^4$, —P(=O)(OR$^5$)$_2$, —O—C(=O)NR$^6$R$^7$, —SO$_2$NR$^8$R$^9$, —CONR$^{10}$R$^{11}$, —OCH$_2$—COOR$^3$, —CO—$(C_1-C_6$alkyl), —CO—$(C_1-C_6$alkyl)-OH, and —CO—$(C_1-C_6$alkyl)COOH;

$R^3$ is chosen from the group consisting of H, $(C_1-C_{10})$alkyl, $(C_1-C_{10})$oxaalkyl, hydroxy$(C_1-C_{10})$alkyl, hydroxy$(C_1-C_{10})$oxaalkyl, $(C_1-C_{10})$azaalkyl, hydroxy$(C_1-C_{10})$azaalkyl and $(C_1-C_{10})$alkyl-OPO$_3$H;

$R^4$, $R^5$, $R^6$, $R^7$, $R^8$, and $R^{13}$ are chosen from H and $(C_1-C_6)$alkyl;

$R^9$ is chosen from the group consisting of H, $(C_1-C_6)$alkyl and —C(=O)R$^{12}$;

$R^{10}$ and $R^{11}$ are each independently chosen from the group consisting of H, $(C_1-C_6)$alkyl and $(C_1-C_6)$hydroxyalkyl;

$R^{12}$ is chosen from the group consisting of $(C_1-C_6)$alkyl, aryl and heteroaryl;

P is chosen from the group consisting of H, $(C_1-C_6)$alkyl, O$(C_1-C_6)$alkyl and F;

Het is a 5-membered or 6-membered heterocyclic ring; and

R is chosen from optionally substituted aryl and heterocyclyl; with the provisos that when —X—Y—Z is CH$_2$CH$_2$COOH, —HET-Q-R is not 5-(3-trifluoromethylphenyl)-furan-2-yl, and when —X—Y—Z is CH$_2$COOH, —HET-Q-R is not 5-(2,3-dichlorophenyl)-furan-2-yl.

In some embodiments, the method also includes administering a therapeutically effective amount of a compound of formula I, either simultaneously or sequentially, with at least one other therapeutic agent.

There is also provided, in accordance with embodiments of the present invention, a compound of the formula IA, viz. a compound of formula I, wherein either (a) when X is a direct bond, Y is phenyl, Z is —COOH and is located at the 3-position of the phenyl ring, P is H, HET is furan-2-yl, and -Q-R is at the 5-position of the furan ring, then -Q-R is 2-chlorophenyl, i.e. the compound is 3-[5[[5-(2-chlorophenyl)-2-furanyl]methylene]-4-oxo-2-thioxo-3-thiazolidinyl]benzoic acid (hereinafter "mycopyrin 5"), (b) when X is a direct bond, Y is phenyl, Z is COOR$^3$ or CONR$^{10}$R$^{11}$ wherein R$^3$ is ($C_1$-$C_{10}$)oxaalkyl, hydroxy($C_1$-$C_{10}$)oxaalkyl, hydroxy($C_1$-$C_{10}$)alkyl, ($C_1$-$C_{10}$)azaalkyl, hydroxy($C_1$-$C_{10}$)azaalkyl or ($C_1$-$C_{10}$)alkyl-OPO$_3$H, R$^{10}$ is H and R$^{11}$ is ($C_1$-$C_6$)hydroxyalkyl, A is oxygen, P is H, Het is furan-2-yl, and Q is a direct bond at the 5-position of the furan ring, then R is halogen-substituted phenyl, or (c) when X is a direct bond or ($C_1$-$C_6$)alkylene, Y is heterocyclyl or cycloalkyl.

Figure 1:
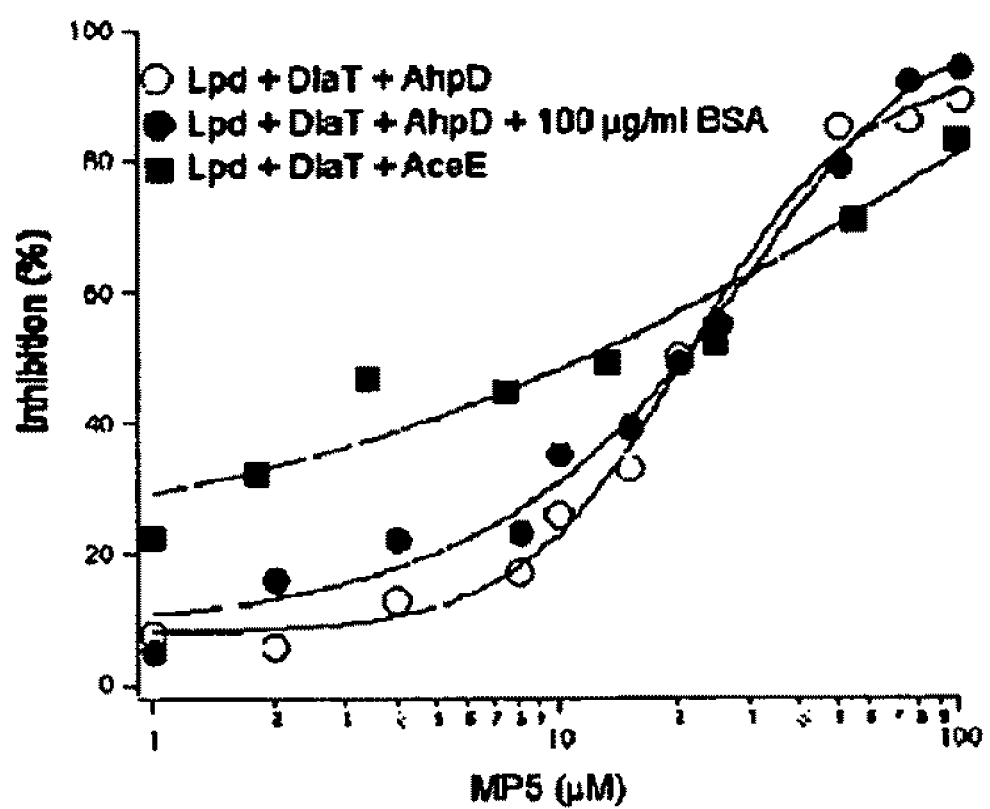
FIG. 1 is a graph showing the percent inhibition of dihydrolipoamide acyltransferase (DlaT) in the presence of lipoamide dehydrogenase (Lpd) and alkylhydroperoxide reductase subunit D (AhpD) or the E1 component of pyruvate dehydrogenase (AceE) as a function of concentration of mycopyrin 5 (identified as D155931)

In some embodiments, X in the compound of Formula I is a direct bond or $(C_1-C_3)$alkylene.

In some embodiments X in the compound of Formula I is a direct bond and Y is aryl or substituted aryl.

In some embodiments, X in the compound of Formula I is $(C_1-C_{10})$alkylene in which one or more hydrogens is replaced with aryl or heteroaryl.

In some embodiments Z in the compound of Formula I is chosen from —OR$^4$, —COOR$^3$, —SO$_2$NR$^8$R$^9$ and —CONR$^{10}$R$^{11}$, and R$^3$ is chosen from H and $(C_1-C_6)$alkyl.

In some embodiments P is H or CH$_3$.

In some embodiments Het in the compound of Formula I is furan, pyridine, thiazole, oxazole or benzofuran.

In some embodiments Q in the compound of Formula I is a direct bond, oxygen or CH$_2$.

In some embodiments R in the compound of Formula I is aryl or heterocyclyl.

In some embodiments, X in the compound of Formula I is a direct bond; Y is chosen from $(C_1-C_{10})$alkylene and $(C_1-C_{10})$alkylene in which one or more hydrogens is replaced with phenyl or substituted phenyl; and Z is —COOH.

In some embodiments, R$^1$ in the compound of Formula I is chosen from —COOR$^3$, —OR$^4$, —P(=O)(OR$^5$)$_2$, —O—C(=O)NR$^6$R$^7$, —SO$_2$NR$^8$R$^9$, and —CONR$^{10}$R$^{11}$, and R$^3$ is chosen from $(C_1-C_{10})$alkyl and $(C_1-C_{10})$oxaalkyl.

In some embodiments, R$^3$ in the compound of Formula I is chosen from H, $(C_1-C_{10})$alkyl and $(C_1-C_{10})$oxaalkyl.

In some embodiments, the compound of formula I has the structure:

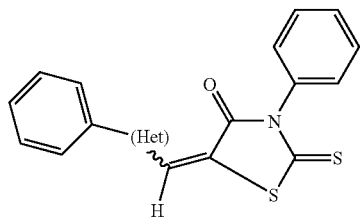

phenyl ring attached to Het is optionally substituted and the phenyl ring attached to the rhodanine ring is substituted with a group corresponding to Z and optionally father substituted.

In some embodiments, the compound of formula I has the structure:

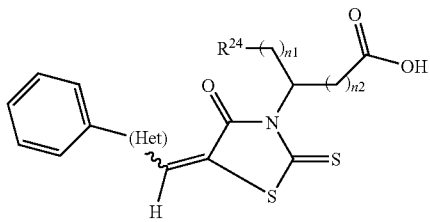

wherein n1 is 0 or 1, n2 is 0 to 4, R$^{24}$ is H, $(C_1-C_3)$alkyl or phenyl, and each of the phenyl rings is optionally substituted.

In some embodiments, the compound of formula I has the structure:

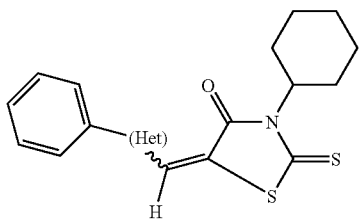

wherein the phenyl ring is optionally substituted and the cyclohexyl ring is substituted with a group corresponding to Z.

In some embodiments, the compound of formula I has the structure:

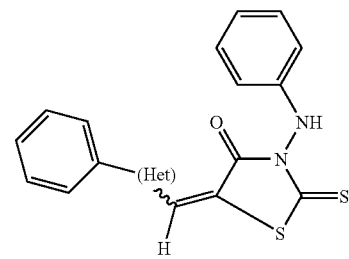

wherein the phenyl ring attached to Het is optionally substituted and the phenyl moiety of the aniline is substituted with a group corresponding to Z.

There are also provided, in accordance with embodiments of the invention, a compound formula IA, viz. of a compound of formula I, with the proviso that either (a) the compound is mycopyrin 5, (b) when X is a direct bond, Y is phenyl, Z is COOR$^3$ or CONR$^{10}$R$^{11}$ wherein R$^3$ is $(C_1-C_{10})$oxaalkyl, hydroxy$(C_1-C_{10})$oxaalkyl, hydroxy$(C_1-C_{10})$alkyl, $(C_1-C_{10})$azaalkyl, hydroxy$(C_1-C_{10})$azaalkyl or $(C_1-C_{10})$alkyl-OPO$_3$H, R$^{10}$ is H and R$^{11}$ is $(C_1-C_6)$hydroxyalkyl, A is oxygen, P is H, Het is furan-2-yl, and Q is a direct bond at the 5-position of the furan ring, then R is halogen-substituted phenyl, or (c) when X is a direct bond or $(C_1-C_6)$alkylene, Y is heterocyclyl or cycloalkyl.

In some embodiments, the compound of formula IA is a compound of formula IB, viz. a compound of formula I with the proviso that when X is a direct bond or $(C_1-C_6)$alkylene, Y is heterocyclyl or cycloalkyl.

In some embodiments, A in the compound of Formula IB is oxygen.

In some embodiments, X in the compound of formula IB is chosen from a direct bond, $(C_1-C_3)$alkylene and —NH—.

In some embodiments, Y in the compound of Formula IB is chosen from $(C_1-C_{10})$alkylene, $(C_1-C_{10})$oxaalkylene, $(C_1-C_{10})$alkylene in which one or more hydrogens is replaced with aryl or heteroaryl, aryl, substituted aryl, heterocyclyl and cycloalkyl.

In some embodiments, Y in the compound of Formula IB is aryl, substituted aryl, cycloalkyl or heterocyclyl.

In some embodiments, Z in the compound of formula IB is chosen from —OR$^4$, —COOR$^3$, —SO$_2$NR$^8$R$^9$ and —CONR$^{10}$R$^{11}$, and R$^3$ is chosen from H and $(C_1-C_6)$alkyl.

In some embodiments, P in the compound of formula IB is H or CH$_3$.

In some embodiments, Het in the compound of formula IB is furan, pyridine, thiazole, oxazole or benzofuran.

In some embodiments, Q in the compound of formula IB is a direct bond, oxygen or $CH_2$.

In some embodiments, X in the compound of formula IB is chosen from —NH—, —NHSO$_2$—, and —NHC(=O)—. In some embodiments, X is NH, Y is phenyl, and Z is COOH which is at the 2-position of the phenyl ring. In some embodiments, the compound of formula IB has the structure

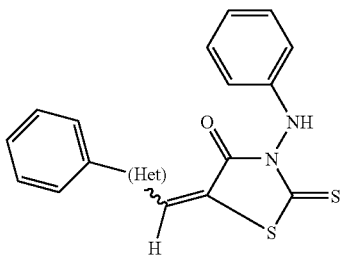

where the phenyl moiety of the aniline is substituted at the 2-position with COOH and the phenyl ring attached to Het is optionally substituted. In some embodiments Het is 2,5-furanyl.

In some embodiments, X in the compound of formula IB is a direct bond or ($C_1$-$C_3$)alkylene and Y is heterocyclyl or cycloalkyl. In some embodiments, X in the compound of formula IB is a direct bond and Y is cyclohexyl. In some embodiments, Z is COOH at the 3- or 4-position of the cyclohexyl ring. In some embodiments, the compound of formula IB has the structure:

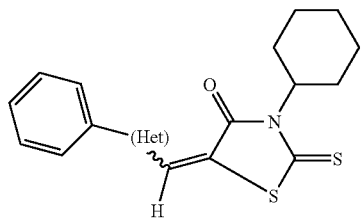

wherein the cyclohexyl ring is substituted at the 3- or 4-position with COOH and the phenyl ring is optionally substituted. In some embodiments, Het is 2,5-furanyl.

In some embodiments, $R^1$ in the compound of formula IB is chosen from —COOR$^3$, —P(=O)(OR$^5$)$_2$, —O—C(=O)NR$^6$R$^7$, —SO$_2$NR$^8$R$^9$, —CONR$^{10}$R$^{11}$, and $R^3$ is chosen from ($C_1$-$C_{10}$)alkyl and ($C_1$-$C_{10}$)oxaalkyl.

In some embodiments, the compound of formula IA is mycopyrin 5

There are also provided, in accordance with embodiments of the invention, pharmaceutical formulations comprising: (a) a pharmaceutically acceptable carrier; and (b) a therapeutically effective amount of a compound of formula IA. In some embodiments, the compound of formula IA is mycopyrin 5. In some embodiments, the compound of formula IA is a compound of formula IB. In some embodiments, the formulations additionally include (c) a therapeutically effective amount of a second agent having established or presumptive activity in the prevention or treatment of tuberculosis. In some embodiments, the formulation is in the form of a tablet, capsule or aerosol.

DEFINITIONS

Throughout this specification, the terms and substituents retain their definitions.

As used herein, and as would be understood by the person of skill in the art, the recitation of "a compound" is intended to include salts, solvates and inclusion complexes of that compound. Thus, for example, a claim to 3-[5[[5-(2-chlorophenyl)-2-furanyl]methylene]-4-oxo-2-thioxo-3-thiazolidinyl]benzoic acid is intended to encompass as well sodium 3-[5[[5-(2-chlorophenyl)-2-furanyl]methylene]-4-oxo-2-thioxo-3-thiazolidinyl]benzoate, whether or not expressly stated in the claim.

"Alkyl", as used above, refers to saturated hydrocarbon residues containing eight or fewer carbons in straight or branched chains, as well as cyclic structures. Examples of such radicals include methyl, ethyl, n-propyl, isopropyl, n-butyl, isobutyl, sec-butyl, tert-butyl, pentyl, iso-amyl, hexyl, octyl and the like. Cycloalkyl is a subset of alkyl and includes cyclic hydrocarbon groups of from 3 to 10 carbon atoms. Examples of cycloalkyl groups include c-propyl, c-butyl, c-pentyl, norbornyl and the like.

"Alkoxy" refers to the same residues, containing, in addition, an oxygen atom at the point of attachment.

Alkylene, as would be understood by the person of skill in the art, refers to divalent alkyl radicals. Alkylene may refer to divalent straight or branched chains. Many examples of both occur in the tables. Thus, for example, the compounds in Table 3

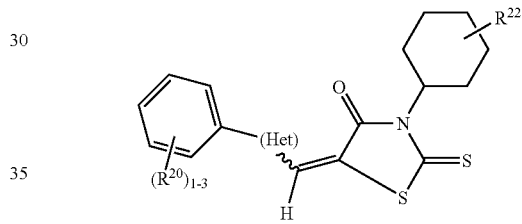

are compounds having an alkylene group (cyclohexyl) attached at one point to the rhodanine ring and at another point to $R^{22}$, and the compounds in Table 7

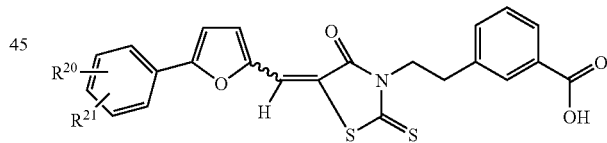

are compounds having an alkylene group (ethyl) attached at one point to the rhodanine ring and at another point to 3-COOH-phenyl.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

"Aryl" and "heteroaryl" mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. "Aryl" includes phenyl, substituted phenyl, naphthyl and the like. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Heterocycle" means a cycloalkyl or aryl residue in which from one to three carbons is replaced by a heteroatom selected from the group consisting of N, O and S. The heterocycle may be fused to an aromatic hydrocarbon radical. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The representation of the configuration of the carbon-carbon double bond adjacent the thiazolidine ring is selected for convenience only and is not intended to designate a particular configuration. It will be appreciated that the absolute E/Z stereochemistry at this position has not yet been determined for every compound disclosed herein, but that the NMR data for all compounds thus far examined indicates that with respect to this position, generally each compound is a single enantiomer, either E or Z. Thus the double bond depicted arbitrarily herein as E may be Z, E, whichever of these isomers is active in the assays described herein, or a mixture of the two isomers in any proportion, if the mixture is active. Likewise, all tautomeric forms are also intended to be included, to the extent that they are active.

The term tuberculosis means an infectious disease of humans or animals caused by any mycobacterium other than *Mycobacterium leprae*, including but not limited to *Myobacterium tuberculosis, Mycobacterium bovis*, and the so-called atypical mycobacteria, such as but not limited to *Mycobacterium avium intracellulare*.

The terms "methods of treating or preventing" mean amelioration, prevention or relief from the symptoms and/or effects associated with tuberculosis. The term "preventing" as used herein refers to administering a medicament beforehand to forestall or obtund an acute episode or, in the case of a chronic condition to diminish the likelihood or seriousness of the condition. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis.

"Subject" includes living organisms such as humans, monkeys, cows, sheep, horses, pigs, cattle, goats, dogs, cats, mice, rats, cultured cells, and transgenic species thereof. In a preferred embodiment, the subject is a human.

Administering the compositions containing a compound of formula I to a subject to be treated can be carried out using known procedures, at dosages and for periods of time effective to treat the condition in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation. Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X—Y—X, X—X—Y, Y—X—Y, Y—Y—X, X—X—Y—Y, etc.

"Administering" a compound of Formula I includes administering prodrug forms (e.g. esters and amides) so as to provide effective levels of the compound in the subject. The term "prodrug" refers to a compound that is made more active in vivo. Activation in vivo may come about by chemical action or through the intermediacy of enzymes. Microflora in the GI tract may also contribute to activation in vivo. Common esters employed as prodrugs are methyl, ethyl and oxaalkyl esters. For example, under appropriate circumstances the following esters and amides may function as prodrugs for their corresponding carboxylic acids: —NHCH$(CH_2OH)_2$, —OCH$_2$CH(CH$_2$OH)$_2$, —NHC(CH$_2$OH)$_3$, —OCH$_2$C(CH$_3$)(CH$_2$OH)$_2$, —OCH$_2$CH$_2$N(CH$_2$CH$_2$OH)$_2$, —(CH$_2$)$_4$OPO$_3$H, —O(CH$_2$)$_3$OH, —O(CH$_2$)$_4$OH.

The following abbreviations and terms have the indicated meanings throughout:

Ac=acetyl
AceE=the E1 component of pyruvate dehydrogenase
ADN=a mixture of 0.5 bovine serum albumin, 0.2% dextrose and 0.085% sodium chloride
AhpD=alkylhydroperoxide reductase subunit D
BCG=*Mycobacterium bovis* var. Bacille Calmette Guerin
BNB=4-bromomethyl-3-nitrobenzoic acid
Boc=t-butyloxy carbonyl
Bu=butyl
c-=cyclo
CoA=coenzyme A, a cosubstrate for E2
DBU=diazabicyclo[5.4.0]undec-7-ene
DCM=dichloromethane=methylene chloride=CH$_2$Cl$_2$
DEAD=diethyl azodicarboxylate
DEADA=diethylenediamine diacetate
DIC=diisopropylcarbodiimide
DIEA=N,N-diisopropylethyl amine
DlaT=dihydrolipoamide acyltransferase, the E2 component of PDH
DMAP=4-N,N-dimethylaminopyridine
DME=1,2-dimethoxyethane
DMF=N,N-dimethylformamide
DMSO=dimethyl sulfoxide
DTNB=5,5'-dithiobis-2-nitrobenzoic acid
DVB=1,4-divinylbenzene
EEDQ=2-ethoxy-1-ethoxycarbonyl-1,2-dihydro quinoline
Et=ethyl
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Lpd=lipoamide dehydrogenase, the E3 component of PDH
Me=methyl
mesyl=methanesulfonyl
Mtb=*Mycobacterium tuberculosis*
MTBE=methyl t-butyl ether
Mycopyrin 5=3-[-[[5-(2-chlorophenyl)-2-furanyl]methylene]-4-oxo-2-thioxo-3-thiazolidinyl]benzoic acid
NAD=nicotinamide adenine dinucleotide
NADH=reduced form of NAD
NMO=N-methylmorpholine oxide
OADC=Middlebrook enrichment (a mixture of olecic acid, albumin, dextrose and catalase)
OD=optical density
PBS=phosphate buffered solution
PDH=pyruvate dehydrogenase
PEG=polyethylene glycol
Ph or κ=phenyl
PhOH=phenol
PfP=pentafluorophenol
PPTS=pyridinium p-toluenesulfonate
PyBroP=bromo-tris-pyrrolidino-phosphonium hexafluorophosphate
RNI=reactive nitrogen intermediates
rt=room temperature
sat'd=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl
Tween-80=Polyethylene glycol sorbitan monooleate A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

A variety of routes of administration are possible including, but not necessarily limited to parenteral (e.g., intravenous, intra-arterial, intramuscular, subcutaneous injection), oral (e.g., dietary or by inhalation), topical, nasal, rectal, or via slow releasing micro-carriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvant and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. (See generally, Remington's Pharmaceutical Science, 16th Edition, Mack, Ed. (1980)).

An appropriate composition comprising the compound to be administered can be prepared in a physiologically acceptable vehicle or carrier and optional adjuvant and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See generally, Remington's Pharmaceutical Science, 16th Edition, Mack, Ed. (1980)).

"Effective amount" includes the amount of the compound or a pharmaceutically acceptable salt, hydrate or ester thereof which allows it to perform its intended function, i.e., prevention of onset or treatment of tuberculosis. A therapeutically effective amount of the active substance can be administered by an appropriate route in a single dose or multiple doses. Further, the dosages of the active substance can be proportionally increased or decreased as indicated by the exigencies of the therapeutic or prophylactic situation. The effective amount will depend upon a number of factors, including biological activity, age, body weight, sex, general health, severity of the condition to be treated, as well as appropriate pharmacokinetic properties.

Compounds of Formula I or pharmaceutically acceptable salts, hydrates or esters thereof can be used in a method for preventing or treating tuberculosis. The compounds can be administered via any medically acceptable means including oral, rectal, topical or parenteral (including subcutaneous, intramuscular and intravenous) administration.

The term "pharmaceutically acceptable salt" refers to salts whose counter ion derives from pharmaceutically acceptable non-toxic acids and bases. When the compounds contain an acidic residue, suitable pharmaceutically acceptable base addition salts for the compounds of the present invention include ammonium, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Other base addition salts includes those made from: arecoline, arginine, barium, benethamine, benzathine, betaine, bismuth, clemizole, copper, deanol, diethylamine, diethylaminoethanol, epolamine, ethylenediamine, ferric, ferrous, glucamine, glucosamine, histidine, hydrabamine, imidazole, isopropylamine, manganic, manganous, methylglucamine, morpholine, morpholineethanol, n-ethylmorpholine, n-ethylpiperidine, piperazine, piperidine, polyamine resins, purines, theobromine, triethylamine, trimethylamine, tripropylamine, trolamine, and tromethamine. When the compounds contain a basic residue, suitable pharmaceutically acceptable base addition salts for the compounds of the present invention include inorganic acids and organic acids. Examples include acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate, and the like.

The compounds of formula I are preferably administered with an acceptable carrier for the mode of administration. "Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Any formulation or drug delivery system containing the active ingredient, which is suitable for the intended use, as are generally known to those of skill in the art, can be used. Compounds of Formula I may be administered orally or via injection at a dose from 0.01 to 25 mg/kg per day. Oral administration can be such as to result in the formulation being ingested or in the formulation being inhaled. The dose range for adult humans is generally from 0.5 mg to 1 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterile aqueous preparation of the active compound, which is preferably isotonic with the blood of the recipient. Thus, such formulations may conveniently contain distilled water, 5% dextrose in distilled water or saline. Useful formulations also include concentrated solutions or solids containing Compound I, which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A tablet, capsule, cachet, lozenge, suspension, aerosol or other enteral formulation may be made in which a compound of formula I is combined with one or more other active ingredients, the additional active ingredient or ingredients being a compound or compounds with known or presumptive efficacy at preventing or treating tuberculosis in a person or animal infected with *Mycobacterium tuberculosis*. "Presumptive efficacy" means efficacy that is expected based on evidence in experimental systems other than clinical trials and that remains to be tested in clinical trials.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposome or microspheres (or microparticles). Methods for preparing liposome and microspheres for administration to a patient are well known to those of skill in the art. U.S. Pat. No.

4,789,734, the contents of which are hereby incorporated by reference, describes methods for encapsulating biological materials in liposome. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposome," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference. Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

The formulations may conveniently be presented in unit dosage form and may be prepared by any of the methods well known in the art of pharmacy. All methods include the step of bringing the active compound into association with a carrier, which constitutes one or more accessory ingredients. In general, the formulations are prepared by uniformly and intimately bringing the active compound into association with a liquid carrier or a finely divided solid carrier and then, if necessary, shaping the product into desired unit dosage form.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Compounds of formula I can be used can be used advantageously in combination with other agents that have established or presumptive activity in the prevention or treatment of tuberculosis, such as rifampin and its variants, isoniazid, pyrazinamide, ethambutol and its variants, streptomycin, cycloserine, PA-824, and fluoroquinolines, including but not limited to moxafloxacin.

EXAMPLES

Embodiments of the invention will be further illustrated in the following non-limiting examples.

The synthesis of many compounds of formula I listed in the Tables below are described in U.S. Patent Application Publication No. 2004/0198741, the contents of which are incorporated herein by reference. The novel compounds of formula IA listed in the Tables below may be synthesized as described herein.

General Procedure for the Synthesis of Phenyl-Furan-Carbaldehydes:

The phenyl-furan-carbaldehydes shown below were synthesized using either procedure A or procedure B as described below.

Procedure A:

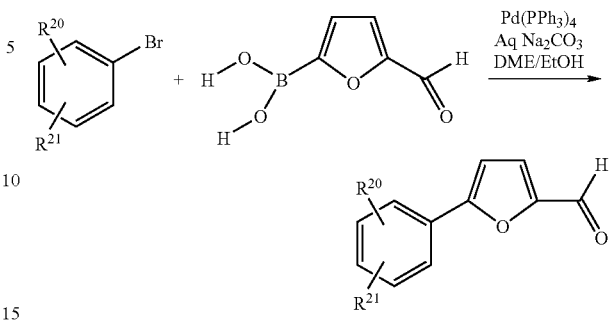

To a round bottom flask containing appropriately substituted-bromo-benzene (7 mmol) and 5-formyl-2-furan-boronic acid (10.6 mmol) in 1,2-dimethoxyethane (80 mL) and ethanol (20 mL) was added an aqueous solution of sodium carbonate (21 mmol) in water (30 mL). The reaction mixture was stirred at room temperature for 5 minutes, followed by the addition of tetrakis(triphenylphosphine)palladium (0.35 mmol). The reaction mixture was heated at 70° C. until completion of reaction was determined by thin-layer chromatography (TLC). The reaction mixture was cooled to room temperature and diluted with ethyl acetate (500 mL) and water (50 mL). The layers were separated and the aqueous layer was extracted with ethyl acetate (2×150 mL). The combined organic extracts were washed with brine, dried (sodium sulfate) and concentrated under vacuum. The crude product was purified by silica gel chromatography to afford 5-(appropriately substituted)-furan-2-carbaldehyde.

Procedure B:

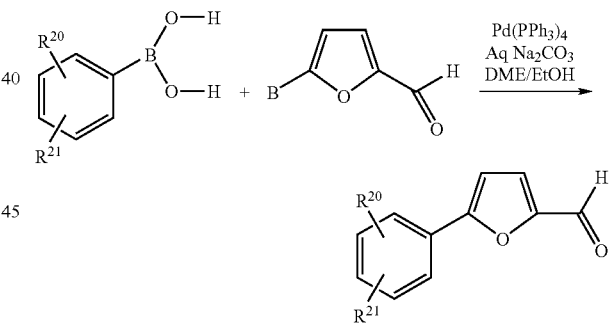

To a round bottom flask containing 5-bromo-furan-2-carbaldehyde (3 mmol) and appropriately substituted-phenylboronic acid (3.6 mmol) in dimethoxyethane (40 mL) was added an aqueous solution of sodium carbonate (9 mmol) in water (10 mL). The reaction mixture was stirred at room temperature for 5 minutes, followed by the addition of tetrakis(triphenylphosphine)palladium (0.15 mmol). The reaction mixture was heated at 85° C. until completion of the reaction as determined by TLC. The reaction mixture was cooled to room temperature and diluted with ethyl acetate (200 mL) and water (50 mL). The layers were separated and the aqueous layer was extracted with ethyl acetate (2×100 mL). The combined organic extracts were washed with brine, dried (sodium sulfate) and concentrated under vacuum. The crude product was purified by silica gel chromatography to afford 5-(appropriately substituted)-furan-2-carbaldehyde.

TABLE A

Aldehydes (Compounds ALD1 to ALD79)

| Compound | $R^{20} + R^{21}$ | Source |
|---|---|---|
| ALD1 | 2-Cl | Commercial |
| ALD2 | 3-Cl | Commercial |
| ALD3 | 4-Cl | Commercial |
| ALD4 | 2,4-di-Cl | Commercial |
| ALD5 | 2,5-di-Cl | Commercial |
| ALD6 | 2,6-di-Cl | Commercial |
| ALD7 | 3,4-di-Cl | Commercial |
| ALD8 | 3-Cl-4-OCH$_3$ | Commercial |
| ALD9 | 2-CF$_3$ | Commercial |
| ALD10 | 3-CF$_3$ | Commercial |
| ALD11 | 2-Cl-5-CF$_3$ | Commercial |
| ALD12 | 2-OCF$_3$ | Commercial |
| ALD13 | 3-OH-4-COOH | Commercial |
| ALD14 | 2-COOH | Commercial |
| ALD15 | 3-NO$_2$ | Commercial |
| ALD16 | 2-NO$_2$ | Commercial |
| ALD17 | 4-NO$_2$ | Commercial |
| ALD18 | 2-NO$_2$-4-Cl | Commercial |
| ALD19 | 3-F-4-OCH$_3$ | Commercial |
| ALD20 | 4-CH$_2$Ph | Procedure A |
| ALD21 | 4-OPh | Procedure B |
| ALD22 | 4-cyclohexyl | Procedure A |
| ALD23 | 4-C(CH$_3$)$_3$ | Procedure A |
| ALD24 | 4-CH(CH$_3$)$_2$ | Procedure A |
| ALD25 | 3-CH(CH$_3$)$_2$ | Procedure A |
| ALD26 | 4-COPh | Procedure A |
| ALD27 | 4-CH$_2$SPh | Procedure A |
| ALD28 | 4-CH$_2$CH(CH$_3$)$_2$ | Procedure A |
| ALD29 | 4-cyclopentyl | Procedure A |
| ALD30 | 4-C(CH$_3$)$_2$Ph | Procedure A |
| ALD31 | 2-Cl-4-OH | Procedure A |
| ALD32 | 4-N(CH$_3$)2 | Procedure A |
| ALD33 | 4-CH$_2$N(CH$_3$)2 | Procedure A |
| ALD34 | 3-N(CH$_3$)2 | Procedure A |
| ALD35 | 2-OH-5-C(CH$_3$)3 | Procedure A |
| ALD36 | 4-morpholine | Procedure A |
| ALD37 | 2-CH$_3$ | Procedure B |
| ALD38 | 2-OCH$_3$ | Procedure B |
| ALD39 | 2-F | Procedure B |
| ALD40 | 2-CN-3-F | Procedure A |
| ALD41 | 2-CH$_3$-4-F | Procedure B |
| ALD42 | 2-F-4-CH$_3$ | Procedure B |
| ALD43 | 2,4-di-F | Procedure B |
| ALD44 | 2,4-di-CH$_3$ | Procedure B |
| ALD45 | 4-CH$_3$ | Procedure B |
| ALD46 | 4-OCH$_3$ | Procedure B |
| ALD47 | 2-SCH$_3$ | Procedure B |
| ALD48 | 3-SCH$_3$ | Procedure B |
| ALD49 | 4-SCH$_3$ | Procedure B |
| ALD50 | 2-NHCOOC(CH$_3$)$_3$ | Procedure A |
| ALD51 | 4-OCH$_3$-2-CH$_3$ | Procedure B |
| ALD52 | 2-OH | Procedure B |
| ALD53 | 2,4-di-OCH$_3$ | Procedure B |
| ALD54 | 2,6-di-CH$_3$ | Procedure B |
| ALD55 | 2-OCH$_2$Ph | Procedure B |
| ALD56 | 4-N(CH$_3$)$_2$-2-CH$_3$ | Procedure A |
| ALD57 | 2,4,6-tri-CH$_3$ | Procedure B |
| ALD58 | 4-CH$_2$CH$_3$ | Procedure B |
| ALD59 | 4-CF$_3$ | Procedure B |
| ALD60 | 4-F | Procedure B |
| ALD61 | 4-OCH$_2$CH$_3$ | Procedure B |
| ALD62 | 4-(CH$_2$)$_2$CH$_3$ | Procedure B |
| ALD63 | 4-(CH$_2$)$_3$CH$_3$ | Procedure B |
| ALD64 | 4-NHCOCH$_3$ | Procedure B |
| ALD65 | 4-SO$_2$CH$_3$ | Procedure B |
| ALD66 | 4-COCH$_3$ | Procedure B |
| ALD67 | 3-CH$_2$OH | Procedure B |
| ALD68 | 4-OCH(CH$_3$)$_2$ | Procedure B |
| ALD69 | 2-CH$_2$CH$_3$ | Procedure A |
| ALD70 | 2-Ph | Procedure B |
| ALD71 | 3-Ph | Procedure B |
| ALD72 | 2-OCH$_3$-5-CH$_3$ | Procedure B |
| ALD73 | 2-OPh | Procedure B |
| ALD74 | 4-SO$_2$NH$_2$ | Procedure A |
| ALD75 | 4-SO$_2$NHCH$_3$ | Procedure A |
| ALD76 | 4-Cl-2-CH$_3$ | Procedure B |
| ALD77 | 4-F-2-OCH$_3$ | Procedure B |
| ALD78 | 3,5-di-Cl | Procedure A |
| ALD79 | 2,3-di-Cl | Procedure A |

Data for representative aldehydes is listed below:

ALD 1-ALD 19: Purchased from commercial vendors.

ALD 20: 5-(4-benzyl-phenyl)-furan-2-carbaldehyde: $^1$H NMR (400 MHz, DMSO-d$_6$): δ 3.99 (2H, s), 7.20-7.39 (8H, m), 7.63 (1H, d, J=3.6 Hz), 7.78-7.81 (2H, m), 9.59 (1H, s); APCI-MS: 262.02.

ALD 21: 5-(4-phenoxy-phenyl)-furan-2-carbaldehyde: $^1$H NMR (400 MHz, DMSO-d$_6$): δ 7.07-7.13 (5H, m), 7.17-7.21 (1H, m), 7.40-7.44 (2H, m), 7.56 (1H, m), 7.85 (2H, m), 9.60 (1H, s); APCI-MS: 264.9.

ALD 22: 5-(4-cyclohexyl-phenyl)-furan-2-carbaldehyde: $^1$H NMR (400 MHz, CDCl$_3$): δ 1.28-1.46 (5H, m), 1.75-1.87 (5H, m), 2.53-2.54 (1H, m), 6.79 (1H, d, J=3.6 Hz), 7.26-7.32 (3H, m), 7.73-7.76 (2H, m), 9.63 (1H, s).

ALD 23: 5-(4-tert-butyl-phenyl)-furan-2-carbaldehyde: $^1$H NMR (400 MHz, CDCl$_3$): δ 1.35 (9H, s), 6.80 (1H, d, J=3.6 Hz), 7.31 (1H, d, J=3.6 Hz), 7.44-7.7.48 (2H, m), 7.74-7.77 (2H, m), 9.64 (1H, s); APCI-MS: 228.34.

ALD 28: 5-(4-isobutyl-phenyl)-furan-2-carbaldehyde: $^1$H NMR (400 MHz, CDCl$_3$): δ 0.92 (6H, d, J=6.4 Hz), 1.90 (1H, m), 2.51 (2H, d, J=7.2 Hz), 6.80 (1H, d, J=3.6 Hz), 7.20 (2H, m), 7.31 (1H, dd, J=3.6, 1.2 Hz), 7.74 (2H, m), 9.63 (1H, s). ESI-MS: 227.1.

ALD 31: 5-(2-chloro-4-hydroxy-phenyl)-furan-2-carbaldehyde: $^1$H NMR (400 MHz, DMSO-d$_6$): δ 6.93 (1H, dd, J=2.4 & 8.8 Hz), 6.99 (1H, d, J=2.4 Hz), 7.18 (1H, d, J=3.6 Hz), 7.64 (1H, d, J=4 Hz), 7.76 (1H, d, J=8.8 Hz), 9.62 (1H, s), 10.5 (1H, s).

ALD 32: 5-(4-dimethylamino-phenyl)-furan-2-carbaldehyde: $^1$H NMR (400 MHz, CDCl$_3$): δ 3.03 (6H, s), 6.62 (1H, d, J=3.6 Hz), 6.72 (2H, m), 7.29 (1H, d, J=3.6 Hz), 7.70 (2H, m), 9.56 (1H, s). MS-ESI−: 216.4.

ALD 34: 5-(3-dimethylamino-phenyl)-furan-2-carbalde-hyde: $^1$H NMR (400 MHz, CDCl$_3$): δ 3.03 (6H, s), 6.77 (1H, m), 6.82 (1H, d, J=3.6 Hz), 7.16 (2H, bs), 7.32 92H, m), 9.64 (1H, s).

ALD 35: 5-(5-tert-butyl-2-hydroxy-phenyl)-furan-2-car-baldehyde: $^1$H NMR (400 MHz, CDCl$_3$): δ 1.33 (9H, s) 6.51 (1H, bs), 6.90 (1H, d, J=8.8 Hz), 7.03 (1H, d, J=4.0 Hz), 7.32 (1H, dd, J=8.8, 2.4 Hz), 7.36 (1H, d, J=3.6 Hz), 7.73 (1H, d, J=3.2 Hz), 9.64 (1H, s). ESI-MS: 243.0.

ALD 36: 5-(4-morpholin-4-yl-phenyl)-furan-2-carbalde-hyde: $^1$H NMR (400 MHz, CDCl$_3$): δ 3.26 (2H, dd, J=5.2, 3.6 Hz), 3.87 (2H, dd, J=5.2, 3.6 Hz), 6.69 (1H, d, J=4.0 Hz), 6.93 (2H, m), 7.26 (1H, s), 7.30 (1H, d, J=4.0), 7.74 (2H, m), 9.58 (1H, s). ESI-MS: 258.0.

ALD 37: 5-(2-methyl-phenyl)-furan-2-carbaldehyde: NMR (500 MHz, CDCl$_3$): δ 2.56 (3H, s), 6.75 (1H, d, J=3.5 Hz), 7.29-7.35 (3H, m), 7.80 (1H, m), 9.68 (1H, s).

ALD 38: 5-(2-methoxy-phenyl)-furan-2-carbaldehyde: $^1$H NMR (400 MHz, CDCl$_3$): δ 3.97 (3H, s), 6.98 (1H, d, J=8 Hz), 7.07 (1H, m), 7.14 (1H, d, J=3.6 Hz), 7.32-7.39 (2H, m), 8.05 (1H, m), 9.65 (1H, s).

ALD 39: 5-(2-fluoro-phenyl)-furan-2-carbaldehyde: $^1$H NMR (400 MHz, CDCl$_3$): δ 7.04 (1H, t, J=4 Hz), 7.14-7.19 (1H, m), 7.28 (1H, m), 7.36-7.41 (2H, m), 8.03 (1H, m), 9.69 (1H, s).

ALD 41: 5-(2-methyl-4-fluoro-phenyl)-furan-2-carbaldehyde: $^1$H NMR (400 MHz, CDCl$_3$): δ 2.54 (3H, s), 6.70 (1H, d, J=3.6 Hz), 6.98-7.01 (2H, m), 7.34 (1H, d, J=3.6 Hz), 7.75-7.79 (1H, m), 9.67 (1H, s). MS-ESI+: 205.2.

ALD 42: 5-(2-fluoro-4-methyl-phenyl)-furan-2-carbaldehyde: $^1$H NMR (400 MHz, CDCl$_3$): δ 2.40 (3H, s), 6.96-7.00 (2H, m), 7.05-7.07 (1H, m), 7.35 (1H, m), 7.89 (1H, m), 9.66 (1H, s). MS-ESI+: 205.0.

ALD 43: 5-(2,4-difluoro-phenyl)-furan-2-carbaldehyde: $^1$H NMR (500 MHz, CDCl$_3$): δ 6.92-7.03 (3H, m), 7.35 (1H, d, J=4 Hz), 7.99-8.04 (1H, m), 9.68 (1H, s). MS-ESI+: 209.1

ALD 44: 5-(2,4-dimethyl-phenyl)-furan-2-carbaldehyde: $^1$H NMR (500 MHz, CDCl$_3$): δ 2.36 (3H, s), 2.52 (3H, s), 6.70 (1H, d, J=4 Hz), 7.11 (2H, m), 7.34 (1H, d, J=4 Hz), 7.71 (1H, d, J=8 Hz), 9.65 (1H, s). MS-ESI+: 201.0.

ALD 45: 5-(4-methyl-phenyl)-furan-2-carbaldehyde: $^1$H NMR (400 MHz, CDCl$_3$): δ 2.40 (3H, s), 6.79 (1H, d, J=3.6 Hz), 7.25-7.27 (2H, m), 7.31 (1H, d, J=3.6 Hz), 7.71-7.73 (2H, m), 9.63 (1H, s).

ALD 46: 5-(4-methoxy-phenyl)-furan-2-carbaldehyde: $^1$H NMR (400 MHz, CDCl$_3$): δ 3.86 (3H, s), 6.71 (1H, d, J=4.0 Hz), 6.96-6.98 (2H, m), 7.31 (1H, d, J=4.0 Hz), 7.76-7.78 (2H, m), 9.60 (1H, s).

ALD 47: 5-(2-methylsulfanyl-phenyl)-furan-2-carbaldehyde: $^1$H NMR (400 MHz, CDCl$_3$): δ 2.53 (3H, s), 7.18 (1H, d, J=3.6 Hz), 7.23-7.27 (1H, m), 7.32-7.40 (4H, m), 7.87 (1H, dd, J=8.0 Hz, J=1.6 Hz), 9.68 (1H, s). APCI-Mass: 219.0.

ALD 50: [2-(5-formyl-furan-2-yl)-phenyl]-carbamic acid tert-butyl ester: $^1$H NMR (400 MHz, CDCl$_3$): δ 1.53 (9H, s), 6.82 (1H, d, J=3.6 Hz), 7.13 (1H, m), 7.36 (1H, d, J=3.6 Hz), 7.41 91H, m), 7.63 (1H, m), 7.67 (1H, bs), 8.13 (1H, d, J=8.4 Hz), 9.69 (1H, s).

ALD 51: 5-(4-methoxy-2-methyl-phenyl)-furan-2-carbaldehyde: $^1$H NMR (400 MHz, CDCl$_3$): δ 2.53 (3H, s), 3.85 (3H, s), 6.65 (1H, d, J=4 Hz), 6.81 (2H, m), 7.33 (1H, d, J=4 Hz), 7.76 (1H, d, J=8.4 Hz), 9.63 (1H, s). MS-ESI+: 217.4.

ALD 52: 5-(2-hydroxy-phenyl)-furan-2-carbaldehyde: $^1$H NMR (400 MHz, CDCl$_3$): δ 6.56 (1H, bs), 6.94-7.03 (2H, m), 7.28-7.32 (2H, m), 7.36 (1H, d, J=4 Hz), 7.76 (1H, dd, J=1.6 & 8 Hz), 9.64 (1H, s). MS-ESI+: 189.0.

ALD 53: 5-(2,4-dimethoxyl-phenyl)-furan-2-carbaldehyde: $^1$H NMR (400 MHz, CDCl$_3$): δ 3.87 (3H, s), 3.94 (3H, s), 6.53 (1H, d, J=2.0 Hz), 6.60 (1H, dd, J=8.8 Hz, J=2.0 Hz), 7.00 (1H, d, J=3.6 Hz), 7.31 (1H, d, J=4.0 Hz), 7.97 (1H, d, J=8.8), 9.59 (1H, s). ESI-Mass: 233.1

ALD 54: 5-(2,6-dimethyl-phenyl)-furan-2-carbaldehyde: $^1$H NMR (400 MHz, CDCl$_3$): δ 2.29 (6H, s), 6.50 (2H, d, J=3.6 Hz), 7.11 (2H, m), 7.19 (1H, m), 7.32 (1H, d, J=3.6 Hz), 9.67 (1H, s).

ALD 55: 5-(2-benzyloxy-phenyl)-furan-2-carbaldehyde: $^1$H NMR (400 MHz, CDCl$_3$): δ 5.21 (2H, s), 7.11 (3H, m), 7.25 (1H, m), 7.33-7.48 (6H, m), 8.10 (1H, m), 9.63 (1H, s). MS-ESI+: 279.0.

ALD 56: 5-(4-dimethylamino-2-methyl-phenyl)-furan-2-carbaldehyde: $^1$H NMR (400 MHz, CDCl$_3$): δ 2.53 (3H, s), 3.02 (6H, s), 6.55 (1H, d, J=2.8 Hz), 6.58 (1H, d, J=3.6 Hz), 6.62 (1H, dd, J=8.4 Hz, 2.4 Hz), 7.31 (1H, d, J=3.6 Hz), 7.72 (1H, d, J=8.8 Hz), 9.57 (1H, s). MS-ESI+: 230.4.

ALD 57: 5-(2,4,6-trimethyl-phenyl)-furan-2-carbaldehyde: $^1$H NMR (400 MHz, CDCl$_3$): δ 2.18 (6H, s), 2.32 (3H, s), 6.49 (1H, d, J=3.6 Hz), 6.94 (2H, s), 7.34 (1H, d, J=3.6 Hz), 9.66 (1H, s). MS-ESI+: 215.3.

ALD 58: 5-(4-ethyl-phenyl)-furan-2-carbaldehyde: $^1$H NMR (400 MHz, CDCl$_3$): δ 125 (3H, t, J=2.4 Hz), 2.70 (2H, q), 6.80 (1H, d, J=3.6 Hz), 7.28 (2H, m), 7.32 (1H, d, J=4 Hz), 7.75 (2H, m), 9.63 (1H, s). MS-ESI+: 201.0.

ALD 59: 5-(4-trifluoromethyl-phenyl)-furan-2-carbaldehyde: $^1$H NMR (400 MHz, CDCl$_3$): δ 6.95 (1H, d, J=3.6 Hz), 7.35 (1H, d, J=4.0 Hz), 7.71 (2H, d, J=8.0 Hz), 7.95 (2H, d, J=8.4 Hz), 9.71 (1H, s). ESI-Mass: 241.2

ALD 60: 5-(4-fluoro-phenyl)-furan-2-carbaldehyde: $^1$H NMR (400 MHz, CDCl$_3$): δ 6.79 (1H, d, J=4 Hz), 7.17 (2H, m), 7.32 (1H, d, J=3.6 Hz), 7.82 (2H, m), 9.65 (1H, s).

ALD 61: 5-(4-ethoxy-phenyl)-furan-2-carbaldehyde: $^1$H NMR (400 MHz, CDCl$_3$): δ 1.44 (3H, t, J=6.8 Hz), 4.10 (2H, q), 6.71 (1H, d, J=3.6 Hz), 6.95 (2H, m), 7.31 (1H, d, J=4 Hz), 7.75 (2H, m), 9.60 (1H, s).

ALD 62: 5-(4-propyl-phenyl)-furan-2-carbaldehyde: $^1$H NMR (400 MHz, CDCl$_3$): δ 0.96 (3H, t, J=7.6 Hz), 1.64 (2H, m), 2.63 (2H, t, J=7.6 Hz), 6.80 (1H, d, J=3.6 Hz), 7.27 (2H, m), 7.32 (1H, d, J=4 Hz), 7.74 (2H, m), 9.63 (1H, s).

ALD 63: 5-(4-butyl-phenyl)-furan-2-carbaldehyde: $^1$H NMR (400 MHz, CDCl$_3$): δ 0.96 (3H, t, J=7.6 Hz), 1.36 (2H, m), 1.66 (2H, m), 2.64 (2H, t, J=7.6 Hz), 6.80 (1H, d, J=4 Hz), 7.27 (2H, m), 7.32 (1H, d, J=4 Hz), 7.75 (2H, m), 9.63 (1H, s). MS-ESI+: 229.3.

ALD 64: N-[4-(5-formyl-furan-2-yl)-phenyl]-acetamide: $^1$H NMR (400 MHz, CDCl$_3$): δ 2.22 (3H, s), 6.79 (1H, d, J=3.6 Hz), 7.32 (1H, d, J=3.6 Hz), 7.54 (1H, bs), 7.65 (2H, m), 7.78 (2H, m), 9.62 (1H, s).

ALD 65: 5-(4-methanesulfonyl-phenyl)-furan-2-carbaldehyde: $^1$H NMR (400 MHz, CDCl$_3$): δ 3.10 (3H, s), 7.02 (1H, d, J=4.0 Hz), 7.36 (1H, d, J=4.0 Hz), 8.02 (4H, m), 9.73 (1H, s).

ALD 68: 5-(4-isopropoxy-phenyl)-furan-2-carbaldehyde: $^1$H NMR (400 MHz, CDCl$_3$): δ 1.37 (6H, d, J=6.0 Hz), 4.62 (1H, septet, J=6.0 Hz), 6.70 (1H, d, J=3.6 Hz), 6.94 (2H, m), 7.30 (1H, d, J=4.0 Hz), 7.75 (2H, m), 9.60 (1H, s). MS-ESI+: 231.3.

ALD 73: 5-(2-phenoxy-phenyl)-furan-2-carbaldehyde: $^1$H NMR (400 MHz, CDCl$_3$): δ 6.93 (1H, dd, J=8.4 Hz, J=1.2 Hz), 7.03-7.05 (2H, m), 7.12 (1H, d, J=3.6 Hz), 7.14-7.24 (2H, m), 7.29 (1H, d, J=3.6 Hz), 7.30-7.39 (3H, m), 8.13 (1H, dd, J=7.6 Hz, J=1.6 Hz), 9.66 (1H, s). ESI-Mass: 265.2

ALD 76: 5-(4-chloro-2-methyl-phenyl)-furan-2-carbaldehyde: $^1$H NMR (400 MHz, CDCl$_3$): δ 2.53 (3H, s), 6.74 (1H, d, J=4.0 Hz), 7.26-7.29 (2H, m), 7.34 (1H, d, J=3.6 Hz), 7.74 (1H, d, J=8.0 Hz), 9.68 (1H, s). ESI-Mass: 221.3.

ALD 77: 5-(4-fluoro-2-methoxy-phenyl)-furan-2-carbaldehyde: $^1$H NMR (400 MHz, CDCl$_3$): δ 3.96 (3H, s), 6.71-6.79 (2H, m), 7.06 (1H, d, J=3.6 Hz), 7.31-7.32 (1H, m), 8.00-8.03 (1H, m), 9.63 (1H, s). ESI-Mass: 221.3

General Procedure for the Synthesis of Appropriately Substituted 4-oxo-2-thioxo-thiazolidin-3-yl-cyclohexanecarboxylic acids:

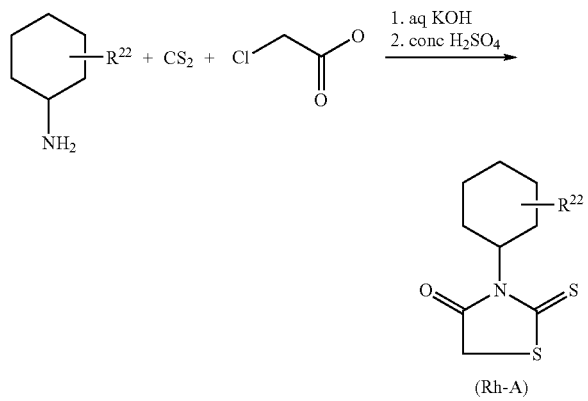

(Rh-A)

To a round bottom flask containing appropriately substituted amino-cyclohexanecarboxylic acid (26.54 mmol) was added aqueous potassium hydroxide (53.08 mmol) in water (20 mL).) The reaction mixture was stirred at room temperature for 15 minutes. Carbon disulfide (26.54 mmol) was added drop-wise to the reaction mixture which was then stirred at room temperature for 1.5 h. The reaction mixture was cooled to 0° C. and an aqueous solution of chloroacetic acid (26.54 mmol) and potassium hydroxide (26.54 mmol) in water (15 mL) was added slowly to the reaction mixture. The cooling bath was removed and the reaction mixture stirred at room temperature for 1.5 h. The reaction mixture was cooled to 0° C. and acidified with concentrated sulfuric acid (3 mL). The cooling bath was removed and the reaction mixture was heated at 100° C. for 8 h and allowed to cool to room temperature overnight. The solid was filtered, washed with water (15 mL), 1:1 hexanes/ether (100 mL) and hexanes (100 mL). The solid was dried in vacuum oven at 55-60° C. for 5 h to afford appropriately substituted 4-oxo-2-thioxo-thiazolidin-3-yl-cyclohexanecarboxylic acid.

Data for representative analogs (Rh-A) is listed below:

3-(4-oxo-2-thioxo-thiazolidin-3-yl)-cyclohexanecarboxylic acid: $^1$H NMR (400 MHz, DMSO-$d_6$): δ 1.16-1.39 (2H, m), 1.57 (1H, m), 1.79-1.89 (3H, m), 1.96-2.36 (3H, m), 4.12 (2H, s), 4.79 (1H, m), 12.18 (1H, s); APCI-MS: 258.31.

4-(4-oxo-2-thioxo-thiazolidin-3-yl)-cyclohexanecarboxylic acid. $^1$H NMR (400 MHz, DMSO-$d_6$): δ 1.54-1.57 (2H, m), 1.89-1.93 (2H, m), 18 (2H, m), 2.26-2.31 (2H, m), 3.42 (1H, m), 4.11 (2H, s), 4.63 (1H, m), 4.70 (1H, m); APCI-MS: 258.0.

3-(4-hydroxy-cyclohexyl)-2-thioxo-thiazolidin-4-one: $^1$H NMR (400 MHz, DMSO-$d_6$): δ 1.14-1.25 (2H, m), 1.57 (1H, m), 1.79-1.89 (3H, m), 1.96-2.36 (3H, m), 4.092 (2H, s), 4.79 (1H, m), 12.18 (1H, s); APCI-MS: 229.9.

General procedure for the synthesis of compounds listed in Table 3 (Compounds C1 to C90):

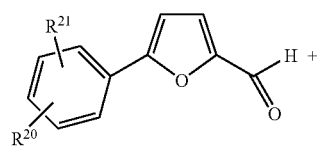

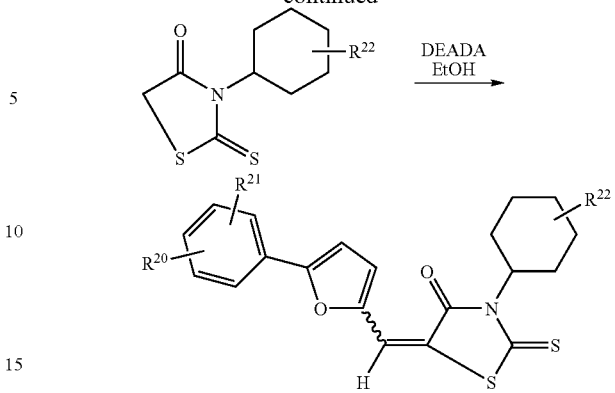

A mixture of appropriately substituted 4-oxo-2-thioxo-thiazolidin-3-yl-cyclohexyl carboxylic acid (0.29 mmol), appropriately substituted-(5-phenyl)-furan-2-carbaldehyde and (0.31 mmol) and ethylenediamine diacetate (0.031 mmol) in methanol (10 mL) was stirred at room temperature for 18 h. The reaction mixture was poured into stirred 0.6 N aq sodium hydrogensulfite (50 mL). The mixture was vigorously stirred for 30 min. The solid product was filtered off and washed on funnel successively with 0.6 N aq sodium hydrogensulfite (1 mL), water (2×2 mL), ether (2×1 mL) and hexanes (2 mL). The material was dried in vacuum oven at 65° C. for 17 h to afford the desired target compound.

(Compound C1): 3-{5-[1-[5-(2-chloro-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.25-1.31 (1H, m), 1.34-1.41 (1H, m), 1.69 (1H, m), 1.90 (3H, m), 2.28-2.45 (3H, m), 4.95 (1H, m), 7.40 (1H, d, J=3.6), 7.43 (1H, d, J=3.6), 7.46 (1H, m), 7.62 (1H, s), 7.62 (2H, m), 7.92 (1H, m), 12.22 (1H s). LC/MS: APCI 447.33, HPLC 100%.

(Compound C2): 3-{5-[1-[5-(4-cyclohexyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.25-1.49 (7H, m), 1.67-1.92 (10H, m), 2.35-2.45 (2H, m), 2.56 (1H, m), 4.97 (1H, m), 7.26 (1H, d, J=3.6 Hz), 7.36 (1H, d, J=3.6 Hz), 7.42 (1H, d, J=8.4 Hz), 7.59 (1H, s), 7.77 (1H, d, J=8.4 Hz), 12.18 (1H, s); APCI-MS: 495.37; HPLC: 90%.

(Compound C3): 3-{5-[1-[5-(4-tert-butyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.32 (9H, s), 1.25-1.41 (2H, m), 1.67 (1H, m), 1.87-1.92 (3H, m), 2.29-2.45 (3H, m), 4.98 (1H, m), 7.26 (1H, d, J=3.6 Hz), 7.36 (1H, d, J=3.6 Hz), 7.59-7.61 (3H, m), 7.77-7.70 (2H, m), 12.20 (1H, s); APCI-MS: 469.52; HPLC: 95%.

(Compound C4): 3-{5-[1-[5-(4-isobutyl-phenyl)-furan-2-yl]methylidene]-4-oxo-2-thioxo-thiazolidin-3-yl}-cyclohexanecarboxylic acid; $^1$H NMR (400 MHz, DMSO-$d_6$): δ 0.88 (6H, d, J=6.4 Hz), 1.16-1.45 (2H, m), 1.68 (1H, m), 1.84-1.92 (4H, m), 2.25-2.54 (3H, m), 4.98 (1H, m), 7.27 (1H, d, J=3.6 Hz), 7.36 (2H, m), 7.36 (1H, d, J=3.6 Hz), 7.58 (1H, s), 7.77 (2H, m), 12.22 (1H, s). LC/MS. APCI 469.51, HPLC 100%.

(Compound C5): 3-{5-[1-[5-(3-trifluoromethyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.25-1.41 (2H, m), 1.67 (1H, m), 1.87-1.92 (3H, m), 2.29-2.45 (3H, m), 4.97 (1H, m), 7.37 (1H, d, J=3.6 Hz), 7.55 (1H, d, J=3.6 Hz), 7.62 (1H, s), 7.77-7.85 (2H, m), 8.11-8.18 (2H, m), 12.18 (1H, s). LC/MS: APCI-MS: 481.47; HPLC: 95%.

(Compound C6): 3-{5-[1-[5-(4-benzyl-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.25-2.45 (3H, m), 4.00 (2H, s), 4.97 (1H, m), 7.18-7.22 (1H, m), 7.26-7.32 (5H, m), 7.36 (1H, d, J=3.6 Hz) 7.43 (2H, m), 7.58 (1H, s), 7.77 (1H, d, J=8.0 Hz), 12.18 (1H, s). LC/MS: APCI-MS: 503.54; HPLC: 95%.

(Compound C7): 3-{5-[1-[5-(2,4-difluoro-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 4.97 (1H, m), 7.15 (1H, t, J=3.6 Hz), 7.39-744 (2H, m), 7.49-7.55 (1H, m), 7.62 91H, s), 7.88-7.94 (1H, m). LC/MS: APCI 449.0, HPLC 98%.

(Compound C8): 3-{5-[1-[5-(2,4-dimethyl-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 2.33 (3H, s), 2.52 (3H, s), 4.97 (1H, m), 7.04 (1H, d, J=4 Hz), 7.20 (1H, bs), 7.25 (1H, d, J=8 Hz), 7.40 (1H, d, J=4 Hz), 7.60 (1H, s), 7.69 (1H, d, J=8 Hz). LC/MS: APCI 441.1, HPLC 95%.

(Compound C9): 3-{5-[1-[5-(2-methyl-4-methoxy-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 2.64 (3H, s), 3.82 (3H, s), 4.97 (1H, m), 6.97 (2H, d, J=4 Hz), 7.05 (1H, dd, J=2.8 & 8.8 Hz), 7.38 (1H, d, J=4 Hz), 7.59 (1H, s), 7.74 (1H, d, J=8.4 Hz). LC/MS: APCI 457.1, HPLC 90%.

(Compound C10): 3-[4-Oxo-2-thioxo-5-(6-o-tolyl-pyridin-2-ylmethylene)-thiazolidin-3-yl]-cyclohexanecarboxylic acid; $^1$H NMR (400 MHz, DMSO-d$_6$): δ 1.25-1.32 (1H, m), 1.34-1.42 (1H, m), 1.67-1.71 (1H, m), 1.88-1.91 (3H, m), 2.28-2.45 (3H, m), 2.41 (1H, s), 5.08 (1H, m), 7.32-7.38 (4H, m), 7.44-7.51 (2H, m), 7.59 (1H, s), 7.81-7.84 (1H, m). LC/MS: APCI 438.1, HPLC 88%.

(Compound C11): 3-{5-[1-[5-(2-methyl-4-fluoro-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 2.54 (3H, s), 4.97 (1H, m), 7.07 (1H, d, J=3.6 Hz), 7.30 (1H, m), 7.40 (1H, d, J=4 Hz), 7.61 91H, s), 7.82 (1H, m). LC/MS: APCI 445.0, HPLC 95%.

(Compound C12): 3-{5-[1-[5-(2-fluoro-4-methyl-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 2.38 (3H, s), 4.97 (1H, m), 7.09 (1H, t, J=3.2 Hz), 7.28 (2H, m), 7.38 (1H, d, J=3.6 Hz), 7.61 (1H, s), 7.75 (1H, t, J=8 Hz). LC/MS: APCI 445.0, HPLC 93%.

(Compound C13): 3-{5-[1-[5-(2-hydroxy-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 4.97 (1H, m), 7.02-7.07 (2H, m), 7.24-7.29 (2H, m), 7.37 91H, d, J=4 Hz), 7.61 (1H, s), 7.78 (1H, m). LC/MS: APCI 428.0, HPLC 92%.

(Compound C14): 3-{4-oxo-2-thioxo-5-[1-(5-p-tolyl-furan-2-yl)-methylidene]-thiazolidin-3-yl}-cyclohexanecarboxylic acid; $^1$H NMR (400 MHz, DMSO-d$_6$): δ 1.23-1.38 (2H, m), 1.65-1.68 (1H, m), 1.86-1.89 (3H, m), 2.25-2.33 (2H, m), 2.37 (3H, s), 2.66 (1H, m), 4.97 (1H, m), 7.27 (1H, d, J=3.6 Hz), 7.36-7.39 (3H, m), 7.58 (1H, s), 7.74-7.76 (2H, m), APCI-MS: 427.0; HPLC: 97%.

(Compound C15): 3-{5-[1-[5-(4-methoxy-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.23-1.39 (2H, m), 1.65-1.68 (1H, m), 1.86-1.89 (3H, m), 2.26-2.32 (2H, m), 2.66 (1H, s), 3.83 (3H, s), 4.96 (1H, m), 7.13-7.17 (2H, m), 7.19 (1H, d, J=4.0 Hz), 7.35 (1H, d, J=3.6 Hz), 7.57 (1H, s), 7.79-7.82 (2H, m), APCI-MS: 443.0; HPLC: 95%.

(Compound C16): 4-{5-[1-[5-(2-chloro-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.48-1.57 (4H, m), 2.18 (2H, m), 2.46 (2H, m), 2.61 (1H, m), 4.91 (1H, m), 7.40 (1H, d, J=3.6 Hz), 7.44 (1H, d, J=3.6 Hz), 7.45-7.49 (1H, m), 7.59 (1H, s), 7.63-7.66 (2H, m), 7.93 (1H, m). LC/MS: APCI 447.0, HPLC 100%.

(Compound C17): 4-{5-[1-[5-(3-trifluoromethyl-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.48-1.57 (4H, m), 2.18 (2H, m), 2.46 (2H, m), 2.61 (1H, m), 4.91 (1H, m), 7.39 (1H, d, J=4 Hz), 7.56 (1H, d, J=3.6 Hz), 7.58 (1H, s), 7.78-7.85 (2H, m), 8.13 (1H, d, J=7.6 Hz), 8.17 (1H, bs). LC/MS: APCI 481.0, HPLC 100%.

(Compound C18): 4-{5-[1-[5-(4-chloro-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.48-1.57 (4H, m), 2.18 (2H, m), 2.46 (2H, m), 2.61 (1H, m), 4.91 (1H, m), 7.37 (2H, m), 7.55 (1H, s), 7.66 (2H, m), 7.87 (2H, m). LC/MS APCI 447.0, HPLC 100%.

(Compound C19): 3-{5-[1-[5-(2,4-dimethoxy-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.42-1.53 (2H, m), 1:73-1.76 (2H, m), 1.99-2.09 (4H, m), 2.52 (1H, m), 3.89 (3H, s), 3.94 (3H, s), 5.10 (1H, m), 6.54 (1H, d, J=3.2 Hz), 6.71 (1H, dd, J=8.8 Hz, J=2.4 Hz), 6.95-7.02 (2H, m), 7.37 (1H, s), 7.91 (1H, d, J=8.4 Hz), APCI-MS: 473.1; HPLC 92%.

(Compound C20): 3-{5-[1-[5-(4-chloro-2-methyl-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.26-1.41 (2H, m), 1.67-1.70 (1H, m), 1.90 (3H, m), 2.37 (3H, m), 2.53 (3H, s), 4.96 (1H, m), 7.14 (1H, d, J=3.6 Hz), 7.40 (1H, d, J=3.6 Hz), 7.50-7.53 (2H, m), 7.61 (1H, s), 7.77-7.79 (1H, m), APCI-MS: 461.0; HPLC: 99%.

(Compound C21): 5-[1-[5-(2-chloro-phenyl)-furan-2-yl]-methylidene]-3-(4-hydroxy-cyclohexyl)-2-thioxo-thiazolidin-4-one; $^1$H NMR (400 MHz, DMSO-d$_6$): δ 1.20-1.30 (2H, m), 1.67 (2H, m), 1.96 92H, m), 2.45 (2H, m), 3.46 (1H, m), 4.67 (1H, d, J=4 Hz), 4.87 (1H, m), 7.40 (1H, d, J=4 Hz), 7.44 (1H, d, J=3.6 Hz), 7.45-7.49 (1H, m), 7.58-7.66 (3H, m), 7.93 (1H, m). LC/MS: APCI 419.0, HPLC 96%.

(Compound C22): 5-[1-[5-(4-chloro-phenyl)-furan-2-yl]-methylidene]-3-(4-hydroxy-cyclohexyl)-2-thioxo-thiazolidin-4-one; $^1$H NMR (400 MHz, DMSO-d$_6$): δ 1.20-1.30 (2H, m), 1.67 (2H, m), 1.96 92H, m), 2.45 (2H, m), 3.46 (1H, m), 4.67 (1H, d, J=4 Hz), 4.87 (1H, m), 7.38 92H, m), 7.59 (1H, s), 7.66 (2H, d, J=8.8 Hz), 7.87 (2H, d, J=8.4 Hz). LC/MS: APCI 419.0, HPLC 97%.

(Compound C23): 3-{5-[5-(2,6-Dimethyl-phenyl)-furan-2-ylmethylene]-4-oxo-2-thioxo-thiazolidin-3-yl}-cyclohexanecarboxylic acid; $^1$H NMR (400 MHz, DMSO-d$_6$): δ 1.25-1.31 (1H, m), 1.34-1.41 (1H, m), 1.67-1.70 (1H, m), 1.87-1.92 (3H, m), 2.23 (6H, s), 2.16-2.39 (3H, m), 4.95 (1H, m), 6.89 (1H, d, J=3.6 Hz), 7.21 (2H, d, J=7.6 Hz), 7.31 (1H, dd, J=8.0 Hz, 7.2 Hz), 7.40 (1H, d, J=3.6 Hz), 7.62 (1H, s). LC/MS: APCI 441.1, HPLC 96%.

(Compound C24): 3-{5-[1-(2'-methyl-biphenyl-3-yl)-methylidene]-4-oxo-2-thioxo-thiazolidin-3- yl}cyclohexanecarboxylic acid; $^1$H NMR (400 MHz, DMSO-d$_6$): δ 1.25-1.41 (2H, m), 1.67 (1H, m), 1.87-1.92 (3H, m), 2.26 (3H, s), 2.29-2.45 (3H, m), 4.96 (1H, m), 7.24-7.35 (4H, m), 7.48-7.51 (1H, m), 7.58 (1H, bs), 7.60-7.66 (2H, m), 7.81 (1H, s). LC/MS: APCI 437.1, HPLC 81%.

(Compound C25): 3-{5-[1-[5-(4-fluoro-2-methoxy-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.40 (2H, m), 1.66-1.69 (1H, m), 1.89-1.91 (3H, m), 2.33-2.55 (3H, m), 3.98 (3H, s), 4.97 (1H, m), 7.08-7.16 (2H, m), 7.17 (1H, d, J=3.6 Hz), 7.36 (1H, d, J=3.6 Hz), 7.60 (1H, s), 7.81-7.85 (1H, m), APCI-MS: 461.0; HPLC: 95%.

(Compound C26): 3-{5-[1-[5-(3-fluoro-4-methoxy-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.23-1.40 (2H, m), 1.65-1.68 (1H, m), 1.87-1.90 (3H, m), 2.31-2.66 (3H, m), 3.91 (3H, s), 4.97 (1H, m), 7.27-7.36 (2H, m), 7.42 (1H, m), 7.58 (1H, s), 7.62-7.65 (1H, m), 7.69-7.73 (1H, m), APCI-MS: 461.1; HPLC: 95%.

(Compound C27): 3-{5-[1-[5-(2-benzyloxy-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 4.96 (1H, m), 5.32 (2H, s), 7.12 (1H, d, J=3.6 hz), 7.22 (1H, m), 7.30-7.53 (8H, m), 7.58 (1H, s), 7.88 (1H, m). LC/MS: APCI 519.0, HPLC 93%.

(Compound C28): 3-{4-Oxo-2-thioxo-5-[5-(2,4,6-trimethyl-phenyl)-furan-2-ylmethylene]-thiazolidin-3-yl}-cyclohexanecarboxylic acid; $^1$H NMR (400 MHz, DMSO-d$_6$): δ 1.25-1.31 (1H, m), 1.34-1.41 (1H, m), 1.67-1.70 (1H, m), 1.87-1.92 (3H, m), 2.20 (6H, s), 2.30 (3H, s), 2.28-2.45 (3H, m), 4.95 (1H, m), 6.84 (1H, d, J=3.6 Hz), 7.03 (2H, s), 7.38 (1H, d, J=3.6 Hz), 7.61 (1H, s). LC/MS: APCI 455.1, HPLC 96%.

(Compound C29): 3-{5-[5-(4-Dimethylamino-2-methyl-phenyl)-furan-2-ylmethylene]-4-oxo-2-thioxo-thiazolidin-3-yl}-cyclohexanecarboxylic acid; $^1$H NMR (400 MHz, DMSO-d$_6$): δ 1.25-1.31 (1H, m), 1.34-1.41 (1H, m), 1.67-1.70 (1H, m), 1.87-1.92 (3H, m), 2.28-2.45 (3H, m), 2.49 (3H, s), 2.99 (6H, s), 4.95 (1H, m), 6.67 (1H, d, J=2.4 Hz), 6.79 (1H, dd, J=8.8 Hz, 2.8 Hz), 6.86 (1H, d, J=4.0 Hz), 7.37 (1H, d, J=4.0 Hz), 7.55 (1H, s), 7.67 (1H, d, J=8.8 Hz). LC/MS: APCI 470.1, HPLC 100%.

(Compound C30): 3-{5-[1-[5-(2-methylsulfanyl-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.23-1.38 (2H, m), 1.65-1.68 (1H, m), 1.86-1.89 (3H, m), 2.25-2.38 (2H, m), 2.56 (3H, s), 2.66 (1H, s), 4.97 (1H, m), 7.25 (1H, d, J=3.6 Hz), 7.37-7.41 (2H, m), 7.46-7.47 (2H, m), 7.62 (1H, s), 7.78-7.79 (1H, m), LC/MS. APCI 459.0, HPLC 96%.

(Compound C31): 3-{4-oxo-2-thioxo-5-[1-(5-o-tolyl-thiophen-2-yl)-methylidene]-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 2.49 (3H, s), 4.94 (1H, m), 7.29-7.38 (3H, m), 7.46 (1H, d, J=4 Hz), 7.52 (1H, m), 7.81 (1H, d, J=4 Hz), 8.01 (1H, s). LC/MS: APCI 443.0, HPLC 85%.

(Compound C32): 3-{4-oxo-2-thioxo-5-[1-(5-(2-chloro-phenyl)-thiophen-2-yl)-methylidene]-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 4.94 (1H, m), 7.46-7.49 (2H, m), 7.63-7.66 (1H, m), 7.68 (1H, d, J=4 Hz), 7.76-7.78 (1H, m), 7.82 (1H, d, J=4.4 Hz), 8.02 (1H, s). LC/MS: APCI 463.0.

(Compound C33): 3-{5-[2-(2-Chloro-benzyloxy)-benzylidene]-4-oxo-2-thioxo-thiazolidin-3-yl}-cyclohexanecarboxylic acid; $^1$H NMR (400 MHz, DMSO-d$_6$): δ 1.25-1.31 (1H, m), 1.34-1.41 (1H, m), 1.67-1.70 (1H, m), 1.87-1.92 (3H, m), 2.28-2.45 (3H, m), 4.95 (1H, m), 5.13 (2H, s), 7.16 (1H, m), 7.31 (1H, m), 7.40-7.45 (3H, m), 7.51-7.53 (1H, m), 7.55-7.57 (1H, m), 7.60-7.62 (1H, m), 7.93 (1H, s).

(Compound C34): 3-{4-oxo-5-[1-[5-(2-phenoxy-phenyl)-furan-2-yl]-methylidene]-2-thioxo-thiazolidin-3-yl}-cyclohexanecarboxylic acid; $^1$H NMR (400 MHz, DMSO-d$_6$): δ 1.23-1.39 (2H, m), 1.65-1.69 (1H, m), 1.88-1.89 (3H, m), 2.23-2.33 (2H, m), 2.66 (1H, s), 4.96 (1H, m), 7.00-7.03 (1H, m), 7.06-7.09 (2H, m), 7.13 (1H, d, J=3.6 Hz), 7.16-7.20 (1H, m), 7.33 (1H, d, J=3.6 Hz), 7.40-7.46 (4H, m), 7.61 (1H, s), 7.96-7.98 (1H, m), LC/MS: APCI 505.1, HPLC 87%.

(Compound C35): 3-{5-[1-[5-(2-fluoro-phenyl)-thiophen-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 4.94 (1H, m), 7.32-7.49 (3H, m), 7.82 (2H, bs), 7.96 (1H, m), 8.03 (1H, s). LC/MS: APCI 447.0, HPLC 95%.

(Compound C36): 3-{5-[1-[5-(4-ethyl-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.19 (3H, t, J=7.6 Hz), 1.25-1.41 (2H, m), 1.67 (1H, m), 1.87-1.92 (3H, m), 2.29-2.45 (3H, m), 2.67 (2H, q), 4.97 (1H, m), 7.28 (1H, d, J=3.6 Hz), 7.37 (1H, d, J=4 Hz), 7.42 (2H, d, J=8 Hz), 7.59 (1H, s), 7.78 (2H, d, J=8 Hz). LC/MS: APCI 441.1, HPLC 97%.

(Compound C37): 3-{4-oxo-2-thioxo-5-[1-[5-(4-trifluoromethyl-phenyl)-furan-2-yl]-methylidene]-thiazolidin-3-yl}-cyclohexanecarboxylic acid; $^1$H NMR (400 MHz, DMSO-d$_6$): δ 1.23-1.38 (2H, m), 1.67 (1H, m), 1.87-1.90 (3H, m), 2.26-2.38 (2H, m), 2.67 (1H, s), 4.96 (1H, m), 7.39 (1H, d, J=3.6 Hz), 7.51 (1H, d, J=3.6 Hz), 7.62 (1H, s), 7.92-8.05 (4H, m); APCI-MS: 481.0; HPLC: 100%.

(Compound C38): 3-{5-[1-(5-biphenyl-3-yl-furan-2-yl)-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67-1.70 (1H, m), 1.89-1.92 (3H, m), 2.33-2.55 (3H, m), 4.98 (1H, m), 7.39 (1H, d, J=3.6 Hz), 7.42-7.54 (4H, m), 7.63 (1H, s), 7.67-7.86 (5H, m), 8.15-8.16 (1H, m), LC/MS: APCI 489.1, HPLC 99%.

(Compound C39): 3-{5-[5-(4-Acetylamino-phenyl)-furan-2-ylmethylene]-4-oxo-2-thioxo-thiazolidin-3-yl}-cyclohexanecarboxylic acid; $^1$H NMR (400 MHz, DMSO-d$_6$): δ 1.25-1.31 (1H, m), 1.34-1.41 (1H, m), 1.67-1.70 (1H, m), 1.87-1.92 (3H, m), 2.08 (3H, s), 2.28-2.45 (3H, m), 4.99 (1H, m), 7.21 (1H, d, J=3.6 Hz), 7.36 (1H, d, J=3.6 Hz), 7.57 (1H, s), 7.75-7.80 (4H, m), 10.21 (1H, s). LC/MS: APCI 470.1, HPLC 91%.

(Compound C40): 3-{5-[1-[5-(4-acetyl-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.23-1.41 (2H, m), 1.68-1.71 (1H, m), 1.91 (3H, m), 2.33-2.45 (2H, m), 2.61 (1H, m), 3.32 (3H, s), 4.98 (1H, m), 7.40 (1H, d, J=4.0 Hz), 7.51 (1H, d, J=4.0 Hz), 7.63 (1H, s), 7.96-8.15 (4H, m), APCI-MS: 455.1; HPLC: 92%.

(Compound C41): 3-{5-[1-[5-(2-fluoro-phenyl)-furan-2-yl]-methylidene]-4-oxo-2-thioxo-thiazolidin-3-yl}-cyclohexanecarboxylic acid; $^1$H NMR (400 MHz, DMSO-d$_6$): δ 1.25-1.41 (2H, m), 1.67 (1H, m), 1.87-1.92 (3H, m), 2.29-2.45 (3H, m), 4.97 (1H, m), 7.17 (1H, t, J=3.6 Hz), 7.38-7.52 (4H, m), 7.63 (1H, s), 7.86-7.91 (1H, m). LC/MS: APCI 431.0, HPLC 96%.

(Compound C42): 3-{5-[1-[5-(3-hydroxymethyl-phenyl)-furan-2-yl]-methylidene]-4-oxo-2-thioxo-thiazolidin-3-yl}- cyclohexanecarboxylic acid; $^1$H NMR (400 MHz, DMSO-$d_6$): δ 1.25-1.41 (2H, m), 1.67 (1H, m), 1.87-1.92 (3H, m), 2.29-2.45 (3H, m), 4.59 (2H, s), 4.98 (1H, m), 5.35 (1H, m), 732 (1H, d, J=3.6 Hz), 7.37-7.39 (2H, m), 7.53 (1H, m), 7.60 (1H, s), 7.72-7.83 (2H, m); APCI-MS: 443.1, HPLC: 96%.

(Compound C43): 3-{5-[1-[5-(4-fluoro-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.25-1.41 (2H, m), 1.67 (1H, m), 1.87-1.92 (3H, m), 2.29-2.45 (3H, m), 4.95 (1H, m), 7.32 (1H, d, J=4 Hz), 7.37 (1H, d, J=3.2 Hz), 7.43 (2H, t, J=8.4 Hz), 7.59 (1H, s), 7.89 (2H, m). LC/MS: APCI 431.0, HPLC 97%.

(Compound C44): 4-{5-[1-[5-(2-fluoro-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.48-1.57 (4H, m), 2.18 (2H, m), 2.46 (2H, m), 2.61 (1H, m), 4.91 (1H, m), 7.16 (1H, t, J=3.6 Hz), 7.39 (1H, d, J=3.6 Hz), 7.41-7.52 (3H, m), 7.58 (1H, s), 7.85-7.90 (1H, m). LC/MS: APCI 431.0, HPLC 100%.

(Compound C45): 4-{4-oxo-2-thioxo-5-[1-(5-p-tolyl-furan-2-yl)-methylidene]-thiazolidin-3-yl}-cyclohexanecarboxylic acid; $^1$H NMR (400 MHz, DMSO-$d_6$): δ 1.48-1.57 (4H, m), 2.18 (2H, m), 2.37 (3H, s), 2.46 (2H, m), 2.61 (1H, m), 4.91 (1H, m), 7.27 (1H, d, J=3.6 Hz), 7.34-7.39 (3H, m), 7.54 (1H, s), 7.75 (2H, d, J=8.4 Hz). LC/MS: APCI 427.1, HPLC 100%.

(Compound C46): 4-{5-[1-[5-(2-fluoro-4-methyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.48-1.57 (4H, m), 2.18 (2H, m), 2.38 (3H, s), 2.46 (2H, m), 2.61 (1H, m), 4.91 (1H, m), 7.10 (1H, t, J=3.6 Hz), 7.28 (2H, m), 7.38 (1H, d, J=3.6 Hz), 7.57 (1H, s), 7.75 (1H, t, J=8.4 Hz). LC/MS: APCI 445.0, HPLC 100%.

(Compound C47): 4-{5-[1-[5-(2-fluoro-phenyl)-thiophen-2-yl]-methylidene]-4-oxo-2-thioxo-thiazolidin-3-yl}-cyclohexanecarboxylic acid; $^1$H NMR (400 MHz, DMSO-$d_6$): δ 1.48-1.57 (4H, m), 2.18 (2H, m), 2.46 (2H, m), 2.61 (1H, m), 4.89 (1H, m), 7.32-7.48 (3H, m), 7.81 (2H, m), 7.94 (1H, m), 7.98 (1H, s). LC/MS: APCI 447.0.

(Compound C51): 3-{5-[1-[5-(4-ethoxy-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.25-1.41 (2H, m), 1.36 (3H, t, J=7.2 Hz), 1.67 (1H, m), 1.87-1.92 (3H, m), 2.29-2.45 (3H, m), 4.11 (2H, q), 4.97 (1H, m), 7.14 (3H, m), 7.35 (1H, m), 7.57 (1H, s), 7.80 (2H, m). LC/MS: APCI 457.1, HPLC 95%.

(Compound C52): 4-{5-[1-[5-(4-ethoxy-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.36 (3H, t, J=6.8 Hz), 1.48-1.57 (4H, m), 2.18 (2H, m), 2.38 (3H, s), 2.46 (2H, m), 2.61 (1H, m), 4.12 (2H, q), 4.91 (1H, m), 7.13 (2H, m), 7.19 (1H, d, J=3.6 Hz), 7.35 (1H, d, J=4 Hz), 7.52 (1H, s), 7.79 (2H, m). LC/MS: APCI 457.1, HPLC 95%.

(Compound C53): 4-{5-[1-[5-(3-fluoro-4-methoxy-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.49-1.57 (4H, m), 2.18-2.22 (2H, m), 2.46-2.61 (3H, m), 3.91 (3H, s), 4.91 (1H, m), 7.26 (1H, d, J=3.6 Hz), 7.34 (1H, d, J=3.6 Hz), 7.39-7.44 (1H, m), 7.53 (1H, s), 7.62-7.72 (2H, m); APCI-MS: 461.0; HPLC: 87%.

(Compound C54): 4-{5-[1-[5-(2-methylsulfanyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.49-1.57 (4H, m), 2.18-2.20 (2H, m), 2.45-2.62 (3H, m), 2.56 (3H, m), 4.91 (1H, m), 7.24 (1H, d, J=3.6 Hz), 7.36-7.40 (2H, m), 7.45-7.47 (2H, m), 7.57 (1H, s), 7.77-7.79 (1H, m), LC/MS: APCI 459.0, HPLC 89%.

(Compound C55): 4-{4-oxo-2-thioxo-5-[1-[5-(4-trifluoromethyl-phenyl)-furan-2-yl]-methylidene]-thiazolidin-3-yl}-cyclohexanecarboxylic acid; $^1$H NMR (400 MHz, DMSO-$d_6$): δ 1.49-1.58 (4H, m), 2.19-2.21 (2H, m), 2.45-2.60 (3H, m), 4.92 (1H, m), 7.40 (1H, d, J=4.0 Hz), 7.52 (1H, d, J=4.0 Hz), 7.58 (1H, s), 7.93-8.05 (4H, m), APCI-MS: 481.0; HPLC: 93%.

(Compound C56): 3-{5-[1-[5-(4-chloro-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.25-1.41 (2H, m), 1.67 (1H, m), 1.87-1.92 (3H, m), 2.29-2.45 (3H, m), 4.96 (1H, m), 7.37 (2H, bs), 7.59 (1H, s), 7.65 (2H, m), 7.86 (2H, m). LC/MS: APCI 447.0, HPLC 100%.

(Compound C57): 4-{5-[1-[5-(4-butoxy-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 0.95 (3H, t, J=7.6 Hz), 1.41-1.57 (6H, m), 1.69-1.76 (2H, m), 2.19-2.22 (2H, m), 2.45-2.60 (3H, m), 4.05 (2H, t, J=6.4 Hz), 4.92 (1H, m), 7.12-7.15 (2H, m), 7.18 (1H, d, J=4.0 Hz), 7.34 (1H, d, J=4.0 Hz), 7.52 (1H, s), 7.77-7.79 (2H, m), APCI-MS: 485.1; HPLC: 99%.

(Compound C58): 3-{5-[5-(4-Methanesulfonyl-phenyl)-furan-2-ylmethylene]-4-oxo-2-thioxo-thiazolidin-3-yl}-cyclohexanecarboxylic acid; $^1$H NMR (400 MHz, DMSO-$d_6$): δ 1.30-1.45 (2H, m), 1.68 (1H, m), 1.90 (3H, m), 2.33 (3H, m), 3.27 (3H, s), 4.96 (1H, m), 7.40 (1H, d, J=4.0 Hz), 7.54 (1H, d, J=4.0 Hz), 7.62 (1H, s), 8.05-8.10 (4H, m). LC/MS: APCI 491.0, HPLC 100%.

(Compound C59): 4-{5-[5-(4-Methanesulfonyl-phenyl)-furan-2-ylmethylene]-4-oxo-2-thioxo-thiazolidin-3-yl}-cyclohexanecarboxylic acid; $^1$H NMR (400 MHz, DMSO-$d_6$): δ 1.50-1.59 (4H, m), 2.20 (2H, m), 2.46 (2H, m), 2.62 (1H, m), 3.27 (3H, s), 4.92 (1H, m), 7.39 (1H, d, J=4.0 Hz), 7.55 (1H, d, J=4.0 Hz), 7.58 (1H, s), 8.05-8.10 (4H, m). LC/MS: APCI 491.0, HPLC 98%.

(Compound C60): 3-{4-oxo-2-thioxo-5-[1-(5-o-tolyl-furan-2-yl)-methylidene]-thiazolidin-3-yl}-cyclohexanecarboxylic acid; $^1$H NMR (400 MHz, DMSO-$d_6$): δ 1.25-1.41 (2H, m), 1.67 (1H, m), 1.87-1.92 (3H, m), 2.29-2.45 (3H, m), 2.69 (3H, s), 4.96 (1H, m), 7.10 (1H, d, J=3.6 Hz), 7.36-7.45 (4H, m), 7.62 (1H, s), 7.80 (1H, d, J=7.6 Hz). LC/MS: APCI 427.0, HPLC 100%.

(Compound C61): 4-{4-oxo-2-thioxo-5-[1-(5-o-tolyl-furan-2-yl)-methylidene]-thiazolidin-3-yl}-cyclohexanecarboxylic acid; $^1$H NMR (400 MHz, DMSO-$d_6$): δ 1.48-1.57 (4H, m), 2.18 (2H, m), 2.38 (3H, s), 2.46 (2H, m), 2.53 (3H, s), 2.61 (1H, m), 4.91 (1H, m), 7.10 (2H, d, J=4 Hz), 7.36-7.45 (4H, m), 7.57 (1H, s), 7.79 (1H, d, J=7.6 Hz). LC/MS: APCI 427.1, HPLC 100%.

(Compound C62): 3-{5-[1-[5-(3-methylsulfanyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.23-1.38 (2H, m), 1.66 (1H, m), 1.87-1.90 (3H, m), 2.25-2.31 (2H, m), 2.58 (3H, s), 2.66 (1H, s), 4.95 (1H, m), 7.31-7.40 (3H, m), 7.48-7.52 (1H, m), 7.60-7.63 (2H, m), 7.70 (1H, m); APCI-MS: 459.0; HPLC: 100%.

(Compound C63): 4-{5-[1-[5-(3-methylsulfanyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.49-1.58 (4H, m), 2.18-2.21 (2H, m), 2.45-2.62 (3H, m), 2.58 (3H, s), 4.91 (1H, m), 7.31-7.33 (1H, m), 7.35-7.40 (2H, m), 7.48-7.52 (1H, m), 7.56 (1H, s), 7.60-7.70 (2H, m); LC/MS: APCI 459.0, HPLC 99%.

(Compound C64): 3-{5-[1-[5-(4-methylsulfanyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.25-1.43 (2H, m), 1.66-1.69 (1H, m), 1.88-1.91 (3H, m), 2.31-2.50 (3H, m), 2.54 (3H, s), 4.98 (1H, m), 7.29 (1H, d, J=4.0 Hz), 7.36 (1H, d, J=4.0 Hz), 7.44-7.46 (2H, m), 7.58 (1H, s), 7.77-7.79 (2H, m), APCI-MS: 459.0; HPLC: 100%.

(Compound C65): 4-{5-[1-[5-(4-methylsulfanyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.50-1.58 (4H, m), 2.18-2.21 (2H, m), 2.45-2.60 (3H, m), 2.54 (3H, s), 4.92 (1H, m), 7.28 (1H, d, J=3.6 Hz), 7.35 (1H, d, J=3.6 Hz), 7.43-7.45 (2H, m), 7.54 (1H, s), 7.77-7.79 (2H, m); APCI-MS: 459.0; HPLC: 93%.

(Compound C66): 3-{5-[5-(4-Isopropoxy-phenyl)-furan-2-ylmethylene]-4-oxo-2-thioxo-thiazolidin-3-yl}-cyclohexanecarboxylic acid; $^1$H NMR (400 MHz, DMSO-$d_6$): δ 1.25-1.31 (1H, m), 1.30 (6H, d, J=6.0 Hz), 1.34-1.41 (1H, m), 1.67-1.70 (1H, m), 1.87-1.92 (3H, m), 2.28-2.45 (3H, m), 4.72 (1H, septet, J=6.0 Hz), 4.95 (1H, m), 7.11 (2H, m), 7.17 (1H, d, J=3.6 Hz), 7.34 (1H, d, J=4.0 Hz), 7.56 (1H, s), 7.77 (2H, m). LC/MS: APCI 471.1, HPLC 99%

(Compound C67): 4-{5-[5-(4-Isopropoxy-phenyl)-furan-2-ylmethylene]-4-oxo-2-thioxo-thiazolidin-3-yl}-cyclohexanecarboxylic acid; $^1$H NMR (400 MHz, DMSO-$d_6$): δ 1.30 (6H, d, J=6.0 Hz), 2.21 (2H, m), 2.47 (2H, m), 2.62 (1H, m), 4.72 (1H, septet, J=6.0 Hz), 4.92 (1H, m), 7.12 (2H, m), 7.17 (1H, d, J=4.0 Hz), 7.34 (1H, d, J=4.0 Hz), 7.52 (1H, s), 7.78 (2H, m). LC/MS: APCI 471.1, HPLC 100%

(Compound C68): 3-{5-[1-(4'-methyl-biphenyl-3-yl)-methylidene]-4-oxo-2-thioxo-thiazolidin-3-yl}cyclohexanecarboxylic acid; $^1$H NMR (400 MHz, DMSO-$d_6$): δ 1.25-1.41 (2H, m), 1.67 (1H, m), 1.87-1.92 (3H, m), 2.29-2.45 (3H, m), 2.72 (3H, s), 4.97 (1H, m), 7.34 (2H, d, J=8 Hz), 7.56-7.65 (4H, m), 7.78-7.89 (3H, m). LC/MS: APCI 437.1, HPLC 93%.

(Compound C69): 4-{5-[1-(4'-methyl-biphenyl-3-yl)-methylidene]-4-oxo-2-thioxo-thiazolidin-3-yl}-cyclohexanecarboxylic acid; $^1$H NMR (400 MHz, DMSO-$d_6$): δ 1.48-1.57 (4H, m), 2.18 (2H, m), 2.36 (3H, s), 2.46 (2H, m), 2.61 (1H, m), 4.91 (1H, m), 7.34 (2H, d, J=8 Hz), 7.57 (1H, d, J=8 Hz), 7.63 (3H, m), 7.79 (2H, m), 7.86 (1H, bs). LC/MS: APCI 437.1, HPLC 100%.

(Compound C70): 3-{5-[1-(5-biphenyl-2-yl-furan-2-yl)-methylidene]-4-oxo-2-thioxo-thiazolidin-3-yl}-cyclohexanecarboxylic acid; $^1$H NMR (400 MHz, DMSO-$d_6$): δ 1.24-1.39 (2H, m), 1.63-1.65 (1H, m), 1.86-1.91 (3H, m), 2.24-2.45 (3H, m), 4.94 (1H, m), 6.02 (1H, d, J=3.6 Hz), 7.15 (1H, d, J=3.6 Hz), 7.28-7.30 (2H, m), 7.37-7.46 (5H, m), 7.52-7.63 (2H, m), 7.86-7.88 (1H, m); LC/MS: APCI 489.1, HPLC 96%.

(Compound C71): 4-{5-[1-(5-biphenyl-2-yl-furan-2-yl)-methylidene]-4-oxo-2-thioxo-thiazolidin-3-yl}-cyclohexanecarboxylic acid; $^1$H NMR (400 MHz, DMSO-$d_6$): δ 1.48-1.55 (4H, m), 2.17-2.20 (2H, m), 2.42-2.61 (3H, m), 4.88 (1H, m), 6.01 (1H, d, J=3.6 Hz), 7.14 (1H, d, J=3.6 Hz), 7.28-7.30 (2H, m), 7.37-7.46 (5H, m), 7.51-7.63 (2H, m), 7.85-7.87 (1H, m); LC/MS: APCI 489.1, HPLC 96%.

(Compound C72): 3-{5-[1-(4'-methyl-biphenyl-4-yl)-methylidene]-4-oxo-2-thioxo-thiazolidin-3-yl}-cyclohexanecarboxylic acid; $^1$H NMR (400 MHz, DMSO-$d_6$): δ 1.25-1.41 (2H, m), 1.67 (1H, m), 1.87-1.92 (3H, m), 2.29-2.45 (3H, m), 2.36 (3H, s), 4.97 (1H, m), 7.32 (2H, d, J=8 Hz), 7.64-7.71 (4H, m), 7.77 (1H, s), 7.86 (2H, d, J=8.4 Hz). LC/MS: APCI 437.1, HPLC 95%.

(Compound C73): 4-{5-[1-(4'-methyl-biphenyl-4-yl)-methylidene]-4-oxo-2-thioxo-thiazolidin-3-yl}-cyclohexanecarboxylic acid; $^1$H NMR (400 MHz, DMSO-$d_6$): δ 1.48-1.57 (4H, m), 2.18 (2H, m), 2.36 (3H, s), 2.46 (2H, m), 2.61 (1H, m), 4.91 (1H, m), 7.32 (2H, d, J=8.4 Hz), 7.65-7.69 (4H, m), 7.73 (1H, s), 7.86 (2H, d, J=8 Hz). LC/MS: APCI 437.1, HPLC 94%.

(Compound C74): 3-{5-[5-(2-Methoxy-5-methyl-phenyl)-furan-2-ylmethylene]-4-oxo-2-thioxo-thiazolidin-3-yl}-cyclohexanecarboxylic acid; $^1$H NMR (400 MHz, DMSO-$d_6$): δ 1.25-1.31 (1H, m), 1.34-1.41 (1H, m), 1.67-1.70 (1H, m), 1.87-1.92 (3H, m), 2.28-2.45 (6H, m), 3.92 (3H, s), 4.95 (1H, m), 7.09 (1H, d, J=8.8 Hz), 7.18 (1H, d, J=4.0 Hz), 7.24 (1H, dd, J=8.4 Hz, 2.0 Hz), 7.34 (1H, d, J=4.0 hz), 7.58 (1H, s), 7.62 (1H, d, 2.0 Hz). LC/MS: APCI 457.1, HPLC 100%.

(Compound C75): 4-{5-[5-(2-Methoxy-5-methyl-phenyl)-furan-2-ylmethylene]-4-oxo-2-thioxo-thiazolidin-3-yl}-cyclohexanecarboxylic acid; $^1$H NMR (400 MHz, DMSO-$d_6$): δ 1.50-1.58 (4H, m), 2.20 (2H, m), 2.35 (3H, s), 2.46 (2H, m), 2.63 (1H, m), 3.92 (3H, s), 4.89 (1H, m), 7.09 (1H, d, J=8.4 Hz), 7.17 (1H, d, J=4.0 Hz), 7.24 (1H, dd, J=8.8 Hz, 2.0 Hz), 7.32 (1H, d, J=4.0 Hz), 7.53 (1H, s), 7.61 (1H, d, J=2.0 Hz). LC/MS: APCI 457.0, HPLC 100%.

(Compound C76): 4-{5-[1-[5-(4-acetylamino-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 1.49-1.57 (4H, m), 2.08 (3H, s), 2.18-2.22 (2H, m), 2.45-2.60 (3H, m), 4.92 (1H, m), 7.21 (1H, d, J=3.6 Hz), 7.35 (1H, d, J=3.6 Hz), 7.52 (1H, s), 7.77-7.78 (4H, m); APCI-MS: 470.0; HPLC: 100%.

(Compound C77): 3-{5-[1-[5-(4-butyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 0.91 (3H, t, J=7.6 Hz), 1.25-1.41 (4H, m), 1.55-1.69 (3H, m), 1.87-1.92 (3H, m), 2.29-2.45 (3H, m), 2.66 (2H, t, J=7.6 Hz), 4.97 (1H, m), 7.28 (1H, d, J=3.6 Hz), 7.36-7.40 (3H, m), 7.59 (1H, s), 7.78 (2H, d, J=8 Hz). LC/MS: APCI 469.1, HPLC 100%.

(Compound C78): 4-{5-[1-[5-(4-butyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 0.91 (3H, t, J=7.2 Hz), 1.29-1.35 (2H, m), 1.48-1.57 (6H, m), 2.18 (2H, m), 2.46 (2H, m), 2.65 (4H, m), 4.91 (1H, m), 7.27 (1H, d, J=4 Hz), 7.36 (1H, d, J=3.6 Hz), 7.40 (2H, d, J=8 Hz), 7.54 (1H, s), 7.77 (2H, d, J=8 Hz). LC/MS: APCI 469.0, HPLC 100%.

(Compound C79): 3-{5-[1-[5-(4-propyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 0.91 (3H, t, J=7.6 Hz), 1.25-1.41 (2H, m), 1.55-1.69 (3H, m), 1.87-1.92 (3H, m), 2.29-2.45 (3H, m), 2.62 (2H, t, J=7.6 Hz), 4.97 (1H, m), 7.28 (1H, d, J=3.6 Hz), 7.36-7.40 (3H, m), 7.59 (1H, s), 7.78 (2H, d, J=8 Hz). LC/MS: APCI 455.1.

(Compound C80): 4-{5-[1-[5-(4-propyl-phenyl)-furan-2-yl]-methylidene]-4-oxo-2-thioxo-thiazolidin-3-yl}-cyclohexanecarboxylic acid; $^1$H NMR (400 MHz, DMSO-$d_6$): δ 0.91 (3H, t, J=7.2 Hz), 1.48-1.57 (6H, m), 2.18 (2H, m), 2.46 (2H, m), 2.65 (4H, m), 4.92 (1H, m), 7.28 (1H, d, J=4 Hz), 7.36 (1H, d, J=3.6 Hz), 7.40 (2H, d, J=8 Hz), 7.54 (1H, s), 7.77 (2H, d, J=8.4 Hz). LC/MS: APCI 455.1, HPLC 100%.

(Compound C83): 3-{5-[5-(4-Methylsulfamoyl-phenyl)-furan-2-ylmethylene]-4-oxo-2-thioxo-thiazolidin-3-yl}-cyclohexanecarboxylic acid; $^1$H NMR (400 MHz, DMSO-$d_6$): δ 1.25-1.31 (1H, m), 1.34-1.41 (1H, m), 1.67-170 (1H, m), 1.87-1.92 (3H, m), 2.28-2.45 (3H, m), 2.46 (3H, s) 4.97 (1H, m), 7.40 (1H, d, J=4.0 Hz), 7.50 (1H, d, J=4.0 Hz), 7.62 (1H, s), 7.93 (2H, m), 8.04 (2H, m). LC/MS: APCI 506.0, HPLC 100%.

(Compound C84): 4-{5-[5-(4-Methylsulfamoyl-phenyl)-furan-2-ylmethylene]-4-oxo-2-thioxo-thiazolidin-3-yl}-cyclohexanecarboxylic acid; $^1$H NMR (400 MHz, DMSO-d$_6$): δ 1.50-1.58 (4H, m), 2.20 (2H, m), 2.46 (5H, m), 2.63 (1H, m), 4.89 (1H, m), 7.39 (1H, d, J=4.0 Hz), 7.50 (1H, d, J=4.0 Hz), 7.55 (1H, quartet, J=6.0 Hz), 7.58 (1H, s), 7.94 (2H, m), 8.04 (2H, m), 12.2 (1H, bs). LC/MS. APCI 506.0, HPLC 99%.

(Compound C85): 3-{5-[5-(4-Dimethylsulfamoyl-phenyl)-furan-2-ylmethylene]-4-oxo-2-thioxo-thiazolidin-3-yl}-cyclohexanecarboxylic acid; $^1$H NMR (400 MHz, DMSO-d$_6$): δ 1.25-1.31 (1H, m), 1.34-1.41 (1H, m), 1.67-1.70 (1H, m), 1.87-1.92 (3H, m), 2.28-2.45 (3H, m), 2.65 (6H, s), 4.96 (1H, m), 7.40 (1H, d, J=4.0 Hz), 7.53 (1H, d, J=4.0 Hz), 7.62 (1H, s), 7.92 (2H, m), 8.07 (2H, m). LC/MS: APCI 520.0, HPLC 99%.

(Compound C86): 4-{5-[5-(4-Dimethylsulfamoyl-phenyl)-furan-2-ylmethylene]-4-oxo-2-thioxo-thiazolidin-3-yl}-cyclohexanecarboxylic acid; $^1$H NMR (400 MHz, DMSO-d$_6$): δ 1.50-1.58 (4H, m), 2.20 (2H, m), 2.46 (2H, m), 2.63 (7H, m), 4.89 (1H, m), 7.40 (1H, d, J=3.6 Hz), 7.54 (1H, d, J=4.0 Hz), 7.58 (1H, s), 7.93 (2H, m), 8.06 (2H, m), 12.2 (1 h, bs). LC/MS: APCI 520.1, HPLC 100%.

General Procedure for the Synthesis Appropriately Substituted 2-(4-oxo-2-thioxo-thiazolidin-3-ylamino)-benzoic acid:

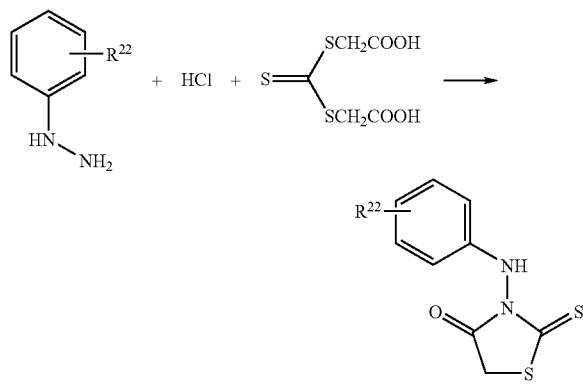

To an aqueous (20 mL) solution of appropriately substituted hydrazino-benzoic acid hydrochloride (13.30 mmol) was added aqueous sodium hydroxide (126.60 mmol) followed by bis(carboxymethyl)trithiocarbonate (13.28 mmol). The mixture was stirred at reflux temperature for 10 h, cooled to room temperature and stirred for 50 h. The solid product was filtered off and washed on funnel successively with water (2×10 ml), ether (5 mL) and hexane (20 mL). The material was dried in a vacuum oven at 80° C. for 5 h to afford appropriately substituted-(4-oxo-2-thioxo-thiazolidin-3-ylamino)-benzoic acid.

2-(4-oxo-2-thioxo-thiazolidin-3-ylamino)-benzoic acid: $^1$H NMR (400 MHz, DMSO-d$_6$): δ 4.33 (1H, bs), 6.66 (1H, m), 6.90 (1H, m), 7.40 (1H, m), 7.89 (1H, m), 13.37 (1H, bs). ESI-MS: 267.0

3-(4-oxo-2-thioxo-thiazolidin-3-ylamino)-benzoic acid: $^1$H NMR (400 MHz, DMSO-d$_6$): δ 4.33 (1H, bs), 6.66 (1H, m), 6.90 (1H, m), 7.40 (1H, m), 7.89 (1H, m), 13.37 (1H, bs). ESI-MS: 267.0

4-(4-oxo-2-thioxo-thiazolidin-3-ylamino)-benzoic acid: $^1$H NMR (400 MHz, DMSO-d$_6$): δ 4.33 (1H, bs), 6.66 (1H, m), 6.90 (1H, m), 7.40 (1H, m), 7.89 (1H, m), 13.37 (1H, bs). ESI-MS: 267.0

General Procedure for the Synthesis of Compounds Listed in Table 4 (Compounds D1 to D60):

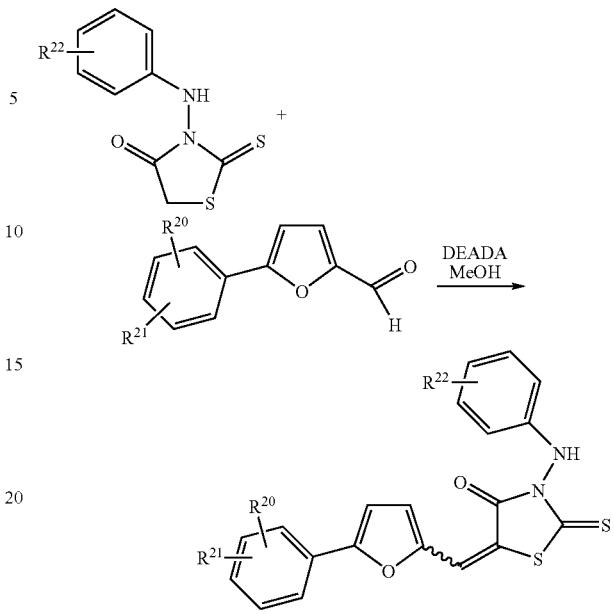

A mixture of appropriately substituted 4-oxo-2-thioxo-thiazolidin-3-ylamino-benzoic acid (0.29 mmol), appropriately substituted-(5-phenyl)-furan-2-carbaldehyde and (0.31 mmol) and ethylenediamine diacetate (0.031 mmol) in methanol (10 mL) was stirred at room temperature for 18 h. The reaction mixture was poured into stirred 0.6 N aq sodium hydrogensulfite (50 mL). The mixture was vigorously stirred for 30 min. The solid product was filtered off and washed on funnel successively with 0.6 N aq sodium hydrogensulfite (1 mL), water (2×2 mL), ether (2×1 mL) and hexanes (2 mL). The material was dried in vacuum oven at 65 deg C. for 17 h to afford desired target compound.

(Compound D1): 2-{5-[1-[5-(2-chloro-phenyl)-furan-2-yl]-methylidene]-4-oxo-2-thioxo-thiazolidin-3-ylamino}-benzoic acid; $^1$H NMR (400 MHz, DMSO-d$_6$): δ 6.55 (1H, d, J=8.0 Hz), 6.87 (1H, t, J=7.6 Hz), 7.32 (1H, t, J=7.6 Hz), 7.44-7.51 (3H, m), 7.62 (1H, d, J=8.0 Hz), 7.66 (1H, d, J=8.4 Hz), 7.80 (1H, s), 7.91 (1H, d, J=8.0 Hz), 7.97 (1H, d, J=8.0 Hz). LC/MS. APCI 457.2, HPLC 97.9%

(Compound D2): 2-{5-[1-[5-(4-tert-butyl-phenyl)-furan-2-yl]-meth-(E)-ylidene]-4-oxo-2-thioxo-thiazolidin-3-ylamino}-benzoic acid; $^1$H NMR (400 MHz, DMSO-d$_6$): δ 1.32 (9H, s), 6.45 (1H, m), 6.82 (1H, m), 7.23 (1H, m), 7.30 (1H, d, J=3.6), 7.40 (1H, d, J=3.6), 7.61 (2H, m), 7.74 (1H, s), 7.82 (2H, m), 7.91 (1H, m), 11.20 (1H, bs). LC/MS: APCI 477.9, HPLC 91.0%

(Compound D3): 2-{4-oxo-2-thioxo-5-[1-[5-(3-trifluoromethyl-phenyl)-furan-2-yl]-methylidene]-thiazolidin-3-ylamino}-benzoic acid; $^1$H NMR (400 MHz, DMSO-d$_6$): δ 6.53 (1H, m), 6.86 (1H, m), 7.29 (1H, m), 7.43 (1H, d, J=3.6 Hz), 7.59 (1H, d, J=3.6 Hz), 7.78 (1H, s), 7.82 (2H, m), 7.92 (1H, m), 8.16 (1H, m), 8.21 (1H, m). LC/MS: APCI 489.3, HPLC 97.1%

(Compound D4): 2-{5-[1-[5-(3-nitro-phenyl)-furan-2-yl]-methylidene]-4-oxo-2-thioxo-thiazolidin-3-ylamino}-benzoic acid; $^1$H NMR (400 MHz, DMSO-d$_6$): δ 6.62 (1H, m), 6.90 (1H, m), 7.37 (1H, m), 7.44 (1H, d, J=3.6 Hz), 7.64 (1H, d, J=3.6 Hz), 7.80 (1H, s), 7.88 (1H, m), 7.92 (1H, m), 8.28 (2H, m), 8.65 (1H, m), 10.2 (1H, bs). LC/MS: APCI 466.7, HPLC 96.5%

(Compound D5): 2-{5-[1-[5-(5-tert-butyl-2-hydroxy-phenyl)-furan-2-yl]-methylidene]-4-oxo-2-thioxo-thiazolidin-3-ylamino}-benzoic acid; $^1$H NMR (400 MHz, DMSO-d$_6$): δ 1.37 (9H, s), 6.98 (1H, d, J=8.4 Hz), 7.23 (1H, d, J=3.6 Hz), 7.34 (1H, dd, J=8.8, 2.8 Hz), 7.39 (1H, d, J=3.6 Hz), 7.70 (2H, m), 7.74 (1H, s), 7.94 (1H, d, J=2.4 Hz), 8.01 (1H, m), 8.07 (1H, m). LC/MS: APCI 493.1, HPLC 100%.

(Example D6): 2-{5-[1-[5-(4-morpholin-4-yl-phenyl)-furan-2-yl]-meth-(E)-ylidene]-4-oxo-2-thioxo-thiazolidin-3-ylamino}-benzoic acid; $^1$H NMR (400 MHz, DMSO-d$_6$): δ 3.26 (2H, dd, J=5.2, 3.6 Hz), 3.87 (2H, dd, J=5.2, 3.6 Hz), 6.69 (1H, d, J=4.0 Hz), 6.93 (2H, m), 7.26 (1H, s), 7.30 (1H, d, J=4.0), 7.74 (2H, m), 9.58 (1H, s). ESI-MS: 258.0.

(Compound D7): 2-{5-[1-[5-(2,4-difluoro-phenyl)-furan-2-yl]-methylidene]-4-oxo-2-thioxo-thiazolidin-3-ylamino}-benzoic acid; $^1$H NMR (400 MHz, DMSO-d$_6$): δ 6.58 (1H, d, J=8 Hz), 6.87 (1H, t, J=7.2 Hz), 7.18 (1H, m), 7.32 (1H, m), 7.41 (2H, m), 7.53 (1H, m), 7.80 (1H, s), 7.96 (2H, m). LC/MS: APCI 457.0, HPLC 95%.

(Compound D8): 2-{5-[1-[5-(2,4-dimethyl-phenyl)-furan-2-yl]-methylidene]-4-oxo-2-thioxo-thiazolidin-3-ylamino}-benzoic acid; $^1$H NMR (400 MHz, DMSO-d$_6$): δ 2.35 (3H, s), 2.52 (3H, s), 6.57 (1H, d, J=8.4 Hz 0, 6.87 (1H, t, J=7.2 Hz), 7.08 (1H, d, J=3.6 Hz), 7.22 (1H, bs), 7.27 (1H, d, J=8.4 Hz), 7.34 (1H, m), 7.44 (1H, d, J=3.6 Hz), 7.74 (1H, d, J=7.6 Hz), 7.77 (1H, s), 7.92 (1H, m). LC/MS APCI 449.0, HPLC 95%.

(Compound D9): 2-{5-[1-[5-(4-methoxy-2-methyl-phenyl)-furan-2-yl]-methylidene]-4-oxo-2-thioxo-thiazolidin-3-ylamino}-benzoic acid; $^1$H NMR (400 MHz, DMSO-d$_6$): δ 2.52 (3H, s), 3.83 (3H, s), 6.36 (1H, d, J=8.4 Hz), 6.78 (1H, t, J=7.6 Hz), 6.99 (2H, m), 7.05 (1H, dd, J=2.4 & 8.8 Hz), 7.13 (1H, m), 7.42 (1H, d, J=3.6 Hz), 7.72 (1H, s), 7.79 (1H, d, J=8.8 Hz), 7.89 (1H, m). LC/MS: APCI 465.0, HPLC 80%.

(Compound D10): 2-{5-[1-[5-(4-fluoro-2-methyl-phenyl)-furan-2-yl]-methylidene]-4-oxo-2-thioxo-thiazolidin-3-ylamino}-benzoic acid; $^1$H NMR (400 MHz, DMSO-d$_6$): δ 2.56 (3H, s), 6.44 (1H, d, J=8 Hz), 6.81 (1H, t, J=7.2 Hz), 7.11 (1H, d, J=4 Hz), 7.24 (1H, m), 7.32 (2H, m), 7.44 (1H, d, J=3.6 Hz), 7.76 (1H, s), 7.84 (1H, m), 7.91 (1H, m). LC/MS: APCI 453.0, HPLC 95%.

(Compound D11): 2-{5-[1-[5-(2-fluoro-4-methyl-phenyl)-furan-2-yl]-methylidene]-4-oxo-2-thioxo-thiazolidin-3-ylamino}-benzoic acid; $^1$H NMR (400 MHz, DMSO-d$_6$): δ 2.38 (3H, s), 6.49 (1H, d, J=7.6 Hz), 6.84 (1H, t, J=7.6 Hz), 7.15 (1H, t, J=3.2 Hz), 7.31 (3H, m), 7.43 91H, d, J=3.6 Hz), 7.78 (1H, s), 7.81 (1H, m), 7.90 (1H, m). LC/MS: APCI 453.0, HPLC 94%.

(Compound D12): 2-{5-[1-[5-(2-Hydroxy-phenyl)-furan-2-yl]-methylidene]-4-oxo-2-thioxo-thiazolidin-3-ylamino}-benzoic acid; $^1$H NMR (400 MHz, DMSO-d$_6$): δ 6.54 (1H, d, J=8.4 Hz), 6.96 (1H, m), 7.09 (2H, m), 7.29 (3H, m), 7.42 (1H, d, J=3.6 Hz), 7.77 (1H, s), 7.82 (1H, m), 7.92 (1H, m). LC/MS: APCI 437.0, HPLC 97%.

(Compound D13): 2-{4-oxo-2-thioxo-5-[1-(5-p-tolyl-furan-2-yl)-methylidene]-thiazolidin-3-ylamino}-benzoic acid; $^1$H NMR (400 MHz, DMSO-d$_6$): δ 2.38 (3H, s), 6.60 (1H, d, J=8.4 Hz), 6.90 (1H, t, J=7.6 Hz), 7.31 (1H, d, J=3.6 Hz), 7.36-7.42 (4H, m), 7.76-7.80 (3H, m), 7.92 (1H, dd, J=8.0, 1.6 Hz). LC/MS: APCI 435.0, HPLC 87%.

(Compound D14): 2-{5-[1-[5-(4-methoxy-phenyl)-furan-2-yl]-methylidene]-4-oxo-2-thioxo-thiazolidin-3-ylamino}-benzoic acid; $^1$H NMR (400 MHz, DMSO-d$_6$): δ 3.84 (3H, s), 6.58 (1H, d, J=8.0 Hz), 6.89 (1H, t, J=7.6 Hz), 7.16-7.18 (2H, m), 7.24 (1H, d, J=3.6 Hz), 7.36 (1H, t, J=7.0 Hz), 7.41 (1H, d, J=4 Hz), 7.74 (1H, s), 7.83-7.86 (2H, m), 7.92 (1H, dd, J=8.0, 1.6 Hz). LC/MS: APCI 451.0, HPLC 91%.

(Compound C15): 2-[4-Oxo-2-thioxo-5-(6-o-tolyl-pyridin-2-ylmethylene)-thiazolidin-3-ylamino]-benzoic acid; $^1$H NMR (400 MHz, DMSO-d$_6$): δ 2.39 (3H, s), 6.51 (1H, d, J=8.4 Hz), 6.65 (1H, t, J=6.8 Hz), 7.29 (1H, m), 7.41 (1H, m), 7.52 (1H, m), 7.61 (1H, d, J=8.4 Hz), 7.92 (1H, m), 7.97 (1H, m), 8.08 (1H t, J=8.0 Hz). LC/MS APCI 446.0, HPLC 76%.

(Compound D16): 3-{5-[1-[5-(2-chloro-phenyl)-furan-2-yl]-methylidene]-4-oxo-2-thioxo-thiazolidin-3-ylamino}-benzoic acid; $^1$H NMR (400 MHz, DMSO-d$_6$): δ 6.87 (1H, m), 7.24 (3H, m), 7.39 (1H, m), 7.50 (3H, m), 7.66 (2H, m), 7.85 (1H, s), 8.00 (1H, m), 9.30 (1H, bs). LC/MS: APCI 455.9, HPLC 100%.

(Compound D17): 3-{5-[1-[5-(3-trifluoromethyl-phenyl)-furan-2-yl]-methylidene]-4-oxo-2-thioxo-thiazolidin-3-ylamino}-benzoic acid; $^1$H NMR (400 MHz, DMSO-d$_6$): δ 6.90 (1H, m), 7.25 (1H, m), 7.30 (1H, m), 7.41 (1H, m), 7.47 (1H, m), 7.62 (1H, m), 7.84 (3H, m), 8.19 91H, d, J=7.2 Hz), 8.23 (1H, s), 9.36 (1H, bs). LC/MS: APCI 490.0, HPLC 100%.

(Compound D18): 3-{5-[1-[5-(4-chloro-phenyl)-furan-2-yl]-methylidene]-4-oxo-2-thioxo-thiazolidin-3-ylamino}-benzoic acid; $^1$H NMR (400 MHz, DMSO-d$_6$): δ 6.92 (1H, m), 7.24 (1H, m), 7.30 (1H, m), 7.44 (3H, m), 7.68 (2H, m), 7.82 91H, s), 7.92 (2H, m), 9.36 (1H, bs). LC/MS: APCI 455.9, HPLC 92%.

(Compound D19): 2-{5-[1-[5-(2,4-dimethoxy-phenyl)-furan-2-yl]-methylidene]-4-oxo-2-thioxo-thiazolidin-3-ylamino}-benzoic acid; $^1$H NMR (400 MHz, DMSO-d$_6$): δ 3.87 (3H, s), 3.97 (3H, s), 6.56 (1H, d, J=8.0 Hz), 6.76 (1H, d, J=2.4 Hz), 6.86-6.90 (2H, m), 7.11 (1H, d, J=3.6), 7.33-7.37 (1H, m), 7.40 (1H, d, J=4.0 Hz), 7.74 (1H, s), 7.82 (1H, d, J=8.8 Hz), 7.91 (1H, dd, J=8.0 Hz, 1.6 Hz), LC/MS: APCI 481.0, HPLC 99%.

(Compound D20): 4-{5-[5-(2-Chloro-phenyl)-furan-2-yl-methylene]-4-oxo-2-thioxo-thiazolidin-3-ylamino}-benzoic acid, $^1$H NMR (400 MHz, DMSO-d$_6$): δ 6.76 (2H, m), 7.50 (3H, m), 7.64 (m, 2H), 7.78 (2H, m), 7.85 (1H, s), 7.98 (1H, dd, J=8.0 Hz, 1.6 Hz), 9.66 (1H, bs). LC/MS: APCI 456.0, HPLC 100%.

(Compound D21): 4-{5-[5-(4-Chloro-phenyl)-furan-2-yl-methylene]-4-oxo-2-thioxo-thiazolidin-3-ylamino}-benzoic acid, $^1$H NMR (400 MHz, DMSO-d$_6$): δ 6.76 (2H, m), 7.44 (2H, m), 7.67 (2H, m), 7.78 (2H, m), 7.81 (1H, s), 9.67 (1H, bs), 12.42 (1H, bs). LC/MS: APCI 456.0, HPLC 100%.

(Compound D22): 2-{5-[5-(1H-Indol-5-yl)-furan-2-ylmethylene]-4-oxo-2-thioxo-thiazolidin-3-ylamino}-benzoic acid; $^1$H NMR (400 MHz, DMSO-d$_6$): δ 6.61 (2H, m), 6.91 (1H, m), 7.26 (1H, d, J=4.0 Hz), 7.40 (1H, m), 7.44 (1H, d, J=4.0 Hz), 7.47 (1H, m), 7.59 (1H, d, J=8.4 Hz), 7.67 (1H, dd, J=8.4 Hz, 1.6 Hz), 7.76 (1H, s), 7.93 (1H, dd, J=8.0 Hz, 1.6 Hz), 8.13 (1H, d, J=1.6 Hz), 9.94 (1H, bs), 11.43 (1H, bs). LC/MS: APCI 460.0, HPLC 100%.

(Compound D23): 2-{5-[1-[5-(4-chloro-2-methyl-phenyl)-furan-2-yl]-methylidene]-4-oxo-2-thioxo-thiazolidin-3-ylamino}-benzoic acid; $^1$H NMR (400 MHz, DMSO-d$_6$): δ 2.56 (3H, s), 6.60 (1H, d, J=8.4 Hz), 6.90 (1H, t, J=7.6 Hz), 7.17 (1H, d, J=4.0 Hz), 7.35-7.40 (1H, m), 7.45 (1H, d, J=4.0 Hz), 7.53-7.56 (2H, m), 7.79 (1H, s), 7.83 (1H, d, J=8.4 Hz), 7.92 (1H, dd, J=8.0 Hz, 1.6 Hz), LC/MS: APCI 469.0, HPLC 100%.

(Compound D24): 2-{5-[5-(2,6-Dimethyl-phenyl)-furan-2-ylmethylene]-4-oxo-2-thioxo-thiazolidin-3-ylamino}-benzoic acid; $^1$H NMR (400 MHz, DMSO-d$_6$): δ 2.26 (6H, s), 6.43 (1H, d, J=7.2 Hz), 6.80 (1H, m), 6.92 (1H, d, J=3.6 Hz), 7.22 (3H, m), 7.32 (1H, m), 7.43 (1H, d, J=3.6 Hz), 7.77 (1H, s), 7.89 (1H, dd, J=7.6 Hz, 1.6 Hz). LC/MS: APCI 449.0, HPLC 100%.

(Compound D25): 2-{5-[1-[5-(4-fluoro-2-methoxy-phenyl)-furan-2-yl]-methylidene]-4-oxo-2-thioxo-thiazolidin-3-ylamino}-benzoic acid; $^1$H NMR (400 MHz, DMSO-d$_6$): δ 3.99 (3H, s), 6.50 (1H, d, J=8.0 Hz), 6.84 (1H, t, J=7.6 Hz), 7.10-7.18 (2H, m), 7.20 (1H, d, J=4.0 Hz), 7.28 (1H, t, J=8.4 Hz), 7.41 (1H, d, J=3.6 Hz), 7.76 (1H, s), 7.86-7.92 (2H, m), LC/MS: APCI 469.0, HPLC 94%.

(Compound D26): 2-{5-[1-[5-(3-fluoro-4-methoxy-phenyl)-furan-2-yl]-methylidene]-4-oxo-2-thioxo-thiazolidin-3-ylamino}-benzoic acid; $^1$H NMR (400 MHz, DMSO-d$_6$): δ 3.92 (3H, s), 6.57 (1H, d, J=8.4 Hz), 6.88 (1H, t, J=7.6 Hz), 7.31 (1H, d, J=4.0 Hz), 7.33-7.37 (1H, m), 7.40 (1H, d, J=3.6 Hz), 7.44 (1H, t, J=8.0 Hz), 7.68 (1H, d, J=8.8 Hz), 7.68-7.77 (2H, m), 7.92 (1H, dd, J=7.6 Hz, 1.6 Hz), LC/MS: APCI 469.0, HPLC 95%.

(Compound D27): 2-{5-[1-[5-(2-benzyloxy-phenyl)-furan-2-yl]-methylidene]-4-oxo-2-thioxo-thiazolidin-3-ylamino}-benzoic acid; $^1$H NMR (400 MHz, DMSO-d$_6$): δ 5.34 (2H, s), 6.48 (1H, d, J=8.4 Hz), 6.82 (1H, t, J=7.6 Hz), 7.15 (1H, d, J=3.6 Hz), 7.25 (2H, m), 7.34 (1H, d, J=8 Hz), 7.39 (2H, m), 7.45 (3H, m), 7.54 (3H, m), 7.73 (1H, s), 7.91 (2H, m). LC/MS: APCI 527.1, HPLC 85%.

(Compound D28): 2-{4-Oxo-2-thioxo-5-[5-(2,4,6-trimethyl-phenyl)-furan-2-ylmethylene]-thiazolidin-3-ylamino}-benzoic acid; $^1$H NMR (400 MHz, DMSO-d$_6$): δ 2.23 (6H, s), 2.31 (3H, s), 6.21 (1H, d, J=8.4 Hz), 6.90 (2H, m), 7.04 (2H, s), 7.38 (1H, m), 7.43 (1H, d, J=7.6 Hz), 7.78 (1H, s), 7.91 (1H, dd, J=7.6 Hz, 1.4 Hz), 9.85 (1H, s), 13.30 (1H, bs). LC/MS: APCI 463.0, HPLC 95%.

(Compound D29): 2-{5-[5-(4-Dimethylamino-2-methyl-phenyl)-furan-2-ylmethylene]-4-oxo-2-thioxo-thiazolidin-3-ylamino}-benzoic acid; $^1$H NMR (400 MHz, DMSO-d$_6$): δ 2.50 (3H, s), 3.00 (6H, s), 6.42 (1H, d, J=8.4 Hz), 6.68 (1H, m), 6.81 (2H, m), 6.88 (1H, d, J=3.6 Hz), 7.22 (1H, m), 7.40 (1H, d, J=3.6 Hz), 7.69 (1H, d, J=4.0 Hz), 7.71 (1H, s), 7.91 (1H, dd, J=4 Hz, 1.6 Hz). LC/MS: APCI 478.0, HPLC 95%.

(Compound D30): 2-{5-[1-[5-(2-methylsulfanyl-phenyl)-furan-2-yl]-methylidene]-4-oxo-2-thioxo-thiazolidin-3-ylamino}-benzoic acid; $^1$H NMR (400 MHz, DMSO-d$_6$): δ 2.58 (3H, s), 6.53 (1H, d, J=8.0 Hz), 6.86 (1H, t, J=7.6 Hz), 7.29 (1H, d, J=3.6 Hz), 7.31-7.33 (1H, m), 7.39-7.43 (1H, m), 7.44 (1H, d, J=4.0 Hz), 7.47-7.49 (2H, m), 7.79 (1H, s), 7.82 (1H, d, J=7.6 Hz), 7.91 (1H, dd, J=7.6 Hz, 1.6 Hz), LC/MS: APCI 467.0, HPLC 89%.

(Compound D31): 2-{5-[5-(4-Dimethylamino-phenyl)-furan-2-ylmethylene]-4-oxo-2-thioxo-thiazolidin-3-ylamino}-benzoic acid; $^1$H NMR (400 MHz, DMSO-d$_6$): δ 3.01 (6H, s), 6.56 (1H, d, J=8.4 Hz), 6.89 (3H, m), 7.10 (1H, d, J=4.0 Hz), 7.35 (1H, m), 7.40 (1H, d, J=4.0 Hz), 7.69 (1H, s), 7.73 (2H, m), 7.92 (1H, dd, J=8.4 Hz, 1.6 Hz), 10.10 (1H, bs). LC/MS: APCI 464.0, HPLC 92%.

(Compound D32): 2-{5-[2-(2-Chloro-benzyloxy)-benzylidene]-4-oxo-2-thioxo-thiazolidin-3-ylamino}-benzoic acid; $^1$H NMR (400 MHz, DMSO-d$_6$): δ 5.34 (2H, s), 6.43 (1H, d, J=8.4 Hz), 6.80 (1H, m), 7.19 (2H, m), 7.32 (1H, d, J=8.4 Hz), 7.40 (2H, m), 7.54 (3H, m), 7.60 (1H, m), 7.89 (1H, dd, J=7.6 Hz, 1.6 Hz), 8.04 (1H, s). LC/MS: APCI 448.5, HPLC 86%.

(Compound D33): 2-{4-oxo-5-[1-[5-(2-phenoxy-phenyl)-furan-2-yl]-methylidene]-2-thioxo-thiazolidin-3-ylamino}-benzoic acid, $^1$H NMR (400 MHz, DMSO-d$_6$): δ 6.56 (1H, d, J=8.4 Hz), 6.87 (1H, t, J=8.0 Hz), 7.02-7.04 (1H, m), 7.08-7.10 (2H, m), 7.17-7.21 (2H, m), 7.33 (1H, t, J=8.4 Hz), 7.38-7.48 (5H, m), 7.78 (1H, s), 7.91 (1H, dd, J=7.6 Hz, 1.6 Hz), 8.00-8.03 (1H, m), LC/MS: APCI 513.0, HPLC 82%.

(Compound D34): 2-{4-oxo-2-thioxo-5-[1-(5-o-tolyl-thiophen-2-yl)-methylidene]-thiazolidin-3-ylamino}-benzoic acid; $^1$H NMR (400 MHz, DMSO-d$_6$): δ 2.47 (3H, s), 6.48 (1H, d, J=8 Hz), 6.81 (1H, t, J=8 Hz), 7.23 (1H, t, J=6.8 Hz), 7.35 (3H, m), 7.48 (1H, m), 7.54 (1H, m), 7.88 (2H, m), 8.18 (1H, s). LC/MS: APCI 451.0, HPLC 90%.

(Compound D35): 2-{4-oxo-2-thioxo-5-[1-(5-2-chloro-thiophen-2-yl)-methylidene]-thiazolidin-3-ylamino}-benzoic acid; $^1$H NMR (400 MHz, DMSO-d$_6$): δ 6.52 (1H, d, J=8.4 Hz), 6.83 91H, t, J=7.6 Hz), 7.26 (1H, t, J=8.4 Hz), 7.47 (2H, m), 7.50 (1H, m), 7.65 (1H, m), 7.80 (1H, m), 7.92 (2H, m), 8.19 (1H, s). LC/MS: APCI 470.9, HPLC 96%.

(Compound D36): 2-{4-oxo-2-thioxo-5-[1-(5-2-fluoro-thiophen-2-yl)-methylidene]-thiazolidin-3-ylamino}-benzoic acid; $^1$H NMR (400 MHz, DMSO-d$_6$): δ 6.56 (1H, d, J=8.4 Hz), 6.85 (1H, t, J=8 Hz), 7.27-7.50 (4H, m), 7.84-7.99 (4H, m), 8.19 (1H, s). LC/MS: APCI 455.0, HPLC 90%.

(Compound D37): 4-{4-oxo-2-thioxo-5-[5-(3-trifluoromethyl-phenyl)-furan-2-ylmethylene]-thiazolidin-3-ylamino}-benzoic acid; $^1$H NMR (400 MHz, DMSO-d$_6$): δ 6.77 (2H, m), 7.46 (1H, d, J=4.0 Hz), 7.61 (1H, d, 3.6 Hz), 7.79 (2H, m), 7.83 (2H, m), 7.84 (1H, s), 8.17 (1H, d, J=7.2 Hz), 8.22 (1H, s), 9.65 (1H, bs). LC/MS: APCI 490.0, HPLC 97%.

(Compound D38): 2-{5-[1-[5-(4-ethyl-phenyl)-furan-2-yl]-methylidene]-4-oxo-2-thioxo-thiazolidin-3-ylamino}-benzoic acid; $^1$H NMR (400 MHz, DMSO-d$_6$): δ 1.22 (3H, t, J=7.6 Hz), 2.67 (2H, q), 6.43 (1H, d, J=8.4 Hz), 6.79 (1H, m), 7.21 (1H, m), 7.31 (1H, d, J=3.6 Hz), 7.44 (3H, m), 7.73 (1H, s), 7.82 (2H, d, J=8.4 Hz), 7.91 91H, m). LC/MS: APCI 449.0, HPLC 97%.

(Compound D39): 2-{4-oxo-2-thioxo-5-[1-[5-(4-trifluoromethyl-phenyl)-furan-2-yl]-methylidene]-thiazolidin-3-ylamino}-benzoic acid; $^1$H NMR (400 MHz, DMSO-d$_6$): δ 6.50 (1H, d, J=8.0 Hz), 6.83 (1H, t, J=7.2 Hz), 7.26 (1H, t, J=6.8 Hz), 7.44 (1H, d, J=4.0 Hz), 7.56 (1H, d, J=3.6 Hz), 7.79 (1H, s), 7.90 (1H, dd, J=8.0 Hz, 1.6 Hz), 7.95 (2H, d, J=8.4 Hz), 8.08 (2H, d, J=8.4 Hz), LC/MS: APCI 490.0, HPLC 100%.

(Compound D40): 2-{5-[1-(5-biphenyl-3-yl-furan-2-yl)-methylidene]-4-oxo-2-thioxo-thiazolidin-3-ylamino}-benzoic acid; $^1$H NMR (400 MHz, DMSO-d$_6$): δ 6.55 (1H, d, J=8.4 Hz), 6.86 (1H, t, J=8.0 Hz), 7.31 (1H, t, J=7.6 Hz), 7.44-7.55 (5H, m), 7.68-7.81 (5H, m), 7.88-7.93 (2H, m), 8.19 (1H, s), LC/MS: APCI 498.0, HPLC 90%.

(Compound D41): 2-{5-[5-(4-acetylamino-phenyl)-furan-2-ylmethylene]-4-oxo-2-thioxo-thiazolidin-3-ylamino}-benzoic acid; $^1$H NMR (400 MHz, DMSO-d$_6$): δ 2.09 (3H, s), 6.54 (1H, d, J=8.4 Hz), 6.87 (1H, m), 7.25 (1H, d, J=4.0 Hz), 7.33 (1H, m), 7.41 (1H, d, J=3.6 Hz), 7.74 (1H, s), 7.77 (2H, m), 7.82 (2H, m), 7.92 (1H, dd, J=1.6 Hz & 8.0 Hz), 10.24 (1H, s), 10.45 (1H, bs). LC/MS: APCI 478.0, HPLC 96%.

(Compound D42): 2-{5-[1-[5-(4-acetyl-phenyl)-furan-2-yl]-methylidene]-4-oxo-2-thioxo-thiazolidin-3-ylamino}-benzoic acid; $^1$H NMR (400 MHz, DMSO-d$_6$): δ 2.63 (3H, s), 6.58 (1H, d, J=7.6 Hz), 6.88 (1H, t, J=7.6 Hz), 7.34 (1H, t, J=7.6 Hz), 7.45 (1H, d, J=3.6 Hz), 7.55 (1H, d, J=3.6 Hz), 7.80 (1H, s), 7.91 (1H, dd, J=8.0, 1.2 Hz), 8.00-8.03 (2H, m), 8.15-8.17 (2H, m), LC/MS. APCI 463.0, HPLC 99%.

(Compound D43): 2-{5-[1-[5-(2-fluoro-phenyl)-furan-2-yl]-methylidene]-4-oxo-2-thioxo-thiazolidin-3-ylamino}-benzoic acid; $^1$H NMR (400 MHz, DMSO-d$_6$): δ 6.44 (1H, d, J=8 Hz), 6.80 (1H, m), 7.23 (2H, m), 7.41-7.55 (4H, m), 7.78 (1H, s), 7.89-7.95 (2H, m). LC/MS: APCI 439.0, HPLC 92%.

(Compound D44): 2-{5-[1-[5-(3-hydroxymethyl-phenyl)-furan-2-yl]-methylidene]-4-oxo-2-thioxo-thiazolidin-3-ylamino}-benzoic acid; $^1$H NMR (400 MHz, DMSO-d$_6$): δ 4.60 (2H, d, J=3.6 Hz), 6.62 (1H, d, J=7.6 Hz), 6.91 (1H, t, J=7.6 Hz), 7.36-7.44 (4H, m), 7.55 (1H, t, J=8.0 Hz), 7.76-

7.78 (2H, m), 7.87 (1H, s), 7.92 (1H, dd, J=8.0 Hz, 1.6 Hz), LC/MS: APCI 451.0, HPLC 96%.

(Compound D45): 2-{5-[1-[5-(4-fluoro-phenyl)-furan-2-yl]-methylidene]-4-oxo-2-thioxo-thiazolidin-3-ylamino}-benzoic acid; $^1$H NMR (400 MHz, DMSO-$d_6$): δ 6.58 (1H, d, J=8.4 Hz), 6.88 (1H, t, J=8.4 Hz), 7.37 (2H, m), 7.48 (3H, m), 7.77 (1H, s), 7.90-7.96 (3H, m). LC/MS: APCI 439.0, HPLC 93%.

(Compound D46): 2-[5-(4H-furo[3,2-b]indol-2-ylmethylene)-4-oxo-2-thioxo-thiazolidin-3-ylamino]-benzoic acid; $^1$H NMR (400 MHz, DMSO-$d_6$): δ 6.60 (1H, d, J=8.4 Hz), 6.91 (1H, m), 7.18 (1H, m), 7.32 (1H, m), 7.40 (1H, m), 7.52 (1H, d, J=8.0 Hz), 7.55 (1H, s), 7.81 (1H, s), 7.86 (1H, d, J=8.0 Hz), 7.92 (1H, dd, J=8.0 Hz, 1.6 Hz), 9.95 (1H, bs), 11.26 (1H, s). LC/MS: APCI 434.0, HPLC 96%.

(Compound D47): 2-[5-(4-methyl-4H-furo[2-b]indol-2-ylmethylene)-4-oxo-2-thioxo-thiazolidin-3-ylamino]-benzoic acid; $^1$H NMR (400 MHz, DMSO-$d_6$): δ 3.87 (3H, s), 6.62 (1H, d, J=8.4 Hz), 6.19 (1H, m), 7.21 (1H, m), 7.39 (2H, m), 7.60 (1H, d, J=8.4 Hz), 7.62 (1H, s), 7.84 (1H, s), 7.87 (1H, d, J=8.0 Hz), 7.93 (1H, dd, J=8.0 Hz, 1.6 Hz), 9.91 (1H, bs), 13.31 (1H, bs). LC/MS APCI 448.0, HPLC 100%.

(Compound D48): 2-{5-[1-[5-(4-benzyloxy-phenyl)-furan-2-yl]-methylidene]-4-oxo-2-thioxo-thiazolidin-3-ylamino}-benzoic acid; $^1$H NMR (400 MHz, DMSO-$d_6$): δ 5.20 (2H, s), 6.52 (1H, d, J=8.0 Hz), 6.86 (1H, t, J=8.0 Hz), 7.23-7.50 (10H, m), 7.73 (1H, s), 7.83-7.86 (2H, m), 7.91 (1H, dd, J=7.6 Hz, 1.6 Hz), LC/MS: APCI 527.0, HPLC 93%.

(Compound D49): 2-{5-[1-[5-(4-butoxy-phenyl)-furan-2-yl]-methylidene]-4-oxo-2-thioxo-thiazolidin-3-ylamino}-benzoic acid; $^1$H NMR (400 MHz, DMSO-$d_6$): δ 0.950 (3H, t, J=7.2 Hz), 1.43-1.49 (2H, m), 1.71-1.75 (2H, m), 4.06 (2H, t, J=7.2 Hz), 6.45 (1H, d, J=8.4 Hz), 6.82 (1H, t, J=7.6 Hz), 7.14-7.26 (4H, m), 7.40 (1H, d, J=3.6 Hz), 7.72 (1H, s), 7.81-7.83 (2H, m), 7.91 (1H, dd, J=7.6 Hz, 1.6 Hz), LC/MS: APCI 493.1, HPLC 98%.

(Compound D50): 2-{5-[5-(4-methanesulfonyl-phenyl)-furan-2-ylmethylene]-4-oxo-2-thioxo-thiazolidin-3-ylamino}-benzoic acid; $^1$H NMR (400 MHz, DMSO-$d_6$): δ 3.28 (3H, s), 6.58 (1H, d, J=8.0 Hz), 6.88 (1H, m), 7.34 (1H, m), 7.46 (1H, d, J=4.0 Hz), 7.59 (1H, d, J=4.0 Hz), 7.80 (1H, s), 7.92 (1H, dd, J=7.6 Hz, 1.6 Hz), 8.12 (4H, s). LC/MS: APCI 448.0, HPLC 100%.

(Compound D51): 2-{4-oxo-2-thioxo-5-[1-(5-o-tolyl-furan-2-yl)-methylidene]-thiazolidin-3-ylamino}-benzoic acid; $^1$H NMR (400 MHz, DMSO-$d_6$): δ 2.56 (3H, s), 6.49 (1H, d, J=8 Hz), 6.83 (1H, t, J=7.6 Hz), 7.13 (1H, d, J=4 Hz), 7.26 (1H, m), 7.37-7.45 (4H, m), 7.77 (1H, s), 7.84 (1H, d, J=7.6 Hz), 7.91 (1H, m). LC/MS: APCI 435.0, HPLC 100%.

(Compound D52): 2-{5-[1-[5-(3-methylsulfanyl-phenyl)-furan-2-yl]-methylidene]-4-oxo-2-thioxo-thiazolidin-3-ylamino}-benzoic acid; $^1$H NMR (400 MHz, DMSO-$d_6$): δ 2.59 (3H, s), 6.48 (1H, d, J=8.4 Hz), 6.83 (1H, t, J=8.0 Hz), 7.25 (1H, t, J=8.4 Hz), 7.33 (1H, d, J=8.0 Hz), 7.40-7.44 (2H, m), 7.52 (1H, t, J=8.0 Hz), 7.65 (1H, d, J=7.6 Hz), 7.73-7.76 (2H, m), 7.90 (1H, dd, J=7.6 Hz, 1.6 Hz), LC/MS: APCI 467.0, HPLC 94%.

(Compound D53): 2-{5-[1-[5-(4-methylsulfanyl-phenyl)-furan-2-yl]-methylidene]-4-oxo-2-thioxo-thiazolidin-3-ylamino}-benzoic acid; $^1$H NMR (400 MHz, DMSO-$d_6$): δ 2.55 (3H, s), 6.53 (1H, d, J=8.4 Hz), 6.86 (1H, t, J=8.0 Hz), 7.29-7.33 (2H, m), 7.41 (1H, d, J=4.0 Hz), 7.45-7.47 (2H, m), 7.75 (1H, s), 7.81-7.83 (2H, m), 7.91 (1H, dd, J=8.0 Hz, 1.6 Hz). LC/MS. APCI 467.0, HPLC 95%.

(Compound D54): 2-{5-[5-(4-isopropoxy-phenyl)-furan-2-ylmethylene)-4-oxo-2-thioxo-thiazolidin-3-ylamino}-benzoic acid; $^1$H NMR (400 MHz, DMSO-$d_6$): δ 1.31 (6H, d, J=6.0 Hz), 4.73 (1H, septet, J=6.0 Hz), 6.53 (1H, d, J=8.4 Hz), 6.86 (1H, m), 7.14 (2H, m), 7.22 (1H, d, J=3.6 Hz), 7.32 (1H, m), 7.40 (1H, d, J=4.0 Hz), 7.73 (1H, s), 7.82 (2H, m), 7.91 (1H, dd, J=8.0 Hz, 1.6 Hz). LC/MS: APCI 479.0, HPLC 100%.

(Compound D55): 2-{5-[1-(4'-methyl-biphenyl-3-yl)-methylidene]-4-oxo-2-thioxo-thiazolidin-3-ylamino}-benzoic acid; $^1$H NMR (400 MHz, DMSO-$d_6$): δ 2.37 (3H, s), 6.53 (1H, d, J=8.4 Hz), 6.83 (1H, t, J=8 Hz), 7.26 (1H, m), 7.34 (2H, d, J=8 Hz), 7.69 (4H, m), 7.83 (1H, m), 7.92 (1H, m), 7.98 (2H, m). LC/MS: APCI 445.0, HPLC 92%.

(Compound D56): 2-{5-[1-(4'-methyl-biphenyl-4-yl)-methylidene]-4-oxo-2-thioxo-thiazolidin-3-ylamino}-benzoic acid; $^1$H NMR (400 MHz, DMSO-$d_6$): δ 2.37 (3H, s), 6.64 (1H, d, J=8 Hz), 6.89 (1H, t, J=8 Hz), 7.32-7.39 (3H, m), 7.70 (2H, d, J=8 Hz), 7.79 (2H, d, J=8.8 Hz), 7.88-7.94 (4H, m). LC/MS: APCI 445.0, HPLC 98%.

(Compound D57): 2-{5-[1-(5-biphenyl-2-yl-furan-2-yl)-methylidene]-4-oxo-2-thioxo-thiazolidin-3-ylamino}-benzoic acid, $^1$H NMR (400 MHz, DMSO-$d_6$): δ 6.05 (1H, d, J=7.6 Hz), 6.53 (1H, d, J=8.4 Hz), 6.90 (1H, t, J=7.6 Hz), 7.20 (1H, d, J=4.0 Hz), 7.30-7.32 (2H, m), 7.37-7.47 (5H, m), 7.54-7.65 (3H, m), 7.90-7.932 (2H, m), LC/MS: APCI 498.0, HPLC 97%.

(Compound D58): 2-{5-[1-[5-(2-ethyl-phenyl)-furan-2-yl]-methylidene]-4-oxo-2-thioxo-thiazolidin-3-ylamino}-benzoic acid; $^1$H NMR (400 MHz, DMSO-$d_6$): δ 1.20 (3H, t, J=7.6 Hz), 2.93 (2H, q, J=7.6 Hz) (3H, s), 6.47 (1H, d, J=8.0 Hz), 6.82 (1H, t, J=7.6 Hz), 7.09 (1H, d, J=3.6 Hz), 7.22-7.26 (1H, m), 7.43-7.45 (4H, m), 7.76-7.78 (2H, m), 7.90 (1H, dd, J=7.6 Hz, 1.6 Hz), LC/MS: APCI 449.0, HPLC 100%.

(Compound D59): 2-{5-[1-[5-(4-butyl-phenyl)-furan-2-yl]-methylidene]-4-oxo-2-thioxo-thiazolidin-3-ylamino}-benzoic acid; $^1$H NMR (400 MHz, DMSO-$d_6$): δ 0.91 (3H, t, J=7.2 Hz), 1.33 (2H, m), 1.59 (2H, m), 2.64 (2H, t, J=7.6 Hz), 6.46 (1H, d, J=8 Hz), 6.81 (1H, t, J=7.2 Hz), 7.22 (1H, m), 7.31 (1H, d, J=4 Hz), 7.42 (3H, m), 7.74 (1H, s), 7.81 (2H, d, J=8 Hz), 7.91 (1H, m). LC/MS: APCI 477.0, HPLC 94%.

(Compound D60): 2-{5-[1-[5-(4-propyl-phenyl)-furan-2-yl]-methylidene]-4-oxo-2-thioxo-thiazolidin-3-ylamino}-benzoic acid; $^1$H NMR (400 MHz, DMSO-$d_6$): δ 0.92 (3H, t, J=7.6 Hz), 1.65 (2H, m), 2.62 (2H, t, J=7.6 Hz), 6.61 (1H, d, J=8.4 Hz), 6.90 (1H, t, J=8 Hz), 7.31-7.43 (5H, m), 7.76 (1H, s), 7.82 (2H, d, J=8.4 Hz), 7.93 (1H, d, J=1.6 Hz). LC/MS: APCI 463.0, HPLC 100%.

General Procedure for the Synthesis of Ester/Amide Derivatives Listed in Tables 20 and 21 (Compounds T1-T8 and/or U1-U10):

Ester-based Derivatives: A mixture of starting acid (0.44 mol), an alcohol (e.g. diol, triol, N-protected alcohols) (2.2 mmol), 1-[3-(dimethylamino)propyl]3-ethylcarbodiimide (0.88 mmol) and 4-(dimethylamino)pyridine (0.44 mmol) in dichloromethane 16.0 mL was stirred at room temperature for 18 hour. The reaction mixture was poured into 200 mL dichloromethane and washed in a separation funnel successively with 1N HCl 50 mL and brine 30 mL. The organic layer was concentrated under reduced pressure and the crude material was purified by column chromatography on flash Silica eluted with 0.3 to 5% methanol in dichloromethane to afford the corresponding ester, yield 50-55%. When ester formation was carried out using an N-protected amino alcohol, the protecting group was subsequently removed, e.g. by treatment with acid such as HCl or TFA, to provide the ester derivative containing a free amine group.

Amide-based Derivatives—Procedure C: To a suspension of carboxylic acid (0.45 mmol) in dichloromethane (50 mL) was added oxalyl chloride (2.02 mmol) followed by catalytic amount of dimethylformamide or thionyl chloride (2.02 mmol). The mixture was stirred 3 h at room temperature and/or gently heated. Volatiles were removed under reduced pressure. The crude acyl chloride was used as such. To a suspension of the amino component (0.45 mmol) in THF (30 mL) was added a suspension of the acyl chloride in THF (20 mL). The mixture was stirred at room temperature for 17 h. The reaction mixture was concentrated under reduced pressure. The crude material was chromatographed on flash Silica to provide the corresponding amide in 5-45% yield.

Amide-based Derivatives—Procedure D: A mixture of the carboxylic acid (0.45 mmol) in dichloromethane or DMF (50 mL), amine component and a coupling agent such as HBTU [2-(1H-benzotriazole-1-yl)-1,1,3,3-tetramethyluronium hexafluorophosphate] or HOAt [1-hydroxy-7-azabenzotriazole] with or without added tertiary amine were stirred at room temperature overnight, the reaction mixture was concentrated in vacuo and purified through a silica plug to provide the desired product.

The following are representative specific examples:

(Compound T1): 3-{5-[1-[5-(2-Chloro-phenyl)-furan-2-yl]-methylidene]-4-oxo-2-thioxo-thiazolidin-3-yl}-benzoic acid 4-hydroxy-butyl ester; $^1$H NMR (400 MHz, CDCl$_3$): δ 1.73 (2H, m), 1.89 (2H, m), 3.72 (2H, m), 4.39 (2H, t, J=6.4 Hz), 7.06 (1H, d, J=3.6 Hz), 7.33-7.37 (1H, m), 7.41 (1H, d, J=3.6 Hz), 7.47-7.54 (3H, m), 7.63-7.67 (1H, m), 7.98-8.05 (2H, m), 8.18-8.21 (1H, m), APCI-MS: 514.5; HPLC: 87%.

(Compound T2): 3-{5-[1-[5-(2-Chloro-phenyl)-furan-2-yl]-methylidene]-4-oxo-2-thioxo-thiazolidin-3-yl}-benzoic acid 3-hydroxy-propyl ester; $^1$H NMR (400 MHz, CDCl$_3$): δ 2.02 (2H, m), 3.78 (2H, t, J=6.4 Hz), 4.51 (2H, t, J=6.4 Hz), 7.05 (1H, d, J=3.6 Hz), 7.33-7.37 (1H, m), 7.41 (1H, d, J=3.6 Hz), 7.47-7.54 (3H, m), 7.58 (1H, s), 7.63-7.67 (1H, m), 7.99-8.05 (2H, m), 8.18-8.21 (1H, m), APCI-MS: 501.1; HPLC: 99%.

(Compound T3): 3-{5-[1-[5-(2-Chloro-phenyl)-furan-2-yl]-methylidene]-4-oxo-2-thioxo-thiazolidin-3-yl}-benzoic acid 4-phosphonooxy-butyl ester; $^1$H NMR (400 MHz, DMSO-d$_6$): δ 1.73 (2H, m), 1.89 (2H, m), 3.72 (2H, m), 4.39 (2H, t, J=6.4 Hz), 7.41-7.52 (3H, m), 7.61-7.77 (5H, m), 7.97-8.12 (3H, m), APCI-MS: 594.1.

(Compound T4): 3-{5-[1-[5-(2-Chloro-phenyl)-furan-2-yl]-methylidene]-4-oxo-2-thioxo-thiazolidin-3-yl}-benzoic acid 3-hydroxy-2-hydroxymethyl-propyl ester; $^1$H NMR (400 MHz, DMSO-d$_6$): δ 1.99 (1H, m), 3.52 (2H, m), 4.33 (2H, m), 4.57 (2H, m), 7.42-7.52 (3H, m), 7.61-7.77 (5H, m), 7.96-8.11 (3H, m), APCI-MS: 529.0; HPLC 100%.

(Compound T5): 3-{5-[1-[5-(2-Chloro-phenyl)-furan-2-yl]-methylidene]-4-oxo-2-thioxo-thiazolidin-3-yl}-benzoic acid 3-hydroxy-2-hydroxymethyl-2-methyl propyl ester; $^1$H NMR (400 MHz, CDCl$_3$): δ 0.93 (3H, s), 3.52 (2H, m), 4.33 (2H, m), 4.57 (2H, m), 7.42-7.52 (3H, m), 7.61-7.77 (5H, m), 7.96-8.11 (3H, m), APCI-MS: 543.0

(Compound T6): 3-{5-[1-[5-(2-Chloro-phenyl)-furan-2-yl]-methylidene]-4-oxo-2-thioxo-thiazolidin-3-yl}-N-(2-hydroxy-1,1-bis-hydroxymethyl-ethyl)-benzamide; $^1$H NMR (400 MHz, DMSO-d$_6$): δ 3.70 (4H, m), 4.73 (2H, m), 7.35 (1H, bs), 7.47-7.52 (3H, m), 7.59-7.68 (4H, m), 7.78 (1H, s), 7.87 (1H, m), 7.96-7.99 (2H, m), APCI-MS: 543.0; HPLC: 92%.

(Compound T7): 3-{5-[1-[5-(2-Chloro-phenyl)-furan-2-yl]-methylidene]-4-oxo-2-thioxo-thiazolidin-3-yl}-N-(2-hydroxy-1-hydroxymethyl-ethyl)-benzamide; $^1$H NMR (500 MHz, DMSO-d$_6$): δ 3.52 (4H, m), 3.98 (1H, m), 4.67 (2H, t, J=5.5 Hz), 7.45-7.51 (2H, m), 7.58-7.68 (3H, m), 7.79 (1H, s), 7.92 (1H, bs), 7.97-8.09 (3H, m), APCI-MS: 514.0; HPLC: 80%.

(Compound T8): 3-{5-[1-[5-(2-Chloro-phenyl)-furan-2-yl]-methylidene]-4-oxo-2-thioxo-thiazolidin-3-yl}-benzoic acid 2-[bis-(2-hydroxy-ethyl)-amino]-ethyl ester; $^1$H NMR (500 MHz, DMSO-d$_6$): δ 2.64 (3H, bs), 2.91 (2H, bs), 3.45 (4H, bs), 4.35 (3H, bs), 7.44-7.51 (3H, m), 7.62-7.68 (2H, m), 7.74 (2H, m), 7.77 (1H, s), 7.99 (1H, m), 8.06 (1H, bs), 8.11 (1H, bs), APCI-MS: 572.0; HPLC: 93%.

(Compound U1): 4-{5-[1-[5-(4-Methylsulfanyl-phenyl)-furan-2-yl]-methylidene]-4-oxo-2-thioxo-thiazolidin-3-yl}-cyclohexanecarboxylic acid 3-hydroxy-propyl ester, $^1$H NMR (400 MHz, CDCl$_3$): δ 1.60-1.68 (4H, m), 1.97 (2H, m), 2.29-2.39 (3H, m), 2.54 (3H, s), 2.59-2.72 (2H, m), 3.78 (2H, m), 4.37 (2H, t, J=6.0 Hz), 5.08 (1H, m), 6.80 (1H, d, J=3.6 Hz), 6.91 (1H, d, J=3.6 Hz), 7.31-7.34 (2H, m), 7.35 (1H, s), 7.68-7.70 (2H, m), APCI-MS: 500.0; HPLC: 96%.

(Compound U2): 3-{5-[1-[5-(4-Methylsulfamoyl-phenyl)-furan-2-yl]-methylidene]-4-oxo-2-thioxo-thiazolidin-3-yl}-cyclohexanecarboxylic acid 3-hydroxy-propyl ester; $^1$H NMR (400 MHz, DMSO-d$_6$): δ 1.71 (2H, m), 2.51 (3H, s), 3.44 (2H, m), 4.08 (2H, t, J=6.8 Hz), 4.51 (1H, t, J=5.2 Hz), 7.41 (1H, d, J=3.6 Hz), 7.50-7.55 (2H, m), 7.63 (1H, s), 7.94 (2H, m), 8.06 (2H, m), APCI-MS: 564.1; HPLC: 100%.

(Compound U3): 3-{5-[1-[5-(4-Methylsulfanyl-phenyl)-furan-2-yl]-methylidene]-4-oxo-2-thioxo-thiazolidin-3-yl}-cyclohexanecarboxylic acid 2-hydroxy-ethyl ester; $^1$H NMR (400 MHz, CDCl$_3$): δ 1.73 (6H, m), 2.37 (2H, m), 2.54 (3H, s), 2.62 (1H, m), 3.95 (2H, m), 4.37 (2H, m), 5.12 (1H, m), 6.81 (1H, d, J=3.6 Hz), 6.93 (1H, d, J=4 Hz), 7.34 (2H, m), 7.38 (1H, s), 7.70 (2H, m), APCI-MS: 503.0; HPLC: 98%.

(Compound U4): 3-{5-[1-[5-(4-Methylsulfanyl-phenyl)-furan-2-yl]-methylidene]-4-oxo-2-thioxo-thiazolidin-3-yl}-cyclohexanecarboxylic acid 4-hydroxy-butyl ester; $^1$H NMR (400 MHz, CDCl$_3$): δ 1.73-2.10 (10H, m), 2.37 (2H, m), 2.54 (3H, s), 2.62 (1H, m), 3.95 (2H, m), 4.37 (2H, m), 5.12 (1H, m), 6.81 (1H, d, J=3.6 Hz), 6.93 (1H, d, J=4 Hz), 7.34 (2H, m), 7.38 (1H, s), 7.70 (2H, m), APCI-MS: 531.1; HPLC: 100%.

(Compound U5): 3-{5-[1-[5-(4-Methylsulfanyl-phenyl)-furan-2-yl]-methylidene]-4-oxo-2-thioxo-thiazolidin-3-yl}-cyclohexanecarboxylic acid 3-hydroxy-2-hydroxymethyl-propyl ester; $^1$H NMR (400 MHz, CDCl$_3$): δ 1:73 (6H, m), 2.37 (2H, m), 2.54 (3H, s), 2.62 (1H, m), 3.95 (4H, m), 4.37 (2H, m), 5.12 (1H, m), 6.81 (1H, d, J=3.6 Hz), 6.93 (1H, d, J=4 Hz), 7.31-7.34 (3H, m), 7.70 (2H, m), APCI-MS: 547.1; HPLC: 98%.

(Compound U6): 3-{5-[1-[5-(4-Methylsulfanyl-phenyl)-furan-2-yl]-methylidene]-4-oxo-2-thioxo-thiazolidin-3-yl}-cyclohexanecarboxylic acid 3-hydroxy-2-hydroxymethyl-2-methyl-propyl ester; $^1$H NMR (400 MHz, CDCl$_3$): δ 0.91 (3H, s), 1.73 (4H, m), 2.37 (2H, m), 2.54 (3H, s), 2.62 (1H, m), 3.65 (4H, m), 4.37 (2H, m), 5.12 (1H, m), 6.81 (1H, d, J=3.6 Hz), 6.93 (1H, d, J=4 Hz), 7.31-7.34 (3H, m), 7.70 (2H, m), APCI-MS 561.1; HPLC: 100%.

(Compound U7): 3-{5-[1-[5-(4-Methylsulfanyl-phenyl)-furan-2-yl]-methylidene]-4-oxo-2-thioxo-thiazolidin-3-yl}-cyclohexanecarboxylic acid (2-hydroxy-1,1-bis-hydroxymethyl-ethyl)-amide; $^1$H NMR (400 MHz, CDCl$_3$): δ 1.73 (4H, m), 2.37 (2H, m), 2.54 (3H, s), 2.62 (1H, m), 3.65 (4H, m), 4.37 (2H, m), 5.19 (1H, m), 6.81 (1H, d, J=3.6 Hz), 6.93 (1H, d, J=4 Hz), 7.21 (1H, bs), 7.31-7.34 (3H, m), 7.70 (2H, m), APCI-MS: 562.1; HPLC: 96%.

(Compound U8): 3-{5-[1-[5-(4-Methylsulfanyl-phenyl)-furan-2-yl]-methylidene]-4-oxo-2-thioxo-thiazolidin-3-yl}-cyclohexanecarboxylic acid (2-hydroxy-1-hydroxymethyl-ethyl)-amide; $^1$H NMR (400 MHz, CDCl$_3$): δ 1.73 (4H, m), 2.37 (2H, m), 2.54 (3H, s), 2.66 (3H, m), 4.02 (4H, m), 5.19

(1H, m), 6.81 (1H, d, J=3.6 Hz), 6.93 (1H, d, J=4 Hz), 7.21 (1H, bs), 7.31-7.34 (3H, m), 7.70 (2H, m), APCI-MS: 532.1, HPLC: 98%.

(Compound U9): 3-{5-[1-[5-(4-Methanesulfonyl-phenyl)-furan-2-yl]-methylidene]-4-oxo-2-thioxo-thiazolidin-3-yl}-cyclohexanecarboxylic acid 3-hydroxy-propyl ester; $^1$H NMR (400 MHz, DMSO-d$_6$): δ 1.60 (4H, m), 1:78 (2H, m), 2.22 (2H, m), 2.46 (1H, m), 2.72 (1H, m), 3.26 (3H, s), 4.19 (2H, m), 4.54 (1H, t, J=4.8 Hz), 4.93 (1H, m), 7.39 (1H, d, J=3.6 Hz), 7.50-7.55 (2H, m), 7.62 (1H, s), 8.08 (4H, m), APCI-MS: 549.0; HPLC 90%.

(Compound U10): 3-{5-[1-[5-(4-Methylsulfanyl-phenyl)-furan-2-yl]-methylidene]-4-oxo-2-thioxo-thiazolidin-3-yl}-cyclohexanecarboxylic acid 2-[bis-(2-hydroxy-ethyl)-amino]-ethyl ester hydrochloride; $^1$H NMR (400 MHz, DMSO-d$_6$): δ 1.60 (4H, m), 2.24 (2H, m), 2.49 (2H, m), 2.54 (3H, s), 2.80 (1H, m), 3.58 (2H, m), 3.79 (4H, bs), 4.49 (2H, t, J=4.8 Hz), 4.94 (1H, m), 5.34 (2H, bs), 7.31 (1H, d, J=3.6 Hz), 7.37 (1H, d, J=3.6 Hz), 7.46 (2H, m), 7.54 91H, s), 7.79 (2H, m), APCI-MS: 590.1, HPLC: 96%.

Example 1

3-{5-[1-[5-(4-tert-butyl-phenyl)-furan-2-yl]-methylidene]-4-oxo-2-thioxo-thiazolidin-3-yl}-cyclohexanecarboxylic acid; (Compound C3)

Part A: 5-(4-tert-butyl-phenyl)-furan-2-carbaldehyde

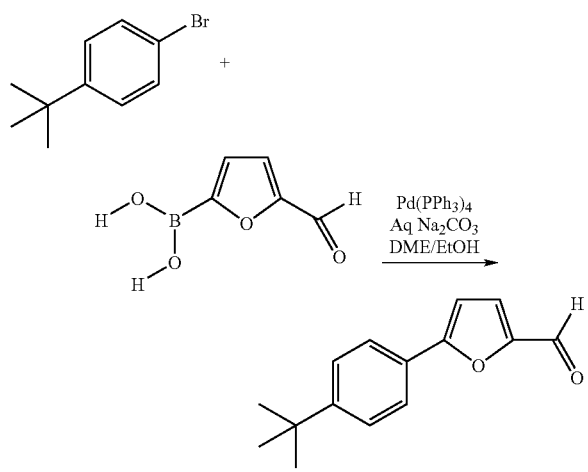

To a round bottom flask containing 1-bromo-4-tert-butylbenzene (1.5 g, 7.04 mmol) and 5-formyl-2-furan-boronic acid (1.47 g, 10.56 mmol) in dimethoxyethane (80 mL) and ethanol (20 mL) was added an aqueous solution of sodium carbonate (2.24 g, 21.12 mmol) m water (30 mL). The reaction mixture was stirred at room temperature for 5 minutes, followed by the addition of tetrakis(triphenylphosphine)palladium (404 mg, 0.35 mmol). The reaction mixture was heated at 70° C. for 1 h. The reaction mixture was cooled to room temperature, diluted with ethyl acetate (500 mL) and water (50 mL). The layers were separated and the aqueous layer was extracted with ethyl acetate (2×150 mL). The combined organic extracts were washed with brine, dried (sodium sulfate) and concentrated under vacuum. The crude product was purified by silica gel chromatography eluting with 20% ethyl acetate in hexanes to afford 5-(4-tert-butyl-phenyl)-furan-2-carbaldehyde (1.16 g, 72%) as a dark brown solid. $^1$H NMR (400 MHz, CDCl$_3$): δ 1.35 (9H, s), 6.80 (1H, d, J=3.6 Hz), 7.31 (1H, d, J=3.6 Hz), 7.44-7.7.48 (2H, m), 7.74-7.77 (2H, m), 9.64 (1H, s); APCI-MS: 228.34.

Part B: 3-(4-oxo-2-thioxo-thiazolidin-3-yl)-cyclohexanecarboxylic acid

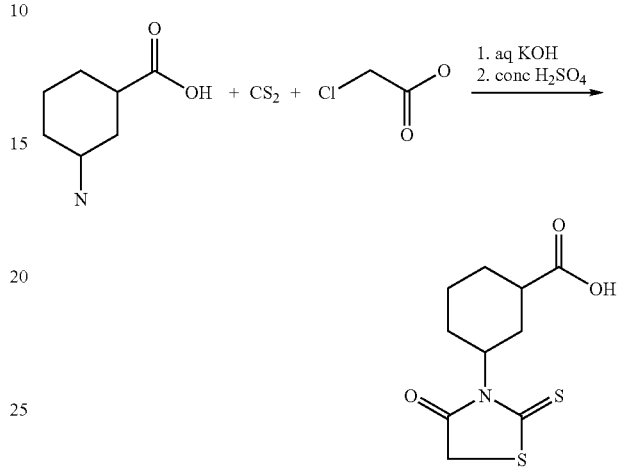

To a round bottom flask containing 3-amino-cyclohexanecarboxylic acid (3.80 g, 26.54 mmol) was added aqueous potassium hydroxide (3 g, 53.08 mmol) in water (20 mL). The reaction mixture was stirred at room temperature for 15 minutes. Carbon disulfide (1.60 mL, 26.54 mmol) was added drop-wise to the reaction mixture and stirred at room temperature for 1.5 h. The reaction mixture was then cooled to 0° C. and an aqueous solution of chloroacetic acid (2.5 g, 26.54 mmol) and potassium hydroxide (1.5 g, 26.54 mmol) in water (15 mL) was added slowly to the reaction mixture. The cooling bath was removed and the reaction mixture stirred at room temperature for 1.5 h. The reaction mixture was cooled to 0° C. and acidified with concentrated sulfuric acid (3 mL). The cooling bath was removed and the reaction mixture was heated at 100° C. for 8 h and then allowed to cool to room temperature overnight. The solid was filtered, washed with water (15 mL), 1:1 hexanes/ether (100 mL) and hexanes (100 mL). The solid was dried in a vacuum oven at 55-60° C. for 5 h to afford 3-(4-oxo-2-thioxo-thiazolidin-3-yl)-cyclohexanecarboxylic acid (1.46 g, 21%) as a solid. $^1$H NMR (400 MHz, DMSO-d$_6$): δ 1.16-1.39 (2H, m), 1.57 (1H, m), 1.79-1.89 (3H, m), 1.96-2.36 (3H, m), 4.12 (2H, s), 4.79 (1H, m), 12.18 (1H, s); APCI-MS: 258.31

Part C: 3-{5-[1-[5-(4-tert-butyl-phenyl)-furan-2-yl]-methylidene]-4-oxo-2-thioxo-thiazolidin-3-yl}-cyclohexanecarboxylic acid

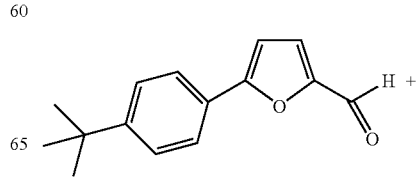

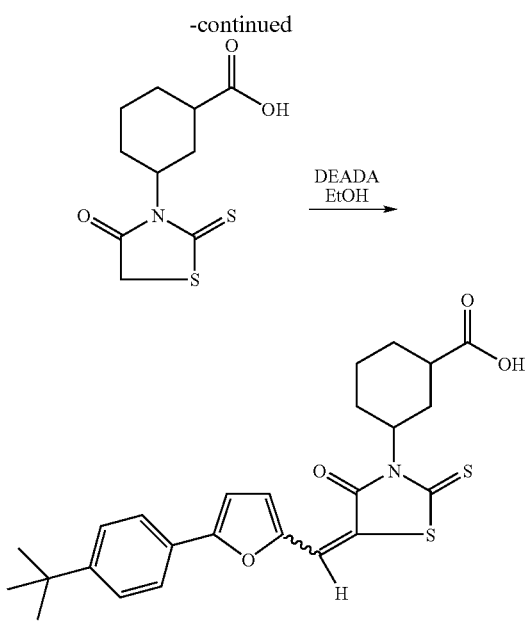

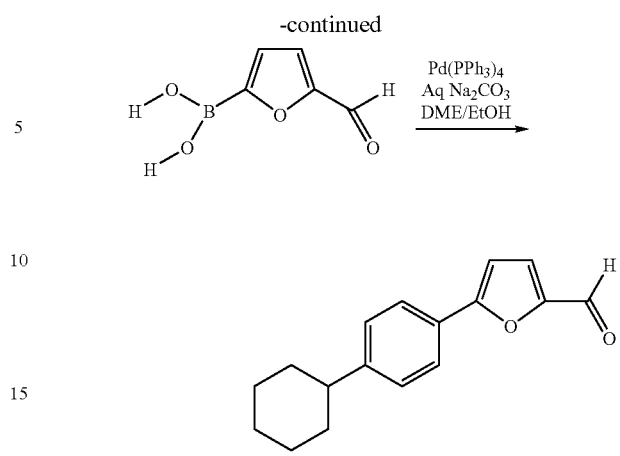

3-(4-oxo-2-thioxo-thiazolidin-3-yl)-cyclohexanecarboxylic acid (80 mg, 0.31 mmol), 5-(4-tert-butyl-phenyl)-furan-2-carbaldehyde (75 mg, 0.33 mmol), and diethylenediamine diacetate (59 mg, 0.33 mmol) were combined in a 20 mL vial with ethanol (5 mL) and stirred at room temperature for 65 h. The reaction mixture was diluted with 10% methanol in dichloromethane (200 mL) and aqueous ammonium chloride (20 mL) and stirred at room temperature for 15 minutes. The layers were separated and the aqueous layer was extracted with 10% methanol in dichloromethane (2×100 mL). The combined organic extracts were washed with 0.6N sodium hydrogensulfite (1×20 mL) and then brine (1×20 mL), dried (sodium sulfate) and concentrated under vacuum. The residue was triturated with dichloromethane/hexanes (1:5:30 mL), filtered and dried overnight in a vacuum oven at 55° C. to afford 3-{5-[1-[5-(4-tert-butyl-phenyl)-furan-2-yl]-methylidene]-4-oxo-2-thioxo-thiazolidin-3-yl}-cyclohexanecarboxylic acid (100 mg, 69%) as a solid. $^1$H NMR (400 MHz, DMSO-$d_6$): δ 1.32 (9H, s), 1.25-1.41 (2H, m), 1.67 (1H, m), 1.87-1.92 (3H, m), 2.29-2.45 (3H, m), 4.98 (1H, m), 7.26 (1H, d, J=3.6 Hz), 7.36 (1H, d, J=3.6 Hz), 7.59-7.61 (3H, m), 7.77-7.70 (2H, m), 12.20 (1H, s); APCI-MS: 469.52; HPLC: 95%.

Example 2

3-{5-[1-[5-(4-cyclohexyl-phenyl)-furan-2-yl]-methylidene]-4-oxo-2-thioxo-thiazolidin-3-yl}-cyclohexanecarboxylic acid; (Compound C2)

Part A:
5-(4-cyclohexyl-phenyl)-furan-2-carbaldehyde

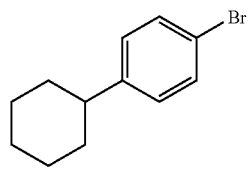

To a round bottom flask containing 1-bromo-4-cyclohexylbenzene (1.5 g, 6.27 mmol) and 5-formyl-2-furan-boronic acid (1.32 g, 9.41 mmol) in dimethoxyethane (80 mL) and ethanol (20 mL) was added an aqueous solution of sodium carbonate (1:99 g, 18.81 mmol) in water (30 mL) The reaction mixture was stirred at room temperature for 5 minutes, followed by the addition of tetrakis(triphenylphosphine)palladium (358 mg, 0.31 mmol). The reaction mixture was heated at 70° C. for 1 h. The reaction mixture was then cooled to room temperature and diluted with ethyl acetate (500 mL) and water (50 mL). The layers were separated and the aqueous layer was extracted with ethyl acetate (2×150 mL). The combined organic extracts were washed with brine, dried (sodium sulfate) and concentrated under vacuum. The crude product was purified by silica gel chromatography, eluting with 15% ethyl acetate in hexanes to afford 5-(4-cyclohexyl-phenyl)-furan-2-carbaldehyde (850 mg, 53%) as a solid. $^1$H NMR (400 MHz, CDCl$_3$): δ 1.28-1.46 (5H, m), 1.75-1.87 (5H, m), 2.53-2.54 (1H, m), 6.79 (1H, d, J=3.6 Hz), 7.26-7.32 (3H, m), 7.73-7.76 (2H, m), 9.63 (1H, s).

Part B: 3-{5-[1-[5-(4-cyclohexyl-phenyl)-furan-2-yl]-methylidene]-4-oxo-2-thioxo-thiazolidin-3-yl}-cyclohexanecarboxylic acid

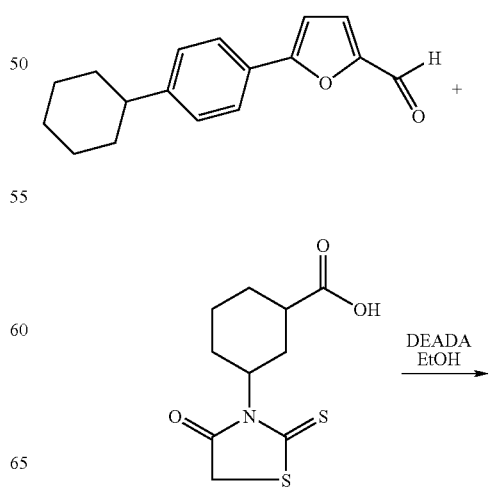

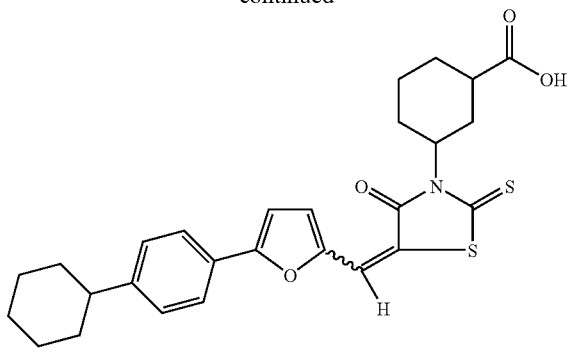

3-(4-oxo-2-thioxo-thiazolidin-3-yl)-cyclohexanecarboxylic acid (80 mg, 0.31 mmol), 5-(4-cyclohexyl-phenyl)-furan-2-carbaldehyde (84 mg, 0.33 mmol), and diethylenediamine diacetate (59 mg, 0.33 mmol) were combined in a 20 mL vial with ethanol (5 mL) and stirred at room temperature for 65 h. The reaction mixture was diluted with 10% methanol in dichloromethane (200 mL) and aqueous ammonium chloride (20 mL) and stirred at room temperature for 15 minutes. The layers were separated and the aqueous layer was extracted with 10% methanol in dichloromethane (2×100 mL). The combined organic extracts were washed with 0.6 N sodium hydrogensulfite (1×20 mL) and then brine (1×20 mL), dried (sodium sulfate) and concentrated under vacuum. The residue was triturated with dichloromethane/hexanes (1:5, 30 mL), filtered and dried overnight in a vacuum oven at 55° C. to afford 3-{5-[1-[5-(4-cyclohexyl-phenyl)-furan-2-yl]-methylidene]-4-oxo-2-thioxo-thiazolidin-3-yl}-cyclohexanecarboxylic acid (100 mg, 65%) as a solid. $^1$H NMR (400 MHz, DMSO-$d_6$): δ 1.25-1.49 (7H, m), 1.67-1.92 (10H, m), 2.35-2.45 (2H, m), 2.56 (1H, m), 4.97 (1H, m), 7.26 (1H, d, J=3.6 Hz), 7.36 (1H, d, J=3.6 Hz), 7.42 (1H, d, J=8.4 Hz), 7.59 (1H, s), 7.77 (1H, d, J=8.4 Hz), 12.18 (1H, s); APCI-MS: 495.37; HPLC: 90%.

Example 3

3-{5-[1-[5-(4-isobutyl-phenyl)-furan-2-yl]-methylidene]-4-oxo-2-thioxo-thiazolidin-3-yl}-cyclohexanecarboxylic acid; (Compound C4)

Part A: 5-(4-isobutyl-phenyl)-furan-2-carbaldehyde

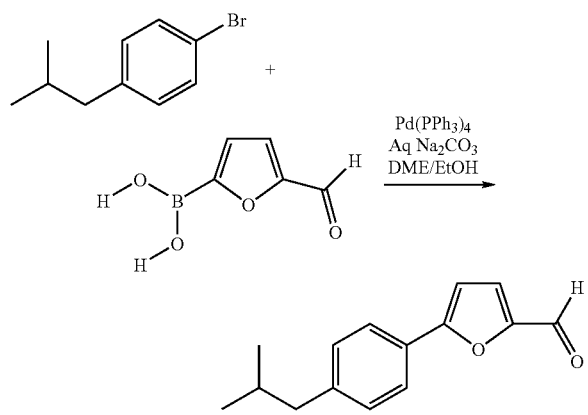

A mixture of 1-bromo-4-isobutylbenzene (1.500 g, 7.04 mmol), 5-formyl-2-furanoboronic acid (1.477, 10.56 mmol) and sodium carbonate (3.134 g, 29.57 mmol) in a mixture of 1,2-dimethoxyethane (75 mL), ethanol (30 mL) and water (15 mL) was vigorously stirred and the reaction flask was purged with nitrogen. Tetrakis(triphenylphosphine)palladium(0) (0.404 g, 0.35 mmol) was added and the reaction mixture was heated at 60° C. for 3 h. The mixture was allowed to cool to room temperature and was left aside for 4 days. The reaction mixture was diluted with ether (200 mL) and washed successively with water (2×100 mL) and brine. The organic layer was separated, dried over sodium sulfate and concentrated. The residue was chromatographed on flash Silica, eluted with 5 to 10% ethyl acetate in hexanes to afford 5-(4-isobutyl-phenyl)-furan-2-carbaldehyde (490 mg, 31%). $^1$H NMR (400 MHz, CDCl$_3$): 0.92 (6H, d, J=6.4 Hz), 1.90 (1H, m), 2.51 (2H, d, J=7.2 Hz), 6.80 (1H, d, J=3.6 Hz), 7.20 (2H, m), 7.31 (1H, dd, J=3.6, 1.2 Hz), 7.74 (2H, m), 9.63 (1H, s). ESI-MS: 227.1.

Part B: 3-{5-[1-[5-(4-isobutyl-phenyl)-furan-2-yl]-methylidene]-4-oxo-2-thioxo-thiazolidin-3-yl}-cyclohexanecarboxylic acid

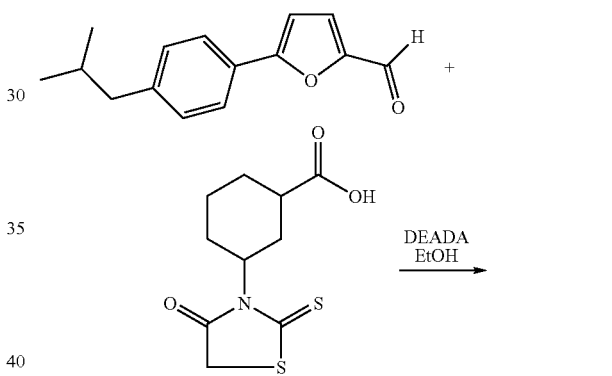

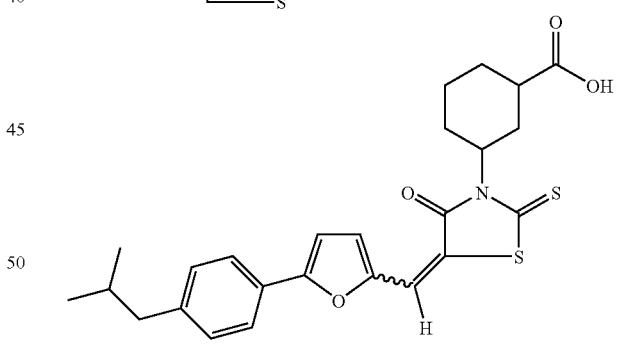

A mixture of 3-(4-oxo-2-thioxo-thiazolidin-3-yl)-cyclohexanecarboxylic acid (0.075 g, 0.29 mmol), 5-(4-isobutyl-phenyl)-furan-2-carbaldehyde (0.069 g, 0.30 mmol) and ethylenediamine diacetate (0.057 g, 0.32 mmol) in anhydrous ethanol (12 mL) was stirred 30 h at ambient temperature. The reaction mixture was diluted with ethyl acetate (250 mL) and extracted with 0.6 N aq. sodium hydrogensulfite (2×50 mL). The organic layer was separated, dried over sodium sulfate and concentrated. The residue was triturated with hot acetonitrile (5 mL) and allowed to cool to room temperature. The product was filtered off, washed on the funnel with acetonitrile (0.5 mL) and dried in a vacuum oven at 60° C. for 17 h to afford 3-{5-[1-[5-(4-isobutyl-phenyl)-furan-2-yl]-methylidene]-4-oxo-2-thioxo-thiazolidin-3-yl}-cyclohexanecarboxylic acid (98 mg, 72%) as a solid. $^1$H NMR (400 MHz, DMSO-d$_6$): δ 0.88 (6H, d, J=6.4 Hz), 1.16-1.45 (2H, m), 1.68 (1H, m), 1.84-1.92 (4H, m), 2.25-2.54 (3H, m), 4.98 (1H, m), 7.27 (1H, d, J=3.6 Hz), 7.36 (2H, m), 7.36 (1H, d, J=3.6 Hz), 7.58 (1H, s), 7.77 (2H, m), 12.22 (1H, s). LC/MS: APCI 469.51, HPLC 100%.

Example 4

3-{5-[1-[5-(4-benzyl-phenyl)-furan-2-yl]-methylidene]-4-oxo-2-thioxo-thiazolidin-3-yl}-cyclohexanecarboxylic acid, (Compound C6)

Part A: 5-(4-benzyl-phenyl)-furan-2-carbaldehyde

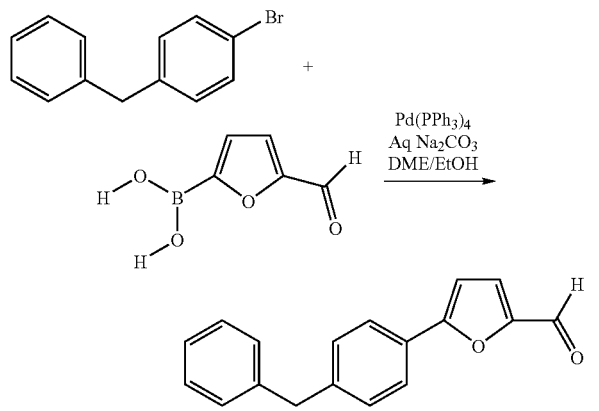

To a round bottom flask containing 1-benzyl-4-bromobenzene (700 mg, 2.83 mmol) and 5-formyl-2-furan-boronic acid (595 mg, 4.25 mmol) in dimethoxyethane (30 mL) and ethanol (7.5 mL) was added an aqueous solution of sodium carbonate (900 mg, 8.49 mmol) in water (10 mL) The reaction mixture was stirred at room temperature for 5 minutes, followed by the addition of tetrakis(triphenylphosphine)palladium (162 mg, 0.14 mmol). The reaction was heated at 70° C. for 1 h. The reaction mixture was cooled to room temperature, diluted with ethyl acetate (200 mL) and water (20 mL). The layers were separated and the aqueous layer was extracted with ethyl acetate (2×50 mL). The combined organic extracts were washed with brine, dried (sodium sulfate) and concentrated under vacuum. The crude product was purified by silica gel chromatography eluting with 6% ethyl acetate in hexanes to afford 5-(4-benzyl-phenyl)-furan-2-carbaldehyde (320 mg g, 43%) as a solid. $^1$H NMR (400 MHz, DMSO-d$_6$) δ 3.99 (2H, s), 7.20-7.39 (8H, m), 7.63 (1H, d, J=3.6 Hz), 7.78-7.81 (2H, m), 9.59 (1H, s); APCI-MS: 262.02.

Part B: 3-{5-[1-[5-(4-benzyl-phenyl)-furan-2-yl]-methylidene]-4-oxo-2-thioxo-thiazolidin-3-yl}-cyclohexanecarboxylic acid

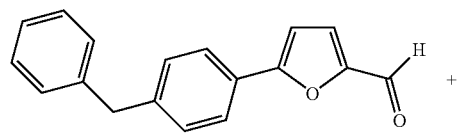

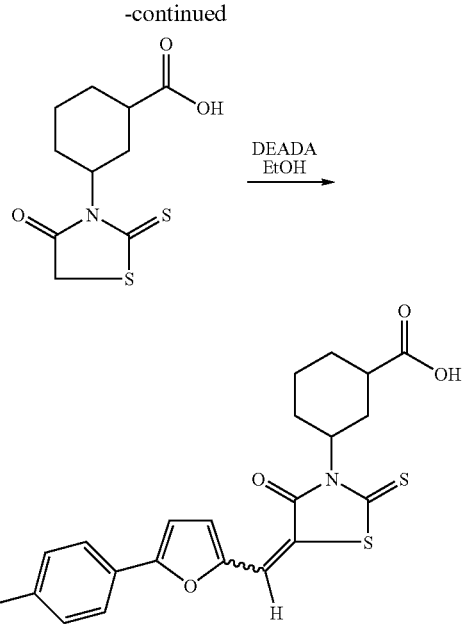

3-(4-oxo-2-thioxo-thiazolidin-3-yl)-cyclohexanecarboxylic acid (80 mg, 0.31 mmol), 5-(4-benzyl-phenyl)-furan-2-carbaldehyde (87 mg, 0.33 mmol), and diethylenediamine diacetate (59 mg, 0.33 mmol) were combined in a 20 mL vial with ethanol (5 mL) and stirred at room temperature for 65 h. The reaction mixture was diluted with 10% methanol in dichloromethane (200 mL) and aqueous ammonium chloride (20 mL) and stirred at room temperature for 15 minutes. The layers were separated and the aqueous layer was extracted with 10% methanol in dichloromethane (2×100 mL). The combined organic extracts were washed with 0.6N sodium hydrogensulfite (1×20 mL) and then brine (1×20 mL), dried (sodium sulfate) and concentrated under vacuum. The residue was triturated with dichloromethane/hexanes (1:5, 30 mL), filtered and dried overnight in a vacuum oven at 55° C. to afford 3-{5-[1-[5-(4-benzyl-phenyl)-furan-2-yl]-methylidene]-4-oxo-2-thioxo-thiazolidin-3-yl}-cyclohexanecarboxylic acid (100 mg, 64%) as a solid. $^1$H NMR (400 MHz, DMSO-d$_6$): δ 1.25-1.41 (2H, m), 1.67 (1H, m), 1.87-1.92 (3H, m), 2.29-2.45 (3H, m), 4.00 (2H, s), 4.97 (1H, m), 7.18-7.22 (1H, m), 7.26-7.32 (5H, m), 7.36 (1H, d, J=3.6 Hz) 7.43 (2H, m), 7.58 (1H, s), 7.77 (1H, d, J=8.0 Hz), 12.18 (1H, s); APCI-MS: 503.54; HPLC: 95%.

Example 5

3-{5-[1-[5-(3-trifluoromethyl-phenyl)-furan-2-yl]-methylidene]-4-oxo-2-thioxo-thiazolidin-31]-cyclohexanecarboxylic acid; (Compound C5)

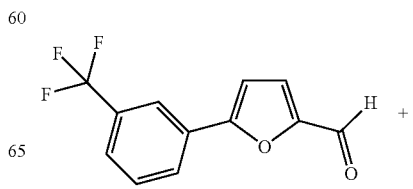

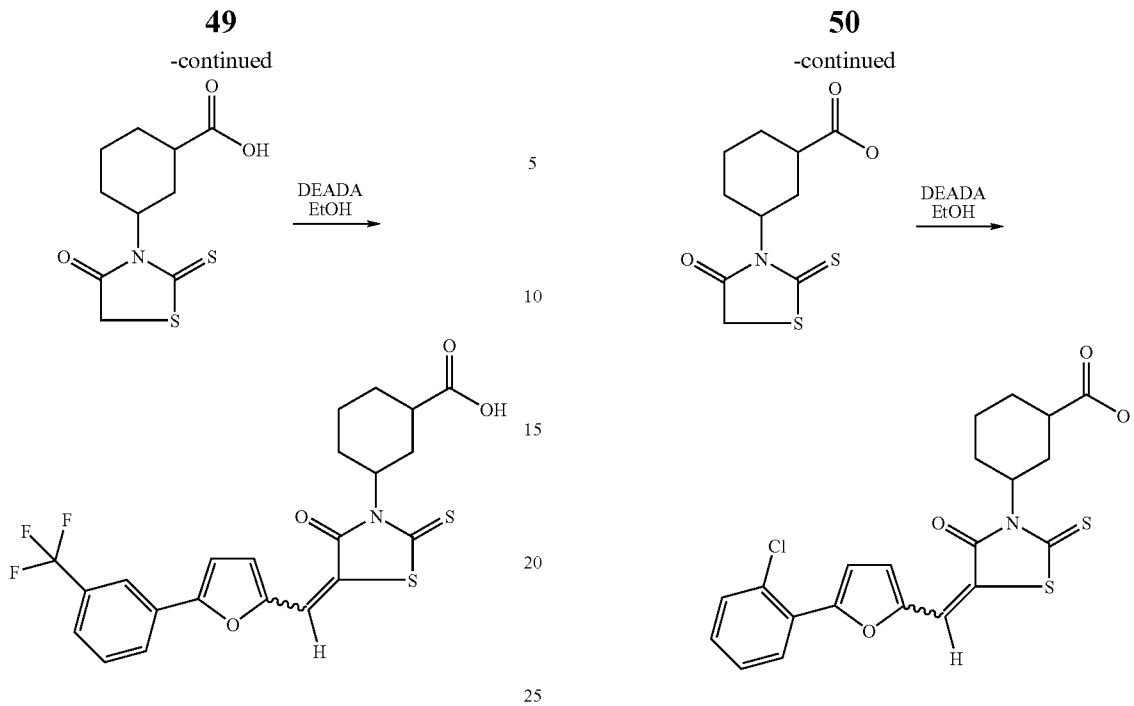

3-(4-Oxo-2-thioxo-thiazolidin-3-yl)-cyclohexanecarboxylic acid (80 mg, 0.31 mmol), 5-(3-trifluoromethyl-phenyl)-furan-2-carbaldehyde (79 mg, 0.33 mmol) (purchased from Aldrich Chemical Company), and diethylenediamine diacetate (59 mg, 0.33 mmol) were combined in a 20 mL vial with ethanol (5 mL) and stirred at room temperature for 65 h. The reaction mixture was diluted with 10% methanol in dichloromethane (200 mL) and aqueous ammonium chloride (20 mL) and stirred at room temperature for 15 minutes. The layers were separated and the aqueous layer was extracted with 10% methanol in dichloromethane (2×100 mL). The combined organic extracts were washed with 0.6 N sodium hydrogensulfite (1×20 mL) and then brine (1×20 mL), dried (sodium sulfate) and concentrated under vacuum. The residue was triturated with dichloromethane/hexanes (1:5, 30 mL), filtered and dried overnight in a vacuum oven at 55° C. to afford 3-{5-[1-[5-(3-trifluoromethyl-phenyl)-furan-2-yl]-methylidene]-4-oxo-2-thioxo-thiazolidin-3-yl}-cyclohexanecarboxylic acid (110 mg, 74%) as a solid. $^1$H NMR (400 MHz, DMSO-d$_6$): δ 1.25-1.41 (2H, m), 1.67 (1H, m), 1.87-1.92 (3H, m), 2.29-2.45 (3H, m), 4.97 (1H, m), 7.37 (1H, d, J=3.6 Hz), 7.55 (1H, d, J=3.6 Hz), 7.62 (1H, s), 7.77-7.85 (2H, m), 8.11-8.18 (2H, m), 12.18 (1H, s); APCI-MS: 481.47; HPLC: 95%.

Example 6

3-{5-[1-[5-(2-chloro-phenyl)-furan-2-yl]-methylidene]-4-oxo-2-thioxo-thiazolidin-3-yl}-cyclohexanecarboxylic acid, (Compound C1)

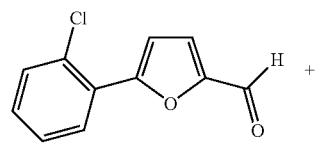

A mixture of 3-(4-oxo-2-thioxo-thiazolidin-3-yl)-cyclohexanecarboxylic acid (0.038 g, 0.15 mmol), 5-(2-chlorophenyl)-furan-2-carbaldehyde (0.033 g, 0.16 mmol) (purchased from Aldrich Chemical Company) and ethylenediamine diacetate (0.029 g, 0.16 mmol) in ethanol (5 mL) was heated to 60° C. for 4 h. The mixture was poured into ethyl acetate (250 mL) and washed with 0.6 N aq sodium hydrogensulfite (2×50 mL). The organic layer was isolated, dried over anhydrous sodium sulfate and concentrated under reduced pressure. The crude material was triturated with a mixture of ether (1 mL) and hexanes (3 mL). The product was filtered off and dried in a vacuum oven at 60° C. for 17 h to afford 3-{5-[1-[5-(2-chloro-phenyl)-furan-2-yl]-methylidene]-4-oxo-2-thioxo-thiazolidin-3-yl}-cyclohexanecarboxylic acid as a solid (44 mg, 67%). H NMR (400 MHz, DMSO-d$_6$): δ 1.25-1.31 (1H, m), 1.34-1.41 (1H, m), 1.69 (1H, m), 1.90 (3H, m), 2.28-2.45 (3H, m), 4.95 (1H, m), 7.40 (1H, d, J=3.6), 7.43 (1H, d, J=3.6), 7.46 (1H, m), 7.62 (1H, s), 7.62 (2H, m), 7.92 (1H, m), 12.22 (1H s). LC/MS: APCI 447.33, HPLC 100%.

Example 7

2-{5-[1-[5-(5-tert-Butyl-2-hydroxy-phenyl)-furan-2-yl]-methylidene]-4-oxo-2-thioxo-thiazolidin-3-ylamino}-benzoic acid; (Compound D5)

Part A: 5-(5-tent-butyl-2-hydroxy-phenyl)-furan-2-carbaldehyde

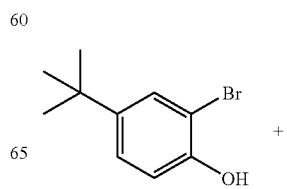

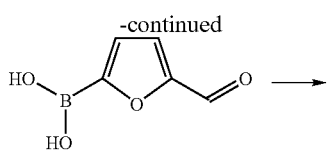

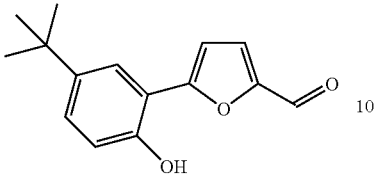

A reaction flask was flushed with nitrogen and charged with 2-bromo-4-tert-butyl-phenol (2.019 g, 8.81 mmol), 5-formyl-furan-2-boronic acid (1.831 g, 13.09 mmol) and sodium carbonate (2.783 g, 26.26 mmol). A mixture of 1,2-dimethoxyethane (40 mL) and water (13 mL) was added and the reaction mixture was stirred for 10 min under a nitrogen atmosphere. Dichlorobis(triphenylphosphine) palladium(II) (0.193 g, 0.27 mmol) was added and the mixture was stirred and heated to 65° C. for 17 h. The mixture was cooled to room temperature, diluted with methyl tert-butyl ether (MTBE) (250 mL) and washed successively with 5% aq. potassium carbonate (100 mL), water (100 mL) and brine. The organic layer was separated, dried over sodium sulfate and concentrated under reduced pressure. The residue was chromatographed on flash Silica (100 g, 5 to 10% ethyl acetate in hexanes) to afford 5-(5-tert-butyl-2-hydroxy-phenyl)-furan-2-carbaldehyde (160 mg, 7%). $^1$H NMR (400 MHz, CDCl$_3$): δ 1.33 (9H, s) 6.51 (1H, bs), 6.90 (1H, d, J=8.8 Hz), 7.03 (1H, d, J=4.0 Hz), 7.32 (1H, dd, J=8.8, 2.4 Hz), 7.36 (1H, d, J=3.6 Hz), 7.73 (1H, d, J=3.2 Hz), 9.64 (1H, s). ESI-MS: 243.0.

Part B: 2-bromo-4-tert-butyl-phenol

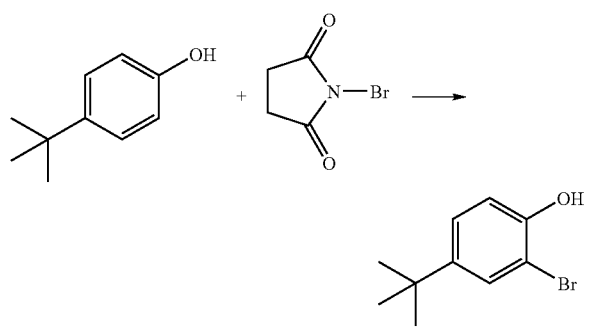

A solution of 4-tert-butyl-phenol (5.070 g, 33.75 mmol) in DCM (200 mL) was cooled in ice-water bath. N-bromosuccinimide (5.020 g, 28.20 mmol) was added to the solution in three equal portions in 30 min intervals. The mixture was allowed to reach room temperature and was stirred for an additional 3 h. The mixture was concentrated under reduced pressure and the residue was triturated with MTBE (300 mL). The solid material was filtered off and the filtrate was washed with water (3×300 mL). The organic layer was separated, dried over sodium sulfate and concentrated to yield 8.3 g of oily residue. A 3.0 g sample of the residue was chromatographed on flash Silica (100 g), eluted with 10% DCM in hexanes to afford 2-bromo-4-tert-butyl-phenol (2.33 g, 83%).

$^1$H NMR (400 MHz, CDCl$_3$): δ 1.28 (9H, s), 5.37 (1H, bs), 6.95 (1H, d, J=8.4 Hz), 7.24 (1H, dd, J=8.4, 2.8 Hz), 7.44 (1H, d, J=2.8 Hz). ESI-MS: 227.2.

Part C: 2-(4-oxo-2-thioxo-thiazolidin-3-ylamino)-benzoic acid

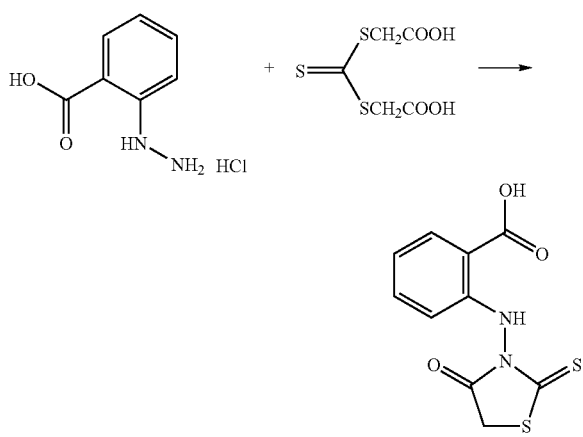

To a water (20 mL) solution of 2-hydrazino-benzoic acid hydrochloride (2.508 g, 13.30 mmol) was added water solution of sodium hydroxide (1.029 N, d=1.040, 26.81 g, 26.60 mmol) followed by bis(carboxymethyl)trithiocarbonate (3.006 g, 13.28 mmol). The mixture was stirred at reflux temperature for 10 h, cooled to room temperature and stirred for 50 h. The solid product was filtered off and washed on funnel successively with water (2×10 ml), ether (5 mL) and hexane (20 mL). The material was dried in a vacuum oven at 80° C. for 5 h to afford 2-(4-oxo-2-thioxo-thiazolidin-3-ylamino)-benzoic acid (2.93 g, 82%) as a solid. $^1$H NMR (400 MHz, DMSO-d$_6$): δ 4.33 (1H, bs), 6.66 (1H, m), 6.90 (1H, m), 7.40 (1H, m), 7.89 (1H, m), 13.37 (1H, bs). ESI-MS: 267.0.

Part D: 2-{5-[1-[5-(5-tert-Butyl-2-hydroxy-phenyl)-furan-2-yl]-methylidene]-4-oxo-2-thioxo-thiazolidin-3-ylamino}-benzoic acid

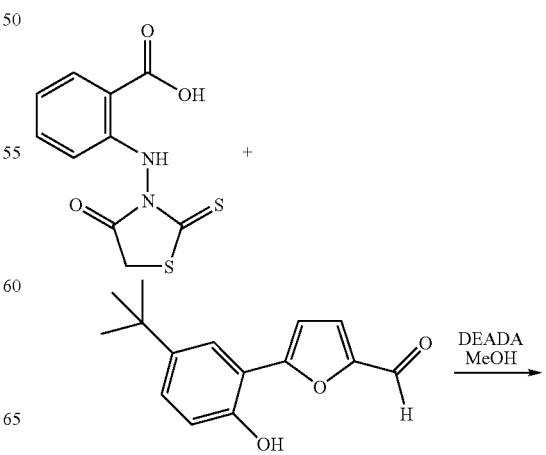

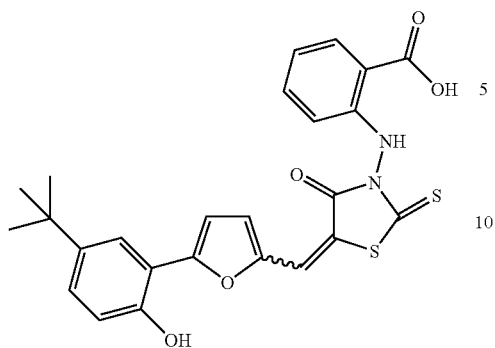

A mixture of 2-(4-oxo-2-thioxo-thiazolidin-3-ylamino)-benzoic acid (0.078 g, 0.29 mmol), 5-(5-tert-butyl-2-hydroxy-phenyl)-furan-2-carbaldehyde and (0.075 g, 0.31 mmol) and ethylenediamine diacetate (0.056 g, 0.031 mmol) in methanol (10 mL) was stirred at room temperature for 18 h. The reaction mixture was poured into stirred 0.6 N aq sodium hydrogensulfite (50 mL). The mixture was vigorously stirred for 30 min. The solid product was filtered off and washed on funnel successively with 0.6 N aq sodium hydrogensulfite (1 mL), water (2×2 mL), ether (2×1 mL) and hexanes (2 mL). The material was dried in a vacuum oven at 65° C. for 17 h to afford 2-{5-[1-[5-(5-tert-Butyl-2-hydroxy-phenyl)-furan-2-yl]-methylidene]-4-oxo-2-thioxo-thiazolidin-3-ylamino}-benzoic acid (135 mg, 94%) as a solid. $^1$H NMR (400 MHz, DMSO-d$_6$): δ 1.37 (9H, s), 6.98 (1H, d, J=8.4 Hz), 7.23 (1H, d, J=3.6 Hz), 7.34 (1H, dd, J=8.8, 2.8 Hz), 7.39 (1H, d, J=3.6 Hz), 7.70 (2H, m), 7.74 (1H, s), 7.94 (1H, d, J=2.4 Hz), 8.01 (1H, m), 8.07 (1H, m). LC/MS. APCI 493.1, HPLC 100%.

Example 8

2-{5-[1-[5-(2-Chloro-phenyl)-furan-2-yl]-methylidene]-4-oxo-2-thioxo-thiazolidin-3-ylamino}-benzoic acid; (Compound D1)

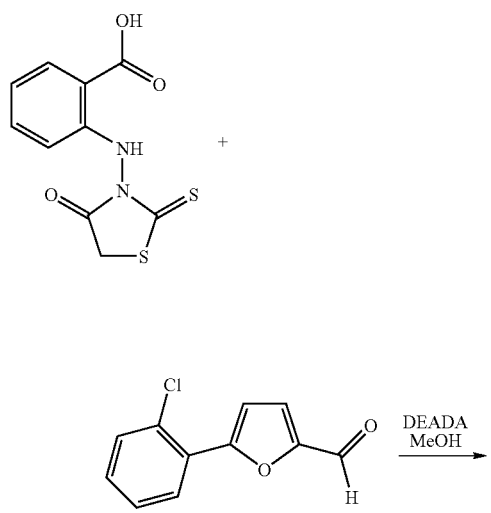

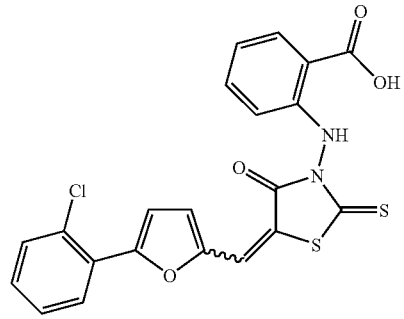

A mixture of 2-(4-oxo-2-thioxo-thiazolidin-3-ylamino)-benzoic acid (0.090 g, 0.34 mmol), 5-(2-chloro-phenyl)-furan-2-carbaldehyde (0.074 g, 0.36 mmol) (purchased from Aldrich Chemical Co.) and ethylenediamine diacetate (0.065 g, 0.036 mmol) in methanol (8 mL) was stirred at room temperature for 17 h. The reaction mixture was poured into stirred 0.6 N aq sodium hydrogensulfite (50 mL). The mixture was vigorously stirred for 15 min. The solid product was filtered off and washed on funnel successively with 0.6 N aq sodium hydrogensulfite (2 mL), water (2×2 mL), ether (2 mL) and hexanes (2 mL). The material was dried in a vacuum oven at 65° C. for 19 h to afford 2-{5-[1-[5-(2-Chloro-phenyl)-furan-2-yl]-methylidene]-4-oxo-2-thioxo-thiazolidin-3-ylamino}-benzoic acid (141 mg, 92%) as a solid. $^1$H NMR (400 MHz, DMSO-d$_6$): δ 6.55 (1H, d, J=8.0 Hz), 6.87 (1H, t, J=7.6 Hz), 7.32 (1H, t, J=7.6 Hz), 7.44-7.51 (3H, m), 7.62 (1H, d, J=8.0 Hz), 7.66 (1H, d, J=8.4 Hz), 7.80 (1H, s), 7.91 (1H, d, J=8.0 Hz), 7.97 (1H, d, J=8.0 Hz). LC/MS: APCI 457.2, HPLC 97.9%

Example 9

2-{5-[1-[5-(4-tert-Butyl-phenyl)-furan-2-yl]-meth-(E)-ylidene]-4-oxo-2-thioxo-thiazolidin-3-ylamino}-benzoic acid; (Compound D2)

Part A: 5-(4-tert-butyl-phenyl)-furan-2-carbaldehyde

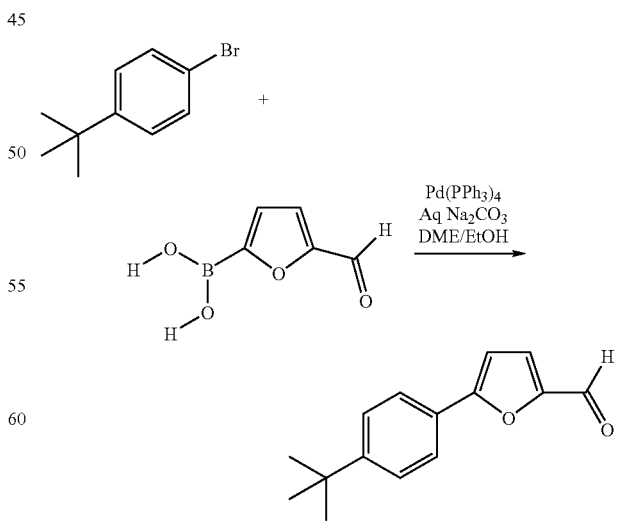

To a round bottom flask containing 1-bromo-4-tert-butyl-benzene (1.5 g, 7.04 mmol) and 5-formyl-2-furan-boronic acid (1.47 g, 10.56 mmol) in dimethoxyethane (80 mL) and ethanol (20 mL) was added an aqueous solution of sodium carbonate (2.24 g, 21.12 mmol) in water (30 mL) The reaction mixture was stirred at room temperature for 5 minutes, followed by the addition of tetrakis(triphenylphosphine)palladium (404 mg, 0.35 mmol). The reaction mixture was heated at 70° C. for 1 h. The reaction mixture was then cooled to room temperature and diluted with ethyl acetate (500 mL) and water (50 mL). The layers were separated and the aqueous layer was extracted with ethyl acetate (2×150 mL). The combined organic extracts were washed with brine, dried (sodium sulfate) and concentrated under vacuum. The crude product was purified by silica gel chromatography eluting with 20% ethyl acetate in hexanes to afford 5-(4-tert-butyl-phenyl)-furan-2-carbaldehyde (1:16 g, 72%) as a dark brown solid. $^1$H NMR (400 MHz, CDCl$_3$): δ 1.35 (9H, s), 6.80 (1H, d, J=3.6 Hz), 7.31 (1H, d, J=3.6 Hz), 7.44-7.7.48 (2H, m), 7.74-7.77 (2H, m), 9.64 (1H, s); APCI-MS: 228.34.

Part B: 2-{5-[1-[5-(4-tert-Butyl-phenyl)-furan-2-yl]-meth-(E)-ylidene]-4-oxo-2-thioxo-thiazolidin-3-ylamino}-benzoic acid

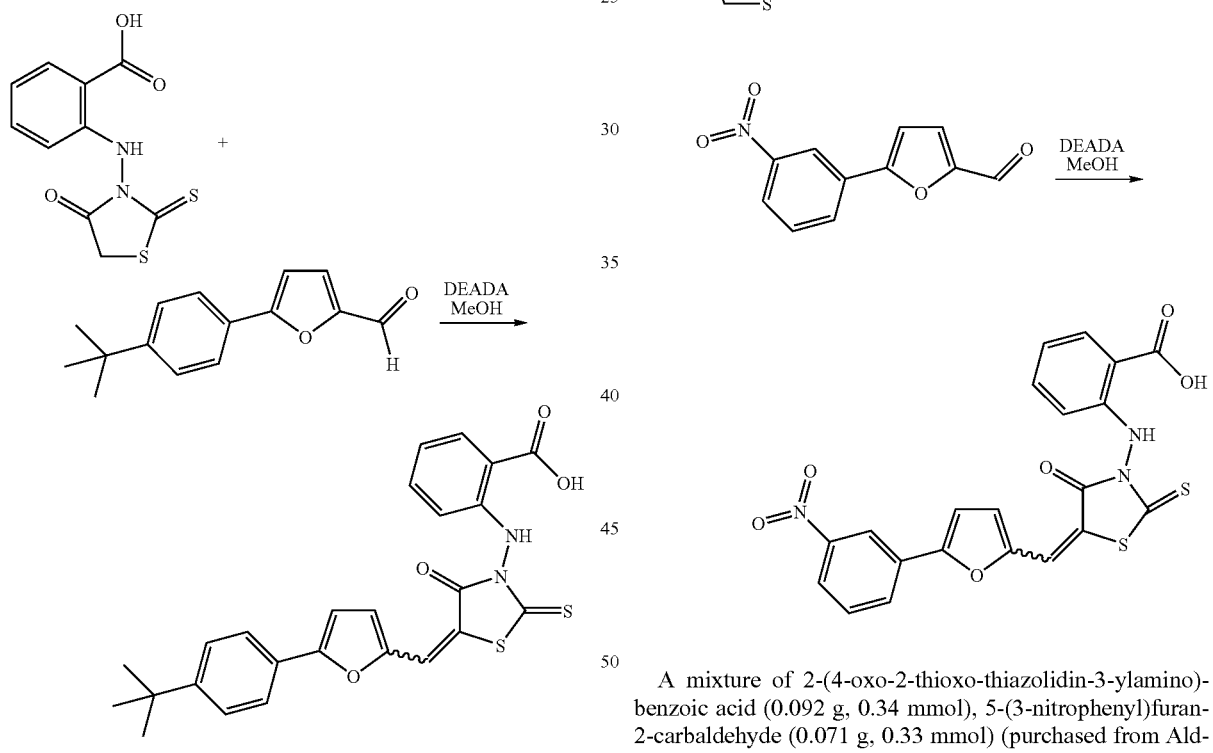

A mixture of 2-(4-oxo-2-thioxo-thiazolidin-3-ylamino)-benzoic acid (0.090 g, 0.34 mmol), 5-(4-tert-butyl-phenyl)-furan-2-carbaldehyde (0.082 g, 0.36 mmol) and ethylenediamine diacetate (0.065 g, 0.036 mmol) in methanol (8 mL) was stirred at room temperature for 17 h. The reaction mixture was poured into stirred 0.6 N aq sodium hydrogensulfite (50 mL). The mixture was vigorously stirred for 15 min. The solid product was filtered off and washed on funnel successively with 0.6 N aq sodium hydrogensulfite (2 mL), water (2×2 mL), ether (2 mL) and hexanes (2 mL). The material was dried in a vacuum oven at 65° C. for 19 h to afford 2-{5-[1-[5-(4-tert-Butyl-phenyl)-furan-2-yl]-meth-(E)-ylidene]-4-oxo-2-thioxo-thiazolidin-3-ylamino}-benzoic acid (140 mg, 87%) as a solid. $^1$H NMR (400 MHz, DMSO-d$_6$): δ 1.32 (9H, s), 6.45 (1H, m), 6.82 (1H, m), 7.23 (1H, m), 7.30 (1H, d, J=3.6), 7.40 (1H, d, J=3.6), 7.61 (2H, m), 7.74 (1H, s), 7.82 (2H, m), 7.91 (1H, m), 11.20 (1H, bs). LC/MS APCI 477.9, HPLC 91.0%

Example 10

2-{5-[1-[5-(3-Nitro-phenyl)-furan-2-yl]-methylidene]-4-oxo-2-thioxo-thiazolidin-3-ylamino}-benzoic acid; (Compound D4)

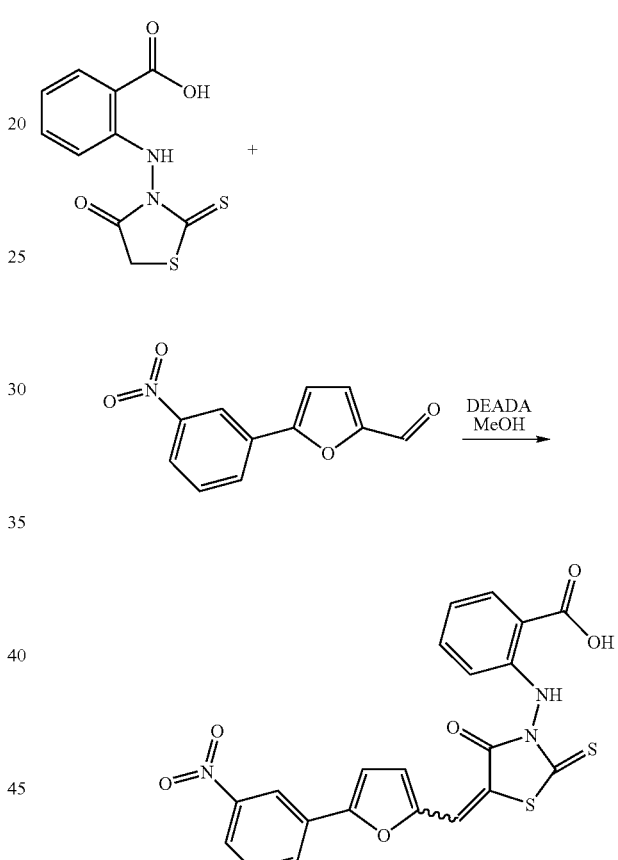

A mixture of 2-(4-oxo-2-thioxo-thiazolidin-3-ylamino)-benzoic acid (0.092 g, 0.34 mmol), 5-(3-nitrophenyl)furan-2-carbaldehyde (0.071 g, 0.33 mmol) (purchased from Aldrich Chemical Company) and ethylenediamine diacetate (0.059 g, 0.033 mmol) in methanol (10 mL) was stirred at room temperature for 18 h. The reaction mixture was poured into stirred 0.6 N aq sodium hydrogensulfite (50 mL). The mixture was vigorously stirred for 30 min. The solid product was filtered off and washed on funnel successively with 0.6 N aq sodium hydrogensulfite (1 mL), water (2×2 mL), acetonitrile (1 mL), ether (2×2 mL) and acetonitrile (1 mL). The material was dried in a vacuum oven at 65° C. for 17 h to afford 2-{5-[1-[5-(3-Nitro-phenyl)-furan-2-yl]-methylidene]-4-oxo-2-thioxo-thiazolidin-3-ylamino}-benzoic acid (115 mg, 72%) as a solid. $^1$H NMR (400 MHz, DMSO-d$_6$): δ 6.62 (1H, m), 6.90 (1H, m), 7.37 (1H, m), 7.44 (1H, d, J=3.6 Hz), 7.64 (1H, d, J=3.6 Hz), 7.80 (1H, s), 7.88 (1H, m), 7.92 (1H, m), 8.28 (2H, m), 8.65 (1H, m), 10.2 (1H, bs). LC/MS: APCI 466.7, HPLC 96.5%

Example 11

2-{4-Oxo-2-thioxo-5-[1-[5-(3-trifluoromethyl-phenyl)-furan-21]-methylidene]-thiazolidin-3-ylamino}-benzoic acid; (Compound D3)

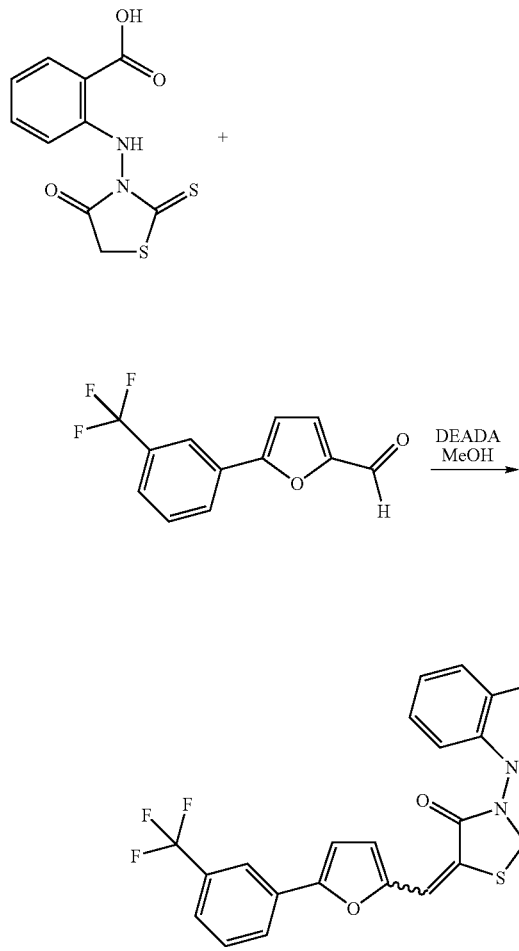

A mixture of 2-(4-oxo-2-thioxo-thiazolidin-3-ylamino)-benzoic acid (0.090 g, 0.34 mmol), 5-(3-trifluoromethyl-phenyl)-furan-2-carbaldehyde (0.086 g, 0.36 mmol) (purchased from Aldrich Chemical Company) and ethylenediamine diacetate (0.065 g, 0.036 mmol) in methanol (8 mL) was stirred at room temperature for 17 h. The reaction mixture was poured into stirred 0.6 N aq sodium hydrogensulfite (50 mL). The mixture was vigorously stirred for 15 mm. The solid product was filtered off and washed on funnel successively with 0.6 N aq sodium hydrogensulfite (2 mL), water (2×2 mL), ether (2 mL) and hexanes (2 mL). The material was dried in a vacuum oven at 65° C. for 19 h to afford 2-{4-Oxo-2-thioxo-5-[1-[5-(3-trifluoromethyl-phenyl)-furan-2-yl]-methylidene]-thiazolidin-3-ylamino}-benzoic acid (130 mg, 79%) as a solid. $^1$H NMR (400 MHz, DMSO-d$_6$): δ 6.53 (1H, m), 6.86 (1H, m), 7.29 (1H, m), 7.43 (1H, d, J=3.6 Hz), 7.59 (1H, d, J=3.6 Hz), 7.78 (1H, s), 7.82 (2H, m), 7.92 (1H, m), 8.16 (1H, m), 8.21 (1H, m). LC/MS: APCI 489.3, HPLC 97.1%

Example 12

2-{5-[1-[5-(4-morpholin-4-yl-phenyl)-furan-2-yl]-meth-(E)-ylidene]-4-oxo-2-thioxo-thiazolidin-3-ylamino}-benzoic acid; (Compound D6)

Part A:
5-(4-morpholin-4-yl-phenyl)-furan-2-carbaldehyde

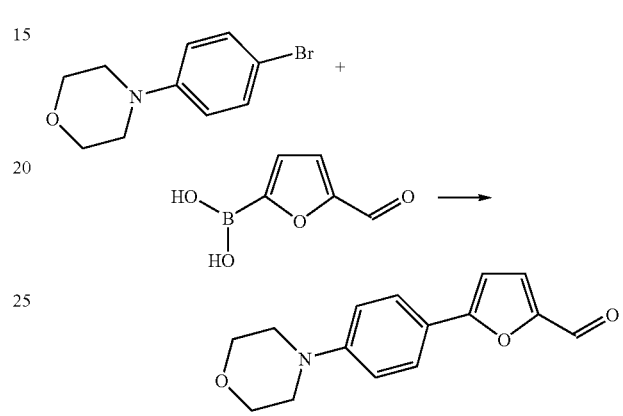

The reaction flask was flushed with nitrogen and charged with 4-(4-bromo-phenyl)-morpholine (2.134 g, 8.81 mmol), 5-formyl-furan-2-boronic acid (1.832 g, 13.10 mmol) and sodium carbonate (3.016 g, 28.46 mmol). A mixture of 1,2-dimethoxyethane (35 mL), ethanol (10 mL) and water (13 mL) was added and the reaction mixture was stirred for 10 min under a nitrogen atmosphere. Dichlorobis(triphenylphosphine) palladium(II) (0.205 g, 0.29 mmol) was added and the mixture was stirred and heated at 80° C. for 18 h. The mixture was cooled to room temperature and partitioned between ether (250 mL) and water (100 mL). The organic layer was separated, dried over sodium sulfate and concentrated under reduced pressure. The residue was chromatographed on flash Silica (100 mL, 20% ethyl acetate in hexanes) to afford 5-(4-morpholin-4-yl-phenyl)-furan-2-carbaldehyde (1.36 g, 60%). $^1$H NMR (400 MHz, CDCl$_3$): δ 3.26 (2H, dd, J=5.2, 3.6 Hz), 3.87 (2H, dd, J=5.2, 3.6 Hz), 6.69 (1H, d, J=4.0 Hz), 6.93 (2H, m), 7.26 (1H, s), 7.30 (1H, d, J=4.0), 7.74 (2H, m), 9.58 (1H, s). ESI-MS: 258.0.

Part B: 2-{5-[1-[5-(4-morpholin-4-yl-phenyl)-furan-2-yl]-meth-(E)-ylidene]-4-oxo-2-thioxo-thiazolidin-3-ylamino}-benzoic acid

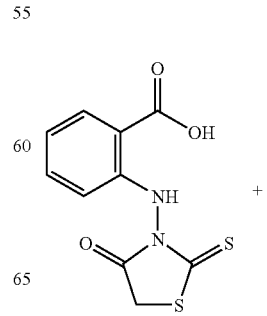

-continued

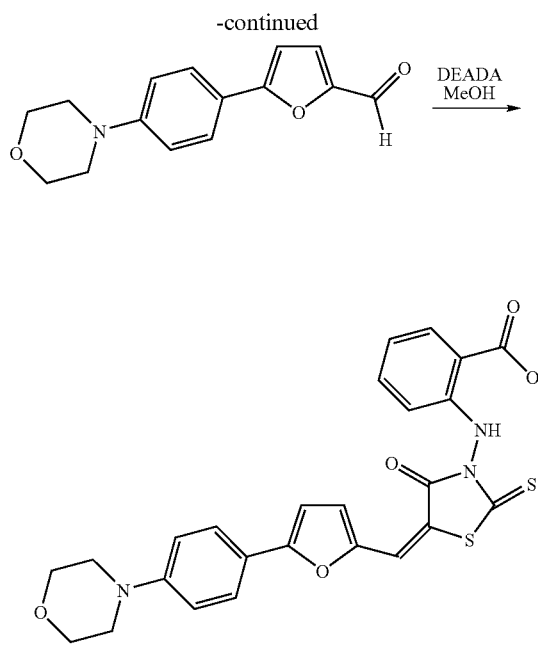

A mixture of 2-(4-oxo-2-thioxo-thiazolidin-3-ylamino)-benzoic acid (0.089 g, 0.33 mmol), 5-(4-morpholin-4-yl-phenyl)-furan-2-carbaldehyde (0.091 g, 0.35 mmol) and ethylenediamine diacetate (0.063 g, 0.035 mmol) in methanol (10 mL) was stirred at room temperature for 18 h. The reaction mixture was poured into stirred 0.6 N aq sodium hydrogensulfite (50 mL). The mixture was vigorously stirred for 30 mm. The solid product was filtered off and washed on funnel successively with 0.6 N aq sodium hydrogensulfite (1 mL), water (2×2 mL), ether (2×1 mL) and hexanes (2 mL). The material was dried in a vacuum oven at 65° C. for 17 h to afford 2-{5-[1-[5-(4-morpholin-4-yl-phenyl)-furan-2-yl]-meth-(E)-ylidene]-4-oxo-2-thioxo-thiazolidin-3-ylamino}-benzoic acid (147 mg, 87%) as a solid. $^1$H NMR (400 MHz, DMSO-$d_6$): 3.26 (2H, m), 3.76 (2H, m), 6.53 (1H, d, J=8.4 Hz), 6.87 (1H, m), 7.14 (2H, m), 7.17 (1H, d, J=3.6 Hz), 7.31 (1H, m), 7.40 (1H, d, J=4.0 Hz), 7.71 (1H, s), 7.76 (2H, m), 7.91 (1H, m), 10.4 (1H, bs). LC/MS: APCI 506.1, HPLC 92%.

Example 13

Synthesis of (3-[-[[5-(2-chlorophenyl)-2-furanyl]methylene]-4-oxo-2-thioxo-3-thiazolidinyl]benzoic acid) (Mycopyrin 5, Compound A1)

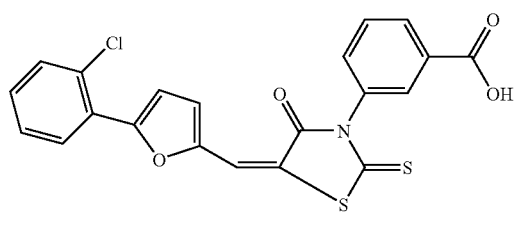

Part A: Synthesis of 3-(4-oxo-2-thioxo-thiazolidin-3-yl)-benzoic acid

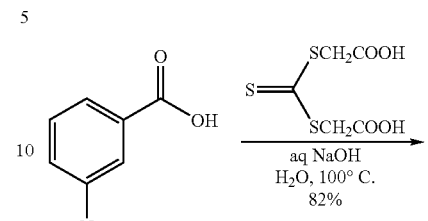

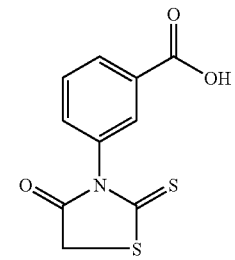

Molecular Weight = 253.30
Molecular Formula = $C_{10}H_7NO_3S_2$
3-(4-Oxo-2-thioxo-thiazolidin-3-yl)-benzoic acid 3-amino-benzoic acid (6.00 g, 43.77 mmol), bis(carboxymethyl)trithiocarbonate (10.2 g, 45.09 mmol) in 1.029 N aqueous sodium hydroxide (44.5 g, 44.06 mmol) was heated at 100° C. for 16 h. The reaction mixture was cooled to room temperature. The precipitated solid was filtered, washed successively with 3N aqueous HCl (3×20 mL), water (3×20 mL), ethanol (2×20 mL) and dried in vacuum oven at 60° C. for 2 h to obtain 3-(4-oxo-2-thioxo-thiazolidin-3-yl)-benzoic acid (9.10 g, 82%) as a white solid. $^1$H NMR (400 MHz, DMSO-d6): δ 4.34 (2H, s), 7.52-7.55 (1H, m), 7.67 (1H, t, J=8 Hz), 7.87 (1H, t, J=2 Hz), 8.02-8.05 (1H, dt, J=1.2 & 2.8 Hz); ESI-MS: 253.30.

Part B: Synthesis of 3-[-[[5-(2-chlorophenyl)-2-furanyl]methylene]-4-oxo-2-thioxo-3-thiazolidinyl]benzoic acid

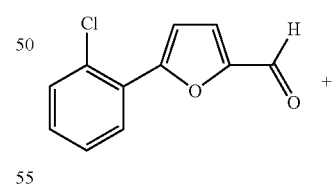

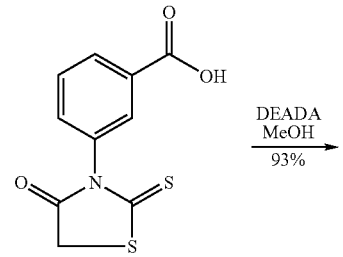

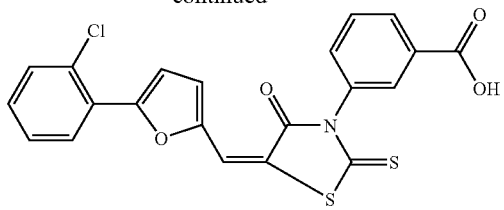

5-(2-chloro-phenyl)-furan-2-carbaldehyde (6.00 g, 29 mmol) (purchased from Aldrich Chemical Company, Milwaukee, Wis., USA) and ethylenediamine diacetate (5.23 g, 29 mmoL) was added to a solution of 3-(4-oxo-2-thioxo-thiazolidin-3-yl)-benzoic acid (7.00 g, 27.64 mmol) in methanol (120 mL). The reaction mixture was stirred at room temperature for 69 h. The precipitated solid was filtered, washed successively with methanol (1×100 mL), water (2×50 mL), 0.6 N NaHSO$_3$ (2×50 mL), water (2×50 mL), hexanes (1×500 mL) and dried in vacuum oven at 70° C. for 21 h to obtain 12.18 g (99%) of product. $^1$H NMR revealed desired product to be contaminated with minor impurities. To 12 g of the above solid added methanol (150 mL) and stirred at room temperature for 30 min. The solid was filtered, washed with methanol (50 mL), hexanes (400 mL) and dried in vacuum oven at 70° C. for 21 h to obtain 3-[-[[5-(2-chlorophenyl)-2-furanyl]methylene]-4-oxo-2-thioxo-3-thiazolidinyl]benzoic acid (11.33 g, 93%) as a bright orange-red solid: mp 230° C. dec; $^1$H NMR (400 MHz, DMSO-d6): δ 7.44 (1H, d, J=4 Hz), 7.47-7.52 (2H, m), 7.57-7.68 (4H, m), 7.77 (1H, s), 7.94 (1H, t, J=1.6 Hz), 7.99 (1H, dd, J=4 & 8 Hz), 8.05 (1H, dt, J=1.2 & 2.8 Hz); APCI-LC/MS: 441.92; HPLC; 96%.

Protocol for In Vivo Studies of Compounds of Formula I

*M. tuberculosis* ("Mtb", H37Rv strain; American Type Culture Collection, Rockville, Md.) were passed through mice, and grown in Middlebrook 7H9 medium (Difco) supplemented with 0.2% glycerol, 0.05% Tween-80, 0.5% bovine serum albumin, 0.2% dextrose and 0.085% sodium chloride (7H9-ADN). Mtb solid media used Middlebrook 7H11 agar supplemented with Middlebrook Enrichment (oleic acid, albumin, dextrose, and catalase). Mtb was pelleted by centrifugation and resuspended in PBS containing 0.05% Tween-80 ("PBS-Tween-80"). Glycerol was added to a final concentration of 10%, and the bacterial suspension was aliquoted, frozen and stored at –80° C. Viable bacterial counts were determined by plating serial 10-fold dilutions on Middlebrook 7H10 (Difco) agar plates.

To prepare bacteria for aerosol infection, Mtb from mid logarithmic phase cultures (OD$_{580}$ of 0.4) were centrifuged in 50 ml conical tubes at 3,310×g for 8 minutes at room temperature. Pellets were resuspended in a half-volume of PBS/Tween and then were centrifuged at 130×g for 8 minutes. The OD$_{580}$ of the supernatant was measured and the suspension was diluted to an OD$_{580}$ of 0.04 in PBS. $10^8$ CFU were placed into the nebulizer of a Glas-Col Inhalation Exposure System (Terre Haute, Ind.). Each mouse received ~100-200 bacilli. This number was determined in 3 mice one day after infection by counting colony-forming units (CFU) recovered from the lungs. To enumerate Mtb in the organs of the infected animals, four to five mice per time point were used, and each experiment was performed at least twice. Mice were killed using carbon dioxide inhalation. Organs were homogenized in phosphate buffered saline/0.05% Tween 80 (PBS/Tween) and serial 10-fold dilutions were plated on 7H11 agar enriched with 10% OADC (Difco, Mich., USA). Plates were incubated at 37° C. and colonies are enumerated after 21-28 days.

Identification of acid-fast bacilli (AFB) was performed on formalin-fixed tissue sections using Ziehl-Neelsen staining and counterstaining in Mayer's Hematoxylin (VWR).

Bacterial loads and cell populations in tuberculosis granulomas of Mtb-infected mice were compared using 1-test (GraphPad Prizm, version 3.0). Results are presented as the mean±s.d. A threshold for statistical significance is P<0.05.

The day of aerosol infection of 25 mice was deemed day 0. On day 21, 5 mice were euthanatized to determine number of colony forming units (CFU) at the time point shown in previous work to represent the onset of what would be a stable bacterial burden for the next year or more and the time point chosen for the onset of therapy. The remaining 20 mice were treated with either inhibitor (10 mice, treatment group) or vehicle alone (no inhibitor) (10 mice, control group) given as a once-daily treatment by gavage or by intraperitoneal injection for 14 days. On day 35, 5 of the treated mice and 5 of the untreated mice were euthanatized for determination of CFU and histology. The 10 remaining mice continued for another 14 days on the same regimen as before: with either inhibitor (5 mice, treatment group) or vehicle alone (no inhibitor) (5 mice, control group) given as a once-daily treatment by gavage or by intraperitoneal injection, and were euthanatized on day 49 for determination of CFU and histology.

A principal element of host immunity to Mtb is production of reactive nitrogen intermediates (RNI) (C. Nathan, S. Ehrt, in *Tuberculosis*, W. Rom, S. M. Garay, Eds. (Lippincott Williams & Wilkins, Philadelphia, 2004) pp. 215-235; J. Flynne, J. Chan, in *Nitric Oxide and Infection* F. Fang, Ed. (Kluwer Academic/Plenum Publishers, New York, 1999, pp. 281-310). RNI have both nitrosative and oxidative actions (St John et al., *Proc Natl Acad Sci USA* 98, 9901-6, 2001). One mycobacterial defense against RNI and reactive oxygen intermediates is a 4-component peroxynitrite reductase/peroxidase consisting of alkylhydroperoxide reductase (Ahp) subunit C (AhpC), Ahp subunit D (AhpD), DlaT (formerly, SucB) and lipoamide dehydrogenase (Lpd) (R. Bryk, Griffin, P. and Nathan, C., *Nature* 407, 211-215, 2000; R. Bryk, Lima, C. D., Erdjument-Bromage, H., Tempst, P. and Nathan, C., *Science* 295, 1073-1077, 2002). DlaT and Lpd also serve as the E2 and E3 components, respectively, of Mtb's PDH (Tian, J., R. Bryk, S. Shi, H. Erdjument-Bromage, P. Tempst and C. Nathan, *Mycobacterium tuberculosis* appears to lack α-ketoglutarate dehydrogenase and encodes pyruvate dehydrogenase in widely separated genes. *Molec. Microbial.* 57: 859-868, 2005; Tian, J., R. Bryk, M. Itoh, M. Suematsu and C. Nathan, Variant tricarboxylic acid cycle in *Mycobacterium tuberculosis*: Identification of α-ketoglutarate decarboxylase. *Proc. Natl. Acad. Sci.* 102:10670-10675, 2005). PDH supplies substrate to the citric acid cycle for generation of high-energy phosphate bonds, reducing equivalents and precursors of amino acids and heme, and generates acetyl coenzyme A for net synthesis of the long-chain lipids in Mtb's cell wall. Thus, DlaT and Lpd play a pivotal role in intermediary metabolism and can contribute directly and indirectly to defense against nitrosative and oxidative injury.

In vitro, RNI can be generated under physiologically relevant conditions by provision of nitrite at a mildly acidified pH. During infection, Mtb resides chiefly in the phagosome of macrophages, where the pH is ~6 in immunologically non-activated cells and can fall to ~4.5 in those that have been activated by interferon-γ. Activated macrophages produce RNI, the most abundant of which is the accumulating autoxidation product of NO, nitrite (NO$_2^-$). In the present assay, the intraphagosomal milieu of moderately activated macrophages was partially mimicked by culturing mycobacteria at pH 5.5 with nitrite. Mildly acidic nitrite kills Mtb in a concentration- and time-dependent manner but was used in this assay at sublethal concentrations. At pH 5.5, 0.5 mM nitrite generates an amount of NO no greater than that released by $3\times10^5$ activated macrophages in 0.5 mL in 24 hours. In the present assay pH 5.5, with or without 0.5 mM nitrite, was used.

In the tables below, the activity is set forth as a category "A", "B" or "C". When the DIat $IC_{50}$ is below 10 μM, the compound is category A, when the DIat $IC_{50}$ is 11-40 μM, the compound is B; when the DIat $IC_{50}$>41-80 μM the compound is C. In the tables, when a group "Het" is identified as e.g. "2,4-thiazole" or "2,5-furan", the first number refers to the point of attachment of "Het" to the olefin bond which is exo to the rhodanine ring, and the second number refers to the place where -Q-R is attached to "Het". Thus, in a compound which "Het" is identified in the tables as "2,4-thiazole" and A is O, the structure is:

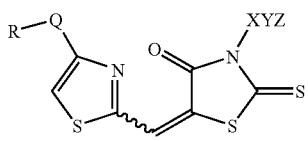

TABLE 1

(Compounds A1 to A294)

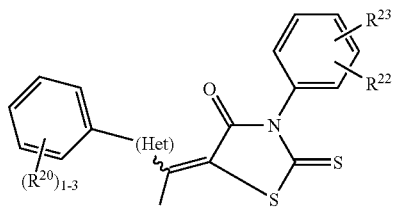

DIat $IC_{50}$ < 10 μM = A;
DIat $IC_{50}$ 11-40 μM = B;
DIat $IC_{50}$ > 41 μM = C

| Compound | $R^{20}$ | Het | $R^{22}$ | $R^{23}$ | DIat $IC_{50}$ category |
|---|---|---|---|---|---|
| A1 | 2-Cl | 2,5-furan | 3-COOH | H | B |
| A2 | 3-$CF_3$ | 2,5-furan | 3-COOH | H | A |
| A3 | 4-$CH_2$Ph | 2,5-furan | 3-COOH | H | A |
| A4 | 3-Cl | 2,5-furan | 3-COOH | H | B |
| A5 | 2-Cl | 2,6-pyridine | 3-COOH | H | C |
| A6 | 2-Cl | 2,5-furan | 4-$SO_2NH_2$ | H | B |
| A7 | 3,4-di-Cl | 2,5-furan | 3-COOH | H | A |
| A8 | 3,4-di-Cl | 2,5-furan | 4-COOH | H | A |
| A9 | 3,4-di-Cl | 2,5-furan | 4-$SO_2NH_2$ | H | B |
| A10 | 3-$CF_3$ | 2,5-furan | 4-COOH | H | B |
| A11 | 4-$CH_2$Ph | 2,5-furan | 4-COOH | H | B |
| A12 | 4-$CH_2$Ph | 2,5-furan | 4-$SO_2NH_2$ | H | B |
| A13 | 4-OPh | 2,5-furan | 3-COOH | H | A |
| A14 | 4-OPh | 2,5-furan | 4-COOH | H | B |
| A15 | 4-OPh | 2,5-furan | 4-$SO_2NH_2$ | H | C |
| A16 | 2-Cl | 2,5-furan | 4-COOH | H | C |
| A17 | 4-Cl | 2,5-furan | 4-$SO_2NH_2$ | H | B |
| A18 | 3-$CF_3$ | 2,5-furan | 4-$SO_2NH_2$ | H | B |
| A19 | 3-Cl | 2,5-furan | 4-$SO_2NH_2$ | H | B |
| A20 | 4-Cl | 2,5-furan | 4-COOH | H | A |
| A21 | 4-Cl | 2,5-furan | 3-COOH | H | A |
| A22 | 2-Cl | 2,5-furan | 4-OH | H | A |
| A23 | 3-$CF_3$ | 2,5-furan | 4-OH | H | A |
| A24 | 4-Cl | 2,5-furan | 4-OH | H | A |
| A25 | 2-Cl | 2,5-furan | 3-$SO_2NH_2$ | H | B |
| A26 | 3-$CF_3$ | 2,5-furan | 3-$SO_2NH_2$ | H | B |
| A27 | 4-Cl | 2,5-furan | 3-$SO_2NH_2$ | H | A |
| A28 | 3-$CF_3$ | 2,4-furan | 3-COOH | H | A |
| A29 | 3-$CF_3$ | 2,4-furan | 4-COOH | H | B |
| A30 | 3,4-di-Cl | 2,5-furan | 4-$SO_2NHCOCH_3$ | H | A |
| A31 | 3-$CF_3$ | 2,5-furan | 4-$SO_2NHCOCH_3$ | H | A |
| A32 | 3-$CF_3$ | 2,5-furan | 3-COOH | 4-OH | A |
| A33 | 2-Cl | 2,5-furan | 3-COOH | 4-OH | A |
| A34 | 4-Cl | 2,5-furan | 3-COOH | 4-OH | A |
| A35 | 2,4-di-Cl | 2,5-furan | 3-COOH | H | B |
| A36 | 2,5-di-Cl | 2,5-furan | 3-COOH | H | A |
| A37 | 2-Cl | 2,5-furan | 3-$SO_2NHCOCH_3$ | H | B |
| A38 | 3-$CF_3$ | 2,5-furan | 3-$SO_2NHCOCH_3$ | H | A |
| A39 | 2,6-di-Cl | 2,5-furan | 3-COOH | H | B |
| A40 | 2,4-di-Cl | 2,5-furan | 3-COOH | 4-OH | B |
| A41 | 2,5-di-Cl | 2,5-furan | 3-COOH | 4-OH | B |
| A42 | 2,6-di-Cl | 2,5-furan | 3-COOH | 4-OH | B |
| A43 | 3-$CF_3$ | 2,5-furan | 3-COOH | H | A |
| A44 | 2-Cl-5-$CF_3$ | 2,5-furan | 3-COOH | H | A |
| A45 | 4-Cl | 2,5-furan | 4-$OCH_2$COOH | H | B |

TABLE 1-continued (Compounds A1 to A294)

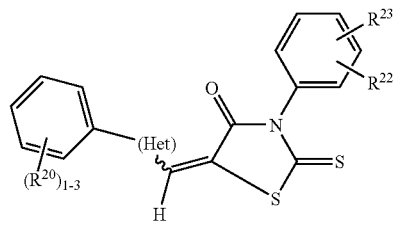

Dlat IC$_{50}$ < 10 μM = A;
Dlat IC$_{50}$ 11-40 μM = B;
Dlat IC$_{50}$ > 41 μM = C

| Compound | R$^{20}$ | Het | R$^{22}$ | R$^{23}$ | Dlat IC$_{50}$ category |
|---|---|---|---|---|---|
| A46 | 4-CH(CH$_3$)$_2$ | 2,5-furan | 3-COOH | H | A |
| A47 | 4-CH(CH$_3$)$_2$ | 2,5-furan | 3-COOH | 4-OH | A |
| A48 | 4-COPh | 2,5-furan | 3-COOH | H | A |
| A49 | 2-Cl | 2,5-furan | 3-OH | H | B |
| A50 | 3-CF$_3$ | 2,5-furan | 3-OH | H | B |
| A51 | 4-Cl | 2,5-furan | 3-OH | H | B |
| A52 | 4-CH(CH$_3$)$_2$ | 2,5-furan | 3-OH | H | B |
| A53 | 4-CH$_2$SPh | 2,5-furan | 3-COOH | H | B |
| A54 | 3-CH(CH$_3$)$_2$ | 2,5-furan | 3-COOH | H | A |
| A55 | 3-CH(CH$_3$)$_2$ | 2,5-furan | 3-OH | H | B |
| A56 | 4-cyclohexyl | 2,5-furan | 3-COOH | H | A |
| A57 | 4-cyclohexyl | 2,5-furan | 3-COOH | 4-OH | A |
| A58 | 4-C(CH$_3$)$_3$ | 2,5-furan | 3-COOH | H | A |
| A59 | 4-C(CH$_3$)$_3$ | 2,5-furan | 3-COOH | 4-OH | A |
| A60 | 4-Cl | 2,5-furan | 3-OCH$_2$COOH | H | B |
| A61 | 3-CH(CH$_3$)$_2$ | 2,5-furan | 3-COOH | 4-OH | A |
| A62 | 4-CH$_2$SPh | 2,5-furan | 3-COOH | 4-OH | B |
| A63 | 3-CH(CH$_3$)$_2$ | 2,5-furan | 3-OCH$_2$COOH | H | A |
| A64 | 4-CH$_2$CH(CH$_3$)$_2$ | 2,5-furan | 3-COOH | H | A |
| A65 | 4-CH$_2$CH(CH$_3$)$_2$ | 2,5-furan | 3-COOH | 4-OH | A |
| A66 | 2-Cl | 2,5-furan | 3-COOH | 4-Cl | A |
| A67 | 3-CF$_3$ | 2,5-furan | 3-COOH | 4-Cl | A |
| A68 | 4-Cl | 2,5-furan | 3-COOH | 4-Cl | A |
| A69 | 2-OCF$_3$ | 2,5-furan | 3-COOH | 4-Cl | A |
| A70 | 2-OCF$_3$ | 2,5-furan | 3-COOH | H | A |
| A71 | 2-Cl | 2,5-furan | 3-COOH | 6-Cl | A |
| A72 | 4-Cl | 2,5-furan | 3-COOH | 6-Cl | A |
| A73 | 3-CF$_3$ | 2,5-furan | 3-COOH | 6-Cl | A |
| A74 | 2-Cl | 2,5-furan | 3-COOH | 6-OCH$_3$ | A |
| A75 | 2-Cl | 2,5-furan | 3-CONH$_2$ | H | B |
| A76 | 3-CF$_3$ | 2,5-furan | 3-CONH$_2$ | H | B |
| A77 | 4-Cl | 2,5-furan | 3-CONH$_2$ | H | B |
| A78 | 2-Cl | 2,5-furan | 3-COOH | 6-CH$_3$ | A |
| A79 | 2-Cl | 2,5-furan | 3-COOH | 2-CH$_3$ | A |
| A80 | 4-C(CH$_3$)$_3$ | 2,5-furan | 3-COOH | 6-CH$_3$ | A |
| A81 | 4-C(CH$_3$)$_3$ | 2,5-furan | 3-COOH | 2-CH$_3$ | A |
| A82 | 4-cyclohexyl | 2,5-furan | 3-COOH | 6-CH3 | A |
| A83 | 4-cyclohexyl | 2,5-furan | 3-COOH | 2-CH$_3$ | A |
| A84 | 4-CH$_2$(4-Cl-Ph) | 2,5-furan | 3-COOH | H | A |
| A86 | 3-CF$_3$ | 2,5-furan | 3-COOH | 6-OCH$_3$ | A |
| A87 | 4-Cl | 2,5-furan | 3-COOH | 6-OCH$_3$ | A |
| A88 | 2-Cl | 2,5-furan | 3-COOH | 5-NO$_2$ | A |
| A89 | 3-CF$_3$ | 2,5-furan | 3-COOH | 5-NO$_2$ | B |
| A90 | 4-Cl | 2,5-furan | 3-COOH | 5-NO$_2$ | A |
| A91 | 4-CH$_2$CH(CH$_3$)$_2$ | 2,5-furan | 3-COOH | 6-OCH$_3$ | A |
| A92 | 4-CH$_2$CH(CH$_3$)$_2$ | 2,5-furan | 3-COOH | 6-Cl | A |
| A93 | 3-CH(CH$_3$)$_2$ | 2,5-furan | 3-COOH | 6-OCH$_3$ | A |
| A94 | 4-cyclopentyl | 2,5-furan | 3-COOH | H | A |
| A95 | 4-C(CH$_3$)$_2$Ph | 2,5-furan | 3-COOH | H | A |
| A96 | 4-C(CH$_3$)$_2$Ph | 2,5-furan | 3-COOH | 6-Cl | A |
| A97 | 4-C(CH$_3$)$_2$Ph | 2,5-furan | 3-COOH | 6-OCH$_3$ | B |
| A98 | 4-C(CH$_3$)$_2$Ph | 2,5-furan | 3-COOH | 2-CH$_3$ | A |
| A99 | 2-Cl | 2,5-furan | 3-COOH | 6-F | A |
| A100 | 4-C(CH$_3$)$_3$ | 2,5-furan | 3-COOH | 6-F | A |
| A101 | 4-cyclohexyl | 2,5-furan | 3-COOH | 6-F | A |
| A102 | 4-C(CH$_3$)$_2$Ph | 2,5-furan | 3-COOH | 6-CH$_3$ | A |
| A103 | 3-CF$_3$ | 2,5-furan | 3-COOH | 6-F | A |
| A104 | 4-Cl | 2,5-furan | 3-COOH | 6-F | A |
| A105 | 3,4-di-Cl | 2,5-furan | 3-COOH | 6-F | A |
| A106 | 2,6-di-Cl | 2,5-furan | 3-COOH | 6-F | A |
| A107 | 3,4-di-Cl | 2,5-furan | 3-COOH | 6-Cl | A |

TABLE 1-continued (Compounds A1 to A294)

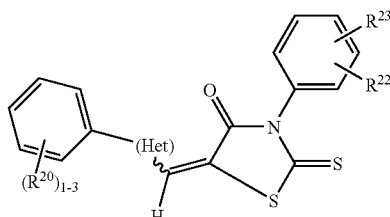

Dlat IC$_{50}$ < 10 μM = A;
Dlat IC$_{50}$ 11-40 μM = B;
Dlat IC$_{50}$ > 41 μM = C

| Compound | R$^{20}$ | Het | R$^{22}$ | R$^{23}$ | Dlat IC$_{50}$ category |
|---|---|---|---|---|---|
| A108 | 3,4-di-Cl | 2,5-furan | 3-COOH | 4-Cl | A |
| A109 | 2,6-di-Cl | 2,5-furan | 3-COOH | 4-Cl | A |
| A110 | 2,6-di-Cl | 2,5-furan | 3-COOH | 6-Cl | A |
| A111 | 3,4-di-Cl | 2,5-furan | 3-COOH | 2-CH$_3$ | A |
| A112 | 2,6-di-Cl | 2,5-furan | 3-COOH | 2-CH$_3$ | A |
| A113 | 3,4-di-Cl | 2,5-furan | 3-COOH | 6-CH$_3$ | A |
| A114 | 2,6-di-Cl | 2,5-furan | 3-COOH | 6-CH$_3$ | A |
| A115 | 3-OH-4-COOH | 2,5-furan | 3-COOH | H | B |
| A116 | 4-N(Me)$_2$ | 2,5-furan | 3-COOH | H | B |
| A117 | 2,3-di-Cl | 2,5-furan | 3-COOH | H | A |
| A118 | 2-Cl | 2,5-furan | 3-(CH$_2$)$_2$COOH | H | A |
| A119 | 3-Cl | 2,5-furan | 3-(CH$_2$)$_2$COOH | H | A |
| A120 | 4-Cl | 2,5-furan | 3-(CH$_2$)$_2$COOH | H | A |
| A121 | 3,5-di-Cl | 2,5-furan | 3-COOH | H | B |
| A122 | 4-CH$_2$N(Me)$_2$ | 2,5-furan | 3-COOH | H | B |
| A123 | 4-Br | 2,5-furan | 3-COOH | H | B |
| A124 | 2-Cl-4-OH | 2,5-furan | 3-COOH | H | A |
| A125 | 3-N(Me)$_2$ | 2,5-furan | 3-COOH | H | A |
| A126 | 4-acetylene | 2,5-furan | 3-COOH | H | B |
| A127 | 3-NO$_2$ | 2,5-furan | 3-COOH | H | A |
| A128 | 3-NO$_2$ | 2,5-furan | 3-COOH | 6-Cl | A |
| A129 | 2-NO$_2$ | 2,5-furan | 3-COOH | H | C |
| A130 | 4-NO$_2$ | 2,5-furan | 3-COOH | H | B |
| A131 | 2-NO$_2$-4-Cl | 2,5-furan | 3-COOH | H | B |
| A132 | 2-Br | 2,5-furan | 3-COOH | H | B |
| A133 | 2-OH-4-C(CH$_3$)$_3$ | 2,5-furan | 3-COOH | H | A |
| A134 | 2-CH$_3$ | 2,5-furan | 3-COOH | H | B |
| A135 | 2-OCH$_3$ | 2,5-furan | 3-COOH | H | A |
| A136 | 4-morpholine | 2,5-furan | 3-COOH | H | B |
| A137 | 4-morpholine | 2,5-furan | 3-COOH | 6-Cl | A |
| A138 | 2-F | 2,5-furan | 3-COOH | H | B |
| A139 | 2-OCH$_3$ | 2,5-furan | 3-COOH | 6-F | A |
| A140 | 2-OCH$_3$ | 2,5-furan | 3-COOH | 6-Cl | A |
| A141 | 2-OCH$_3$ | 2,5-furan | 3-COOH | 6-CH$_3$ | A |
| A142 | 2-OCH$_3$ | 2,5-furan | 3-COOH | 2-CH$_3$ | A |
| A143 | 2-CN-3-F | 2,5-furan | 3-COOH | H | B |
| A144 | 2-CH$_3$ | 2,5-furan | 3-COOH | 6-F | A |
| A145 | 2-CH$_3$ | 2,5-furan | 3-COOH | 6-CH$_3$ | A |
| A146 | 3-Cl-4-OCH$_3$ | 2,5-furan | 3-COOH | H | A |
| A147 | 4-CH$_3$ | 2,5-furan | 3-COOH | H | B |
| A148 | 2-CH$_3$-4-F | 2,5-furan | 3-COOH | H | A |
| A149 | 2-CH$_3$-4-F | 2,5-furan | 3-COOH | 6-F | A |
| A150 | 2-F-4-CH$_3$ | 2,5-furan | 3-COOH | H | B |
| A151 | 2-F-4-CH$_3$ | 2,5-furan | 3-COOH | 6-F | A |
| A152 | 4-OCH$_3$ | 2,5-furan | 3-COOH | H | B |
| A153 | 2,4-di-F | 2,5-furan | 3-COOH | H | A |
| A154 | 2,4-di-F | 2,5-furan | 3-COOH | 6-F | A |
| A155 | 2,4-di-CH$_3$ | 2,5-furan | 3-COOH | H | B |
| A156 | 2,4-di-CH$_3$ | 2,5-furan | 3-COOH | 6-F | A |
| A157 | 2-NHCOOC(CH$_3$)$_3$ | 2,5-furan | 3-COOH | H | C |
| A158 | 2-NH$_2$•HCl | 2,5-furan | 3-COOH | H | C |
| A159 | 2-CH$_3$-4-OCH$_3$ | 2,5-furan | 3-COOH | H | B |
| A160 | 2-CH$_3$-4-OCH$_3$ | 2,5-furan | 3-COOH | 6-F | A |
| A161 | 2-CH$_3$ | 2,6-pyridine | 3-COOH | 6-F | A |
| A162 | 2-OH | 2,5-furan | 3-COOH | H | A |
| A163 | 2-OH | 2,5-furan | 3-COOH | 6-F | A |
| A164 | 2-NHCOOC(CH$_3$)$_3$ | 2,5-furan | 3-COOH | 6-F | B |
| A165 | 4-CH$_3$ | 2,5-furan | 3-COOH | 6-F | A |
| A166 | 4-OCH$_3$ | 2,5-furan | 3-COOH | 6-F | A |
| A167 | 2,4-di-OCH$_3$ | 2,5-furan | 3-COOH | H | A |
| A168 | 2,4-di-OCH$_3$ | 2,5-fbran | 3-COOH | 6-F | A |

TABLE 1-continued (Compounds A1 to A294)

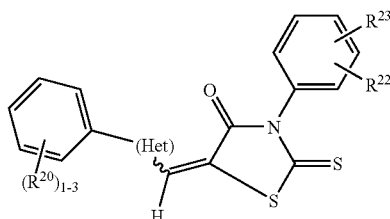

Dlat IC$_{50}$ < 10 μM = A;
Dlat IC$_{50}$ 11-40 μM = B;
Dlat IC$_{50}$ > 41 μM = C

| Compound | R$^{20}$ | Het | R$^{22}$ | R$^{23}$ | Dlat IC$_{50}$ category |
|---|---|---|---|---|---|
| A169 | 2-CH$_3$-4-Cl | 2,5-furan | 3-COOH | H | A |
| A170 | 2-CH$_3$-4-Cl | 2,5-furan | 3-COOH | 6-F | A |
| A171 | 2,6-di-CH$_3$ | 2,5-furan | 3-COOH | H | B |
| A172 | 2,6-di-CH$_3$ | 2,5-furan | 3-COOH | 6-F | A |
| A173 | 2-CH$_3$ | 1,3-phenyl | 3-COOH | H | B |
| A174 | 2-CH$_3$ | 1,3-phenyl | 3-COOH | 6-F | A |
| A175 | 2-OCH$_3$-4-F | 2,5-furan | 3-COOH | H | A |
| A176 | 2-OCH$_3$-4-F | 2,5-furan | 3-COOH | 6-F | A |
| A177 | 3-F-4-OCH$_3$ | 2,5-furan | 3-COOH | H | A |
| A178 | 3-F-4-OCH$_3$ | 2,5-furan | 3-COOH | 6-F | A |
| A179 | 2-OCH$_2$Ph | 2,5-furan | 3-COOH | H | A |
| A180 | 2-OCH$_2$Ph | 2,5-furan | 3-COOH | 6-F | A |
| A181 | 2,4,6-tri-CH$_3$ | 2,5-furan | 3-COOH | 6-F | A |
| A182 | 2-CH$_3$-4-N(CH$_3$)$_2$ | 2,5-furan | 3-COOH | H | A |
| A183 | 2-CH$_3$-4-N(CH$_3$)$_2$ | 2,5-furan | 3-COOH | 6-F | B |
| A184 | 2,4,6-tri-CH$_3$ | 2,5-furan | 3-COOH | H | B |
| A185 | 2-SCH$_3$ | 2,5-furan | 3-COOH | H | A |
| A186 | 2-SCH$_3$ | 2,5-furan | 3-COOH | 6-F | A |
| A187 | 2-CH$_3$ | 2,5-thiophene | 3-COOH | H | B |
| A188 | 2-CH$_3$ | 2,5-thiophene | 3-COOH | 6-F | A |
| A189 | 2-Cl | 2,5-thiophene | 3-COOH | H | A |
| A190 | 2-Cl | 2,5-thiophene | 3-COOH | 6-F | A |
| A191 | 4-N(CH$_3$)$_2$ | 2,5-furan | 3-COOH | 6-F | A |
| A192 | 2-OCH$_2$(2-Cl-Ph) | 1,2-phenyl | 3-COOH | H | B |
| A193 | 2-OPh | 2,5-furan | 3-COOH | H | A |
| A194 | 2-OPh | 2,5-furan | 3-COOH | 6-F | A |
| A195 | 2-F | 2,5-thiophene | 3-COOH | H | B |
| A196 | 2-F | 2,5-thiophene | 3-COOH | H | A |
| A197 | 2-OCH$_2$(2-Cl-Ph) | 1,2-phenyl | 3-COOH | 6-F | A |
| A198 | 2,6-di-CH$_3$ | 2,5-furan | 3-COOH | H | A |
| A199 | 2,6-di-CH$_3$ | 2,5-furan | 3-COOH | 6-F | A |
| A200 | 4-CF$_3$ | 2,5-furan | 3-COOH | H | A |
| A201 | 4-CF$_3$ | 2,5-furan | 3-COOH | 6-F | A |
| A202 | 3-Ph | 2,5-furan | 3-COOH | H | A |
| A203 | 3-Ph | 2,5-furan | 3-COOH | 6-F | A |
| A204 | 4-NHCOCH$_3$ | 2,5-furan | 3-COOH | H | A |
| A205 | 4-NHCOCH$_3$ | 2,5-furan | 3-COOH | 6-F | A |
| A206 | 4-COCH$_3$ | 2,5-furan | 3-COOH | H | A |
| A207 | 4-COCH$_3$ | 2,5-furan | 3-COOH | 6-F | A |
| A208 | 2-F | 2,5-furan | 3-COOH | 6-F | B |
| A209 | 3-CH$_2$OH | 2,5-furan | 3-COOH | H | A |
| A210 | 3-CH$_2$OH | 2,5-furan | 3-COOH | 6-F | A |
| A211 | 4-F | 2,5-furan | 3-COOH | H | A |
| A212 | 4-F | 2,5-furan | 3-COOH | 6-F | A |
| A217 | 4-OCH$_2$CH$_3$ | 2,5-furan | 3-COOH | H | B |
| A218 | 4-OCH$_2$CH$_3$ | 2,5-furan | 3-COOH | 6-F | A |
| A219 | 4-OCH2Ph | 2,5-furan | 3-COOH | H | B |
| A220 | 4-OCH2Ph | 2,5-furan | 3-COOH | 6-F | B |
| A221 | 2-Cl | 2,5-furan | 3-COOH | 5-CF$_3$ | B |
| A222 | 2-F | 2,5-furan | 3-COOH | 5-CF$_3$ | A |
| A223 | 4-Cl | 2,5-furan | 3-COOH | 5-CF$_3$ | B |
| A224 | 4-CH$_3$ | 2,5-furan | 3-COOH | 5-CF$_3$ | A |
| A225 | 4-CH$_2$CH$_3$ | 2,5-furan | 3-COOH | 5-CF$_3$ | B |
| A226 | 4-O(CH$_2$)$_3$CH$_3$ | 2,5-furan | 3-COOH | H | C |
| A227 | 4-O(CH$_2$)$_3$CH$_3$ | 2,5-furan | 3-COOH | 6-F | B |
| A228 | 4-SO$_2$CH$_3$ | 2,5-furan | 3-COOH | H | A |
| A229 | 4-SO$_2$CH$_3$ | 2,5-furan | 3-COOH | 6-F | B |
| A230 | 2-Cl | 2,5-furan | 3-COOH | 5-COOH | A |
| A231 | 2-F | 2,5-furan | 3-COOH | 5-COOH | C |
| A232 | 4-Cl | 2,5-furan | 3-COOH | 5-COOH | B |
| A233 | 4-CH$_3$CH$_3$ | 2,5-furan | 3-COOH | 5-COOH | A |

TABLE 1-continued (Compounds A1 to A294)

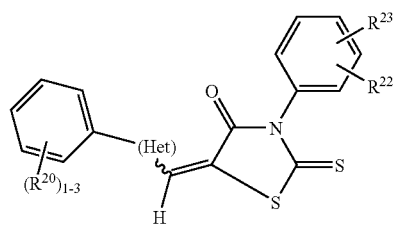

Dlat IC$_{50}$ < 10 μM = A;
Dlat IC$_{50}$ 11-40 μM = B;
Dlat IC$_{50}$ > 41 μM = C

| Compound | R$^{20}$ | Het | R$^{22}$ | R$^{23}$ | Dlat IC$_{50}$ category |
|---|---|---|---|---|---|
| A234 | 2-CH$_3$ | 2,5-furan | 3-COOH | 5-CF$_3$ | A |
| A235 | 2-CH$_3$ | 2,5-furan | 3-COOH | 5-COOH | A |
| A236 | 3-SCH$_3$ | 2,5-furan | 3-COOH | H | A |
| A237 | 3-SCH$_3$ | 2,5-furan | 3-COOH | 6-F | A |
| A238 | 4-SCH$_3$ | 2,5-furan | 3-COOH | H | A |
| A239 | 4-SCH$_3$ | 2,5-furan | 3-COOH | 6-F | A |
| A240 | 4-OCH(CH$_3$)$_2$ | 2,5-furan | 3-COOH | H | A |
| A241 | 4-OCH(CH$_3$)$_2$ | 2,5-furan | 3-COOH | 6-F | A |
| A242 | 4-CH$_3$ | 1,3-phenyl | 3-COOH | H | B |
| A243 | 4-CH$_3$ | 1,3-phenyl | 3-COOH | 6-F | A |
| A244 | 2-Ph | 2,5-furan | 3-COOH | H | A |
| A245 | 2-Ph | 2,5-furan | 3-COOH | 6-F | A |
| A246 | 4-CH$_3$ | 1,4-phenyl | 3-COOH | H | A |
| A247 | 4-CH$_3$ | 1,4-phenyl | 3-COOH | 6-F | B |
| A248 | 4-CH$_3$ | 1,4-phenyl | 3-COOH | 5-CF$_3$ | A |
| A249 | 2-CH$_3$CH$_3$ | 2,5-furan | 3-COOH | H | A |
| A250 | 2-CH$_3$CH$_3$ | 2,5-furan | 3-COOH | 6-F | A |
| A251 | H | 2,4-thiazole | 3-COOH | H | B |
| A252 | H | 2,4-thiazole | 3-COOH | 6-F | B |
| A253 | 2-OCH$_3$-5-CH$_3$ | 2,5-furan | 3-COOH | H | A |
| A254 | 2-OCH$_3$-5-CH$_3$ | 2,5-furan | 3-COOH | 6-F | A |
| A255 | 2-Cl | 2,5-furan | 3-COOH | 4-F | B |
| A256 | 2-F | 2,5-furan | 3-COOH | 4-F | B |
| A257 | 2-CH$_3$ | 2,5-furan | 3-COOH | 4-F | B |
| A258 | 4-Cl | 2,5-furan | 3-COOH | 4-F | A |
| A259 | 4-F | 2,5-furan | 3-COOH | 4-F | B |
| A260 | 4-CH$_3$ | 2,5-furan | 3-COOH | 4-F | A |
| A261 | 4-NHCOCH$_3$ | 2,5-furan | 3-COOH | 5-CF$_3$ | A |
| A262 | 4-NHCOCH$_3$ | 2,5-furan | 3-COOH | 4-F | B |
| A263 | 4-(CH$_2$)$_3$CH$_3$ | 2,5-furan | 3-COOH | H | A |
| A264 | 4-(CH$_2$)$_3$CH$_3$ | 2,5-furan | 3-COOH | 6-F | A |
| A265 | 4-(CH$_2$)$_3$CH$_3$ | 2,5-furan | 3-COOH | 4-F | A |
| A266 | 4-(CH$_2$)$_3$CH$_3$ | 2,5-furan | 3-COOH | 5-CF$_3$ | A |
| A267 | 4-SO$_2$CH$_3$ | 2,5-furan | 3-COOH | 5-CF$_3$ | A |
| A268 | 4-SO$_2$CH$_3$ | 2,5-furan | 3-COOH | 4-F | A |
| A269 | 4-(CH$_2$)$_2$CH$_3$ | 2,5-furan | 3-COOH | H | A |
| A270 | 4-(CH$_2$)$_2$CH$_3$ | 2,5-furan | 3-COOH | 6-F | A |
| A271 | 4-(CH$_2$)$_2$CH$_3$ | 2,5-furan | 3-COOH | 4-F | A |
| A272 | 4-(CH$_2$)$_2$CH$_3$ | 2,5-furan | 3-COOH | 5-CF$_3$ | B |
| A274 | 2-Cl | 2,5-furan | 3-COOH | 4-N(CH$_3$)$_2$ | B |
| A275 | 3-Cl | 2,5-furan | 3-COOH | 4-N(CH$_3$)$_2$ | B |
| A279 | 2-OCH$_2$Ph | 2,5-furan | 3-COOH | 4-F | A |
| A280 | 2-CF$_3$ | 2,5-furan | 3-COOH | 4-F | B |
| A281 | 2-OCF$_3$ | 2,5-furan | 3-COOH | 4-F | A |
| A282 | 2-SCH$_3$ | 2,5-furan | 3-COOH | 4-F | A |
| A283 | 2-OPh | 2,5-furan | 3-COOH | 4-F | A |
| A284 | 2-Ph | 2,5-furan | 3-COOH | 4-F | A |
| A286 | 4-SO$_2$NHCH$_3$ | 2,5-furan | 3-COOH | H | B |
| A287 | 4-SO$_2$NHCH$_3$ | 2,5-furan | 3-COOH | 4-F | B |
| A288 | 4-SO$_2$NH$_2$ | 2,5-furan | 3-COOH | H | B |
| A289 | 3-OH-4-COOH | 2,5-furan | H | H | A |
| A290 | 4-COOH | 2,5-furan | 3-OH | H | A |
| A291 | 4-COOH | 2,5-furan | 4-OH | H | A |
| A293 | 4-COOH | 2,5-furan | 3-CONH$_2$ | H | B |
| A294 | 4-COOH | 2,5-furan | 4-SO$_2$NH$_2$ | H | A |

TABLE 2

(Compounds B1 to B115)

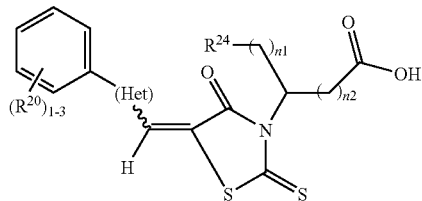

| Compound | R20 | Het | n1 | n2 | R24 | Dlat IC50 category |
|---|---|---|---|---|---|---|
| B1 | 2-Cl | 2,5-furan | 0 | 0 | Ph | A |
| B2 | 3-Cl | 2,5-furan | 0 | 0 | Ph | A |
| B3 | 3-CF3 | 2,5-furan | 0 | 1 | H | A |
| B4 | 2-CF3 | 2,5-furan | 0 | 1 | H | B |
| B5 | 2-Cl | 2,5-furan | 0 | 1 | H | B |
| B6 | 2-Cl | 2,5-furan | 0 | 0 | H | B |
| B7 | 2-Cl | 2,6-pyridine | 0 | 1 | H | C |
| B8 | 2-Cl | 2,6-pyridine | 0 | 0 | Ph | B |
| B9 | 4-Cl | 2,5-furan | 0 | 0 | Ph | A |
| B10 | 3,4-di-Cl | 2,5-furan | 0 | 0 | Ph | A |
| B11 | 2-Cl | 2,5-furan | 0 | 4 | H | A |
| B12 | 3-Cl | 2,5-furan | 0 | 4 | H | A |
| B13 | 4-Cl | 2,5-furan | 0 | 4 | H | A |
| B14 | 3,4-di-Cl | 2,5-furan | 0 | 4 | H | A |
| B15 | 2-Cl | 2,6-pyridine | 0 | 4 | H | B |
| B16 | 4-Ph | 2,5-furan | 0 | 0 | H | A |
| B17 | 4-Ph | 2,5-furan | 0 | 1 | H | B |
| B18 | 4-Ph | 2,5-furan | 0 | 4 | H | A |
| B19 | 4-Ph | 2,5-furan | 0 | 0 | Ph | A |
| B20 | 2-Cl-5-CF3 | 2,5-furan | 0 | 4 | H | A |
| B21 | 3-Cl-4-OCH3 | 2,5-furan | 0 | 4 | H | B |
| B22 | 3-CF3 | 2,5-furan | 0 | 4 | H | A |
| B23 | 2-CF3 | 2,5-furan | 0 | 4 | H | B |
| B24 | 2-OCF3 | 2,5-furan | 0 | 4 | H | A |
| B25 | 3-CF3 | 2,5-thiazole | 0 | 0 | Ph | A |
| B26 | 4-OH | 2,5-furan | 0 | 1 | H | C |
| B27 | 4-OH | 2,5-furan | 0 | 4 | H | A |
| B28 | 4-OPh | 2,5-furan | 0 | 0 | Ph | B |
| B29 | 4-OH | 2,5-furan | 0 | 0 | Ph | B |
| B30 | 4-CH2Ph | 2,5-furan | 0 | 0 | H | A |
| B31 | 4-CH2Ph | 2,5-furan | 0 | 1 | H | A |
| B32 | 4-CH2Ph | 2,5-furan | 0 | 0 | Ph | A |
| B33 | 4-CH2Ph | 2,5-furan | 0 | 4 | H | B |
| B34 | 3-Cl | 2,5-oxazole | 0 | 4 | H | B |
| B35 | 3-Cl | 2,5-oxazole | 0 | 0 | Ph | B |
| B36 | 4-Cl | 2,5-furan | 0 | 0 | (R)-Ph | A |
| B37 | 4-Cl | 2,5-furan | 0 | 0 | (S)-Ph | A |
| B38 | 3-CF3 | 2,4-furan | 0 | 0 | Ph | A |
| B39 | 3-CF3 | 2,4-furan | 0 | 4 | H | B |
| B40 | 3-CF3 | 2,5-furan | 1 | 0 | Ph | A |
| B41 | 2-Cl | 2,5-furan | 1 | 0 | Ph | A |
| B42 | 4-Cl | 2,5-furan | 1 | 0 | Ph | A |
| B43 | 2,4-di-Cl | 2,5-furan | 0 | 0 | H | A |
| B44 | 2,4-di-Cl | 2,5-furan | 0 | 0 | Ph | A |
| B45 | 2,4-di-Cl | 2,5-furan | 1 | 0 | Ph | A |
| B46 | 2,5-di-Cl | 2,5-furan | 0 | 0 | Ph | A |
| B47 | 2,5-di-Cl | 2,5-furan | 1 | 0 | Ph | A |
| B48 | 2,6-di-Cl | 2,5-furan | 0 | 0 | Ph | A |
| B49 | 2,6-di-Cl | 2,5-furan | 1 | 0 | Ph | A |
| B50 | 3-CF3 | 2,5-furan | 0 | 0 | Ph | A |
| B51 | 2-Cl | 2,5-furan | 1 | 0 | Ph-(4-OH) | A |
| B52 | 3-CF3 | 2,5-furan | 1 | 0 | Ph-(4-OH) | A |
| B53 | 4-Cl | 2,5-furan | 1 | 0 | Ph-(4-OH) | A |
| B54 | 2-Cl | 2,5-furan | 1 | 0 | Ph-(3,4-di-OH) | B |
| B55 | 3-CF3 | 2,5-furan | 1 | 0 | Ph-(3,4-di-OH) | A |
| B56 | 4-Cl | 2,5-furan | 1 | 0 | Ph-(3,4-di-OH) | B |
| B57 | 4-CH2Ph | 2,5-furan | 1 | 0 | Ph | A |
| B58 | 4-CH2Ph | 2,5-furan | 1 | 0 | Ph-(4-OH) | A |
| B59 | 4-CH2Ph | 2,5-furan | 1 | 0 | Ph-(3,4-di-OH) | A |
| B60 | 4-Cl | 2,5-furan | 0 | 0 | H | B |
| B61 | 2-Cl-5-CF3 | 2,5-furan | 0 | 0 | H | A |
| B62 | 2,5-di-Cl | 2,5-furan | 1 | 0 | Ph-(4-OH) | A |

TABLE 2-continued (Compounds B1 to B115)

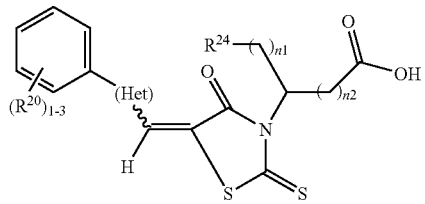

| Compound | R20 | Het | n1 | n2 | R24 | Dlat IC50 category |
|---|---|---|---|---|---|---|
| B63 | 2-Cl-5-CF3 | 2,5-furan | 1 | 0 | Ph-(4-OH) | A |
| B64 | 2,5-di-Cl | 2,5-furan | 1 | 0 | Ph-(3,4-di-OH) | A |
| B65 | 2-Cl-5-CF3 | 2,5-furan | 1 | 0 | Ph-(3,4-di-OH) | A |
| B66 | 4-CH(CH3)2 | 2,5-furan | 0 | 0 | Ph | A |
| B67 | 4-CH(CH3)2 | 2,5-furan | 1 | 0 | Ph | A |
| B68 | 4-CH(CH3)2 | 2,5-furan | 1 | 0 | Ph-(3,4-di-OH) | A |
| B69 | 4-COPh | 2,5-furan | 0 | 0 | H | B |
| B70 | 4-CH(CH3)2 | 2,5-furan | 0 | 0 | H | B |
| B71 | 4-CH2SPh | 2,5-furan | 0 | 0 | H | B |
| B72 | 3-CH(CH3)2 | 2,5-furan | 0 | 0 | H | A |
| B73 | 4-cyclohexyl | 2,5-furan | 0 | 0 | H | A |
| B74 | 4-C(CH3)3 | 2,5-furan | 0 | 0 | H | A |
| B75 | 3-CH(CH3)2 | 2,5-furan | 1 | 0 | Ph | A |
| B76 | 4-CH2SPh | 2,5-furan | 1 | 0 | Ph | A |
| B77 | 4-CH2CH(CH3)2 | 2,5-furan | 0 | 0 | H | A |
| B78 | 4-CH2CH(CH3)2 | 2,5-furan | 0 | 0 | Ph | A |
| B79 | 4-CH3(4-Cl—Ph) | 2,5-furan | 0 | 0 | H | A |
| B80 | 4-C—(OH)—Ph | 2,5-furan | 0 | 0 | H | B |
| B81 | 4-cyclopentyl | 2,5-furan | 0 | 0 | H | A |
| B82 | 4-C(=CH2)—Ph | 2,5-furan | 0 | 0 | H | A |
| B83 | 4-dimethylbenzyl | 2,5-furan | 0 | 0 | H | A |
| B84 | 4-N(CH3)2 | 2,5-furan | 0 | 0 | H | B |
| B85 | 2,3-di-Cl | 2,5-furan | 0 | 0 | H | A |
| B86 | 4-N(CH3)2 | 2,5-furan | 0 | 0 | H | C |
| B87 | 2-CH3 | 2,5-furan | 0 | 0 | H | C |
| B88 | 2-OCH3 | 2,5-furan | 0 | 0 | H | B |
| B89 | 2-CN-3-F | 2,5-furan | 0 | 0 | Ph | B |
| B90 | 2-Cl | 2,5-furan | 0 | 2 | H | A |
| B91 | 3-CF3 | 2,5-furan | 0 | 2 | H | A |
| B92 | 2-CH3-4-N(CH3)2 | 2,5-furan | 0 | 2 | H | B |
| B93 | 4-SO2CH3 | 2,5-furan | 0 | 2 | H | B |
| B94 | 2-Cl | 2,5-furan | 0 | 0 | CH3 | B |
| B95 | 3-Cl | 2,5-furan | 0 | 0 | CH3 | B |
| B96 | 4-Cl | 2,5-furan | 0 | 0 | CH3 | A |
| B97 | 2-CH3 | 2,5-furan | 0 | 0 | CH3 | B |
| B98 | 4-F | 2,5-furan | 0 | 0 | CH3 | C |
| B99 | 2-CF3 | 2,5-furan | 0 | 0 | CH3 | B |
| B100 | 3-CF3 | 2,5-furan | 0 | 0 | CH3 | A |
| B101 | 2-Cl | 2,5-furan | 0 | 0 | CH(CH3)2 | A |
| B102 | 3-Cl | 2,5-furan | 0 | 0 | CH(CH3)2 | B |
| B103 | 4-Cl | 2,5-furan | 0 | 0 | CH(CH3)2 | A |
| B104 | 2-CF3 | 2,5-furan | 0 | 0 | CH(CH3)2 | A |
| B105 | 3-CF3 | 2,5-furan | 0 | 0 | CH(CH3)2 | B |
| B106 | 2-CH3 | 2,5-furan | 0 | 0 | CH(CH3)2 | B |
| B107 | 4-F | 2,5-furan | 0 | 0 | CH(CH3)2 | B |
| B108 | 2,4-di-Cl | 2,5-furan | 0 | 0 | CH(CH3)2 | A |
| B109 | 3-Cl-4-OCH3 | 2,5-furan | 0 | 0 | CH(CH3)2 | A |
| B110 | 2-NO2-4-Cl | 2,5-furan | 0 | 0 | CH(CH3)2 | B |
| B111 | 3,4-di-Cl | 2,5-furan | 0 | 0 | CH(CH3)2 | A |
| B112 | 2,4-di-Cl | 2,5-furan | 0 | 0 | CH3 | A |
| B113 | 3-Cl-4-OCH3 | 2,5-furan | 0 | 0 | CH3 | A |
| B114 | 2-NO2-4-Cl | 2,5-furan | 0 | 0 | CH3 | B |
| B115 | 4-SO2NHCH3 | 2,5-furan | 0 | 2 | H | C |

TABLE 3

(Compounds C1 to C86)

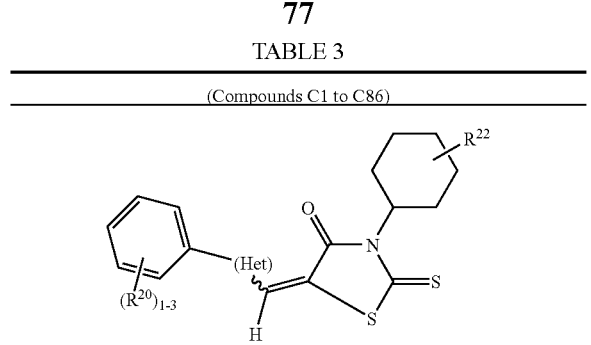

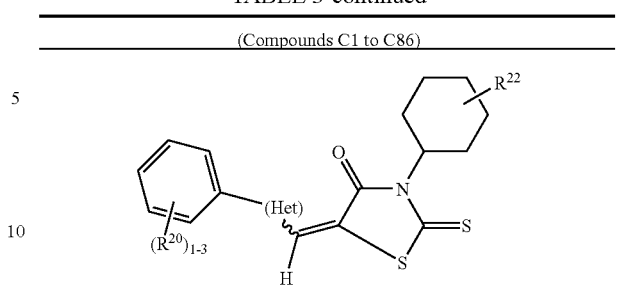

| Compound | $R^{24}$ | Het | $R^{22}$ | Dlat $IC_{50}$ category |
|---|---|---|---|---|
| C1 | 2-Cl | 2,5-furan | 3-COOH | B |
| C2 | 4-cyclohexyl | 2,5-furan | 3-COOH | A |
| C3 | 4-tert-butyl | 2,5-furan | 3-COOH | A |
| C4 | 4-isobutyl | 2,5-furan | 3-COOH | A |
| C5 | 3-$CF_3$ | 2,5-furan | 3-COOH | A |
| C6 | 4-$CH_2Ph$ | 2,5-furan | 3-COOH | A |
| C7 | 2,4-di-F | 2,5-furan | 3-COOH | A |
| C8 | 2,4-di-Me | 2,5-furan | 3-COOH | A |
| C9 | 2-Me-4-OMe | 2,5-furan | 3-COOH | B |
| C10 | 2-Me | 2,6-pyridine | 3-COOH | C |
| C11 | 2-Me-4-F | 2,5-furan | 3-COOH | A |
| C12 | 2-F-4-Me | 2,5-furan | 3-COOH | A |
| C13 | 2-OH | 2,5-furan | 3-COOH | A |
| C14 | 4-Me | 2,5-furan | 3-COOH | A |
| C15 | 4-OMe | 2,5-furan | 3-COOH | A |
| C16 | 2-Cl | 2,5-furan | 4-COOH | A |
| C17 | 3-$CF_3$ | 2,5-furan | 4-COOH | A |
| C18 | 4-Cl | 2,5-furan | 4-COOH | A |
| C19 | 2,4-di-OMe | 2,5-furan | 3-COOH | A |
| C20 | 2-Me-4-Cl | 2,5-furan | 3-COOH | A |
| C21 | 2-Cl | 2,5-furan | 4-OH | B |
| C22 | 4-Cl | 2,5-furan | 4-OH | B |
| C23 | 2,6-di-Me | 2,5-furan | 3-COOH | B |
| C24 | 2-Me | phenyl | 3-COOH | B |
| C25 | 2-OMe-4-F | 2,5-furan | 3-COOH | A |
| C26 | 3-F-4-OMe | 2,5-furan | 3-COOH | A |
| C27 | 2-$OCH_2Ph$ | 2,5-furan | 3-COOH | A |
| C28 | 2,4,6-tri-Me | 2,5-furan | 3-COOH | A |
| C29 | 2-Me-4-$N(Me)_2$ | 2,5-furan | 3-COOH | B |
| C30 | 2-SMe | 2,5-furan | 3-COOH | A |
| C31 | 2-Me | 2,5-thiophene | 3-COOH | B |
| C32 | 2-Cl | 2,5-thiophene | 3-COOH | A |
| C33 | 2-$OCH_2$(2-Cl—Ph) | phenyl | 3-COOH | B |
| C34 | 2-OPh | 2,5-furan | 3-COOH | A |
| C35 | 2-F | 2,5-thiophene | 3-COOH | B |
| C36 | 4-$CH_2CH_3$ | 2,5-furan | 3-COOH | A |
| C37 | 4-$CF_3$ | 2,5-furan | 3-COOH | A |
| C38 | 3-Ph | 2,5-furan | 3-COOH | A |
| C39 | 4-$NHCOCH_3$ | 2,5-furan | 3-COOH | A |
| C40 | 4-$COCH_3$ | 2,5-furan | 3-COOH | A |
| C41 | 2-F | 2,5-furan | 3-COOH | A |
| C42 | 3-$CH_2OH$ | 2,5-furan | 3-COOH | A |
| C43 | 4-F | 2,5-furan | 3-COOH | A |
| C44 | 2-F | 2,5-furan | 4-COOH | A |
| C45 | 4-Me | 2,5-furan | 4-COOH | A |
| C46 | 2-F-4-Me | 2,5-furan | 4-COOH | A |
| C47 | 2-F | 2,5-thiophene | 4-COOH | B |
| C51 | 4-$OCH_2CH_3$ | 2,5-furan | 3-COOH | A |
| C52 | 4-$OCH_2CH_3$ | 2,5-furan | 4-COOH | A |
| C53 | 3-F-4-OMe | 2,5-furan | 4-COOH | A |
| C54 | 2-SMe | 2,5-furan | 4-COOH | A |
| C55 | 4-$CF_3$ | 2,5-furan | 4-COOH | B |
| C56 | 4-Cl | 2,5-furan | 3-COOH | A |
| C57 | 4-$O(CH_2)_3CH_3$ | 2,5-furan | 4-COOH | B |
| C58 | 4-$SO_2Me$ | 2,5-furan | 3-COOH | A |
| C59 | 4-$SO_2Me$ | 2,5-furan | 4-COOH | A |
| C60 | 2-Me | 2,5-furan | 3-COOH | A |
| C61 | 2-Me | 2,5-furan | 4-COOH | B |
| C62 | 3-SMe | 2,5-furan | 3-COOH | A |
| C63 | 3-SMe | 2,5-furan | 4-COOH | A |
| C64 | 4-SMe | 2,5-furan | 3-COOH | A |
| C65 | 4-SMe | 2,5-furan | 4-COOH | A |
| C66 | 4-$OCH(CH_3)_2$ | 2,5-furan | 3-COOH | A |
| C67 | 4-$OCH(CH_3)_2$ | 2,5-furan | 4-COOH | A |
| C68 | 3-(4-Me—Ph) | phenyl | 3-COOH | C |
| C69 | 3-(4-Me—Ph) | phenyl | 4-COOH | A |
| C70 | 2-Ph | 2,5-furan | 3-COOH | A |
| C71 | 2-Ph | 2,5-furan | 4-COOH | A |
| C72 | 4-(4-Me—Ph) | phenyl | 3-COOH | A |
| C73 | 4-(4-Me—Ph) | phenyl | 4-COOH | A |
| C74 | 2-OMe-5-Me | 2,5-furan | 3-COOH | B |
| C75 | 2-OMe-5-Me | 2,5-furan | 4-COOH | B |
| C76 | 4-$NHCOCH_3$ | 2,5-furan | 4-COOH | A |
| C77 | 4-$(CH_2)_3CH_3$ | 2,5-furan | 3-COOH | A |
| C78 | 4-$(CH_2)_3CH_3$ | 2,5-furan | 4-COOH | A |
| C79 | 4-$(CH_2)_3CH_3$ | 2,5-furan | 3-COOH | B |
| C80 | 4-$(CH_2)_2CH_3$ | 2,5-furan | 4-COOH | B |
| C83 | 4-$SO_2NHMe$ | 2,5-furan | 3-COOH | B |
| C84 | 4-$SO_2NHMe$ | 2,5-furan | 4-COOH | A |
| C85 | 4-$SO_2N(Me)_2$ | 2,5-furan | 3-COOH | C |
| C86 | 4-$SO_2N(Me)_2$ | 2,5-furan | 4-COOH | B |

TABLE 4

(Compounds D1 to D60)

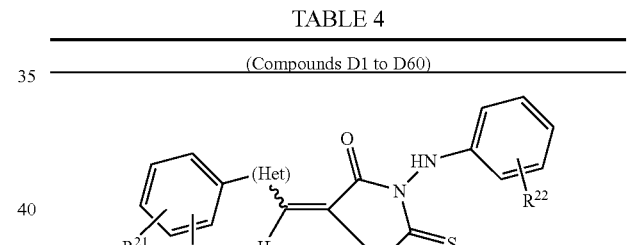

| Compound | $R^{20}$ | $R^{21}$ | Het | $R^{22}$ | Dlat $IC_{50}$ category |
|---|---|---|---|---|---|
| D1 | 2-Cl | H | 2,5-furan | 2-COOH | A |
| D2 | 4-tert-butyl | H | 2,5-furan | 2-COOH | A |
| D3 | 3-$CF_3$ | H | 2,5-furan | 2-COOH | A |
| D4 | 3-$NO_2$ | H | 2,5-furan | 2-COOH | A |
| D5 | 5-tert-butyl | 2-OH | 2,5-furan | 2-COOH | A |
| D6 | 4-morpholine | H | 2,5-furan | 2-COOH | B |
| D7 | 2,4-di-F | H | 2,5-furan | 2-COOH | A |
| D8 | 2,4-di-Me | H | 2,5-furan | 2-COOH | A |
| D9 | 2-Me | 4-OMe | 2,5-furan | 2-COOH | A |
| D10 | 2-Me | 4-F | 2,5-furan | 2-COOH | A |
| D11 | 2-F | 4-Me | 2,5-furan | 2-COOH | A |
| D12 | 2-OH | H | 2,5-furan | 2-COOH | A |
| D13 | 4-Me | H | 2,5-furan | 2-COOH | A |
| D14 | 4-OMe | H | 2,5-furan | 2-COOH | A |
| D15 | 2-Me | H | 2,6-pyridine | 2-COOH | B |
| D16 | 2-Cl | H | 2,5-furan | 3-COOH | A |
| D17 | 3-$CF_3$ | H | 2,5-furan | 3-COOH | A |
| D18 | 4-Cl | H | 2,5-furan | 3-COOH | A |
| D19 | 2,4-di-OMe | H | 2,5-furan | 2-COOH | A |
| D20 | 2-Cl | H | 2,5-furan | 4-COOH | B |
| D21 | 4-Cl | H | 2,5-furan | 4-COOH | A |
| D22 | 5-indolyl | H | 2,5-furan | 2-COOH | A |
| D23 | 2-Me | 4-Cl | 2,5-furan | 2-COOH | A |
| D24 | 2,6-di-Me | H | 2,5-furan | 2-COOH | A |
| D25 | 2-OMe | 4-F | 2,5-furan | 2-COOH | A |

TABLE 4-continued (Compounds D1 to D60)

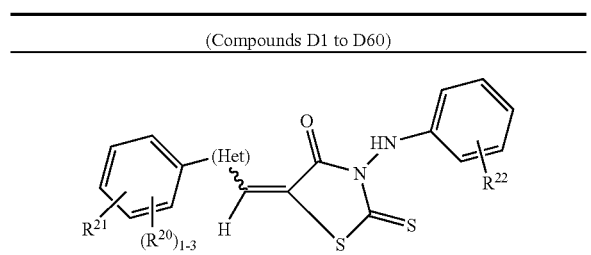

| Compound | $R^{20}$ | $R^{21}$ | Het | $R^{22}$ | Dlat $IC_{50}$ category |
|---|---|---|---|---|---|
| D26 | 3-F | 4-OMe | 2,5-furan | 2-COOH | A |
| D27 | 2-OCH$_2$Ph | H | 2,5-furan | 2-COOH | B |
| D28 | 2,4,6-tri-Me | H | 2,5-furan | 2-COOH | A |
| D29 | 2-Me | 4-N(Me)$_2$ | 2,5-furan | 2-COOH | B |
| D30 | 2-Sme | H | 2,5-furan | 2-COOH | A |
| D31 | 4-N(Me)$_2$ | H | 2,5-furan | 2-COOH | B |
| D32 | 2-OCH$_2$(2-Cl—Ph) | H | phenyl | 2-COOH | A |
| D33 | 2-OPh | H | 2,5-furan | 2-COOH | A |
| D34 | 2-Me | H | 2,5-thiophene | 2-COOH | A |
| D35 | 2-Cl | H | 2,5-thiophene | 2-COOH | A |
| D36 | 2-F | H | 2,5-thiophene | 2-COOH | A |
| D37 | 3-CF$_3$ | H | 2,5-furan | 4-COOH | A |
| D38 | 4-CH$_2$CH$_3$ | H | 2,5-furan | 2-COOH | A |
| D39 | 4-CF$_3$ | H | 2,5-furan | 2-COOH | A |
| D40 | 3-Ph | H | 2,5-furan | 2-COOH | A |
| D41 | 4-NHCOCH$_3$ | H | 2,5-furan | 2-COOH | A |
| D42 | 4-COCH$_3$ | H | 2,5-furan | 2-COOH | A |
| D43 | 2-F | H | 2,5-furan | 2-COOH | A |
| D44 | 3-CH$_2$OH | H | 2,5-furan | 2-COOH | A |
| D45 | 4-F | H | 2,5-furan | 2-COOH | A |
| D48 | 4-OCH$_2$Ph | H | 2,5-furan | 2-COOH | B |
| D49 | 4-O(CH$_2$)$_3$CH$_3$ | H | 2,5-furan | 2-COOH | A |
| D50 | 4-SO$_2$Me | H | 2,5-furan | 2-COOH | A |
| D51 | 2-Me | H | 2,5-furan | 2-COOH | A |
| D52 | 3-SMe | H | 2,5-furan | 2-COOH | A |
| D53 | 4-SMe | H | 2,5-furan | 2-COOH | B |
| D54 | 4-OCH(CH$_3$)$_2$ | H | 2,5-furan | 2-COOH | A |
| D55 | 3-(4-Me—Ph) | H | phenyl | 2-COOH | A |
| D56 | 4-(4-Me—Ph) | H | phenyl | 2-COOH | B |
| D57 | 2-Ph | H | 2,5-furan | 2-COOH | A |
| D58 | 2-CH$_2$CH$_3$ | H | 2,5-furan | 2-COOH | A |
| D59 | 4-(CH$_2$)$_3$CH$_3$ | H | 2,5-furan | 2-COOH | A |
| D60 | 4-(CH$_2$)$_2$CH$_3$ | H | 2,5-furan | 2-COOH | A |

TABLE 5

(Compounds E1 to E3)

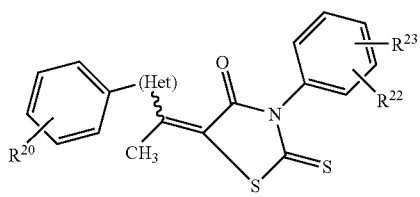

| Compound | $R^{20}$ | $R^{22}$ | $R^{23}$ | Dlat $IC_{50}$ category |
|---|---|---|---|---|
| E1 | 3-CF$_3$ | 3-COOH | 4-OH | A |
| E2 | 3-CF$_3$ | 3-COOH | H | A |
| E3 | 2-Cl | 3-COOH | H | B |

TABLE 6

(Compounds F1 to F3)

| Compound | $R^{20}$ | $R^{24}$ | n1 | n2 | Dlat $IC_{50}$ category |
|---|---|---|---|---|---|
| F1 | 3-CF$_3$ | Ph | 1 | 0 | A |
| F2 | 3-CF$_3$ | Ph | 0 | 0 | A |
| F3 | 3-CF$_3$ | H | 0 | 1 | B |

TABLE 7

(Compounds G1 to G4)

| Compound | $R^{20}$ | $R^{21}$ | Dlat $IC_{50}$ category |
|---|---|---|---|
| G1 | 2-Cl | H | A |
| G2 | 3-CF$_3$ | H | A |
| G3 | 2-Cl | 5-CF3 | A |
| G4 | 2-Cl | 5-Cl | A |

TABLE 8

(Compound H1)

| Compound | Dlat $IC_{50}$ category |
|---|---|
| H1 | B |

TABLE 9

(Compounds I1 to I2)

| Compound | $R^{23}$ | Dlat $IC_{50}$ category |
|---|---|---|
| I1 | H | A |
| I2 | 4-OH | A |

TABLE 10

(Compounds J1 to J3)

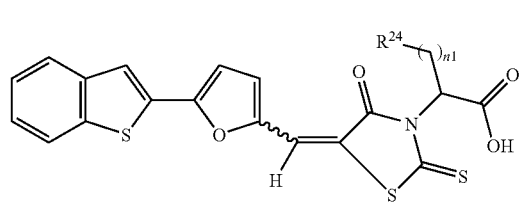

| Compound | R²⁴ | n1 | Dlat IC₅₀ category |
|---|---|---|---|
| J1 | H | 0 | A |
| J2 | Ph | 0 | A |
| J3 | Ph | 1 | A |

TABLE 13

(Compounds M1 to M4)

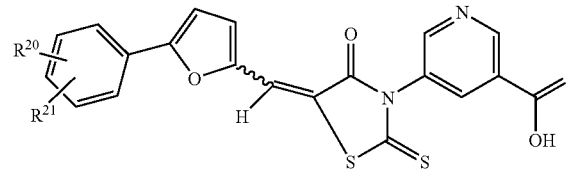

| Compound | R²⁰ | R²¹ | Dlat IC₅₀ category |
|---|---|---|---|
| M1 | 2-Cl | H | A |
| M2 | 3-CF₃ | H | A |
| M3 | 4-C(CH₃)₃ | H | A |
| M4 | 2-CN | 3-F | B |

TABLE 14

(Compounds N1 to N3)

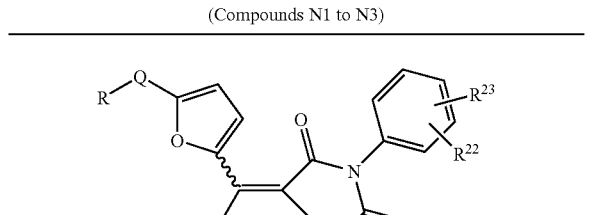

| Compound | R | Q | R22 | R23 | Dlat IC₅₀ category |
|---|---|---|---|---|---|
| N1 | 2-Cl—Ph | CH2 | 3-COOH | H | A |
| N2 | 2-Cl—Ph | CH2 | 3-COOH | 6-OCH3 | B |
| N3 | 2-Cl—Ph | CH2 | 3-COOH | 4-OH | A |

TABLE 15

(Compounds O1 to O5)

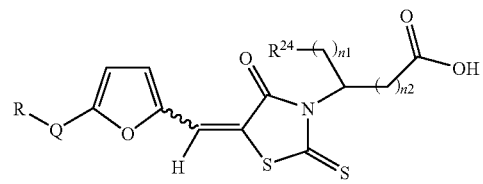

| Compound | R | Q | R²⁴ | n1 | N2 | Dlat IC₅₀ category |
|---|---|---|---|---|---|---|
| O1 | 4-Cl—Ph | O | H | 0 | 1 | B |
| O2 | 4-Cl—Ph | O | H | 0 | 4 | C |
| O3 | 4-Cl—Ph | O | Ph | 0 | 0 | A |
| O4 | 2-Cl—Ph | CH2 | H | 0 | 0 | B |
| O5 | 2-Cl—Ph | CH2 | Ph | 0 | 0 | B |

TABLE 16

(Compounds P1 to P2)

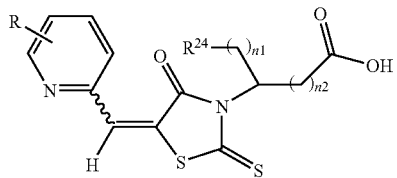

| Compound | R | R²⁴ | n1 | n2 | Dlat IC₅₀ category |
|---|---|---|---|---|---|
| P1 | 6-(5-Cl-thiophen-2-yl) | Ph | 0 | 0 | A |
| P2 | 6-(5-Cl-thiophen-2-yl) | H | 0 | 1 | B |

TABLE 17

(Compounds Q1 to Q9)

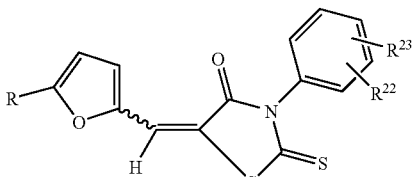

| Compound | R | R²² | R²³ | Dlat IC₅₀ category |
|---|---|---|---|---|
| Q1 | pyrimidin-5-yl | 3-COOH | H | B |
| Q2 | pyrimidin-5-yl | 4-COOH | H | B |
| Q3 | pyrimidin-5-yl | 4-SO₂NH₂ | H | B |
| Q4 | pyridin-4-yl | 3-COOH | H | B |
| Q5 | 2-Cl-thiophen-3-yl | 3-COOH | 4-OH | B |
| Q6 | 4-(piperidine-1-carbonyl)-quinolin-2-yl | 3-COOH | H | B |
| Q7 | 6-Br-4-(piperidine-1-carbonyl)-quinolin-2-yl | 3-COOH | H | B |
| Q9 | benzo[1,2,5]oxadiazol-5-yl- | 3-COOH | H | B |

TABLE 18

(Compounds R2 to R6)

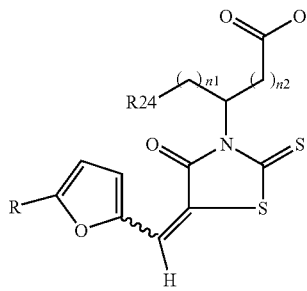

| Compound | R | R24 | n1 | n2 | DlaT IC50 category |
|---|---|---|---|---|---|
| R2 | pyrimidin-5-yl | H | 0 | 4 | B |
| R3 | piperidin-yl | Ph | 0 | 0 | C |
| R4 | pyridin-4-yl | Ph | 0 | 0 | C |
| R5 | 6-Br-4-(piperidine-1-carbonyl)-quinolin-2-yl- | H | 0 | 0 | B |
| R6 | benzo[1,2,5]oxadiazol-5-yl- | H | 0 | 0 | C |

TABLE 20

Prodrugs (Compounds T1 to T8)

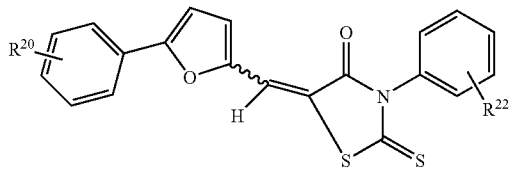

| Compound | R20 | R22 | DlaT IC50 category |
|---|---|---|---|
| T1 | 2-Cl | 3-COO(CH2)4OH | C |
| T2 | 2-Cl | 3-COO(CH2)3OH | C |
| T3 | 2-Cl | 3-COO(CH2)4OPO3H | C |
| T4 | 2-Cl | 3-COOCH2CH(CH2OH)2 | B |
| T5 | 2-Cl | 3-COOCH2C(CH3)(CH2OH)2 | B |
| T6 | 2-Cl | 3-CONHC(CH2OH)3 | B |
| T7 | 2-Cl | 3-CONHCH(CH2OH)2 | B |
| T8 | 2-Cl | 3-COOCH2CH2N(CH2CH2OH)2 | C |

TABLE 21

Prodrugs (Examples U1 to U10)

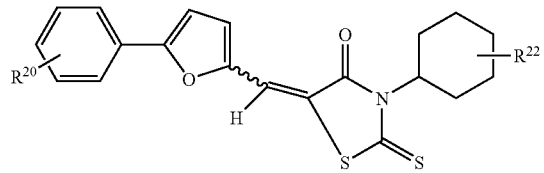

| Compound | R20 | R22 | DlaT IC50 category |
|---|---|---|---|
| U1 | 4-SMe | 3-COO(CH2)3OH | C |
| U2 | 4-SO2NHMe | 3-COO(CH2)3OH | B |
| U3 | 4-SMe | 3-COO(CH2)2OH | C |
| U4 | 4-SMe | 3-COO(CH2)4OH | C |
| U5 | 4-SMe | 3-COOCH2CH(CH2OH)2 | B |
| U6 | 4-SMe | 3-COOCH2C(CH2OH)2CH3 | C |
| U7 | 4-SMe | 3-CONHC(CH2OH)3 | C |
| U8 | 4-SMe | 3-CONHCH(CH2OH)2 | C |

TABLE 21-continued

Prodrugs (Examples U1 to U10)

| Compound | R20 | R22 | DlaT IC50 category |
|---|---|---|---|
| U9 | 4-SO2Me | 3-COO(CH2)3OH | C |
| U10 | 4-SMe | 3-COO(CH2)2N(CH2CH2OH)2•HCl | A |

In Vitro Studies with Mycopyrin 5

Peroxidase activity of mycopyrin 5 was measured by 5,5'-dithiobis-(2-nitrobenzoic acid (DTNB) assay with 100 µM NADH, 75 µM DTNB in 50 mM potassium phosphate buffer, pH 7.0, 1 mM EDTA in 100 µl reactions containing 100 nM Lpd, 175 nM DlaT and 18 nM AhpD. TNB (thionitrobenzoate) formation was measured over time at 405 nM. PDH activity was measured by PDH assay with 1 mM NAD+, 200 µM TPP (thiamine pyrophosphate), 1 mM MgCl2, 170 µM CoA, 1 mM pyruvate in 50 mM potassium phosphate, pH 7.0 in 200 µl reactions containing 100 nM Lpd, 175 nM DlaT and 100 nM AceE. Pyruvate and CoA dependent NADH formation was measured over time at 340 nM.

Figure 2:
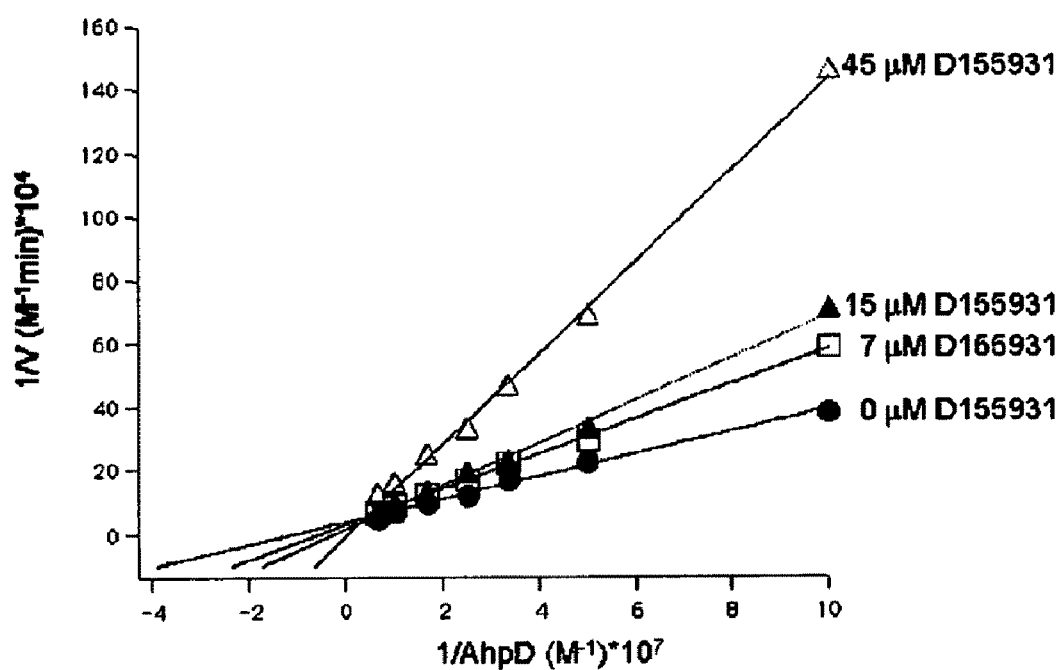
FIG. 2 is a graph of $1/V(M^{-1}\, min) \times 10^4$ versus $1/AhpD\, (M^{-1}) \times 10^7$ for control and three concentrations of mycopyrin 5.

DTNB assay was conducted with 100 nM Lpd, 175 nM DlaT and variable amounts of AhpD (10, 20, 30, 40, 60, 100, and 150 nM) without or at fixed concentrations of Mycopyrin 5 of 7 µM, 15 µM, and 45 µM. As shown in FIG. 2, Mycopyrin 5 is a competitive inhibitor of DlaT versus AhpD.

Figure 3:
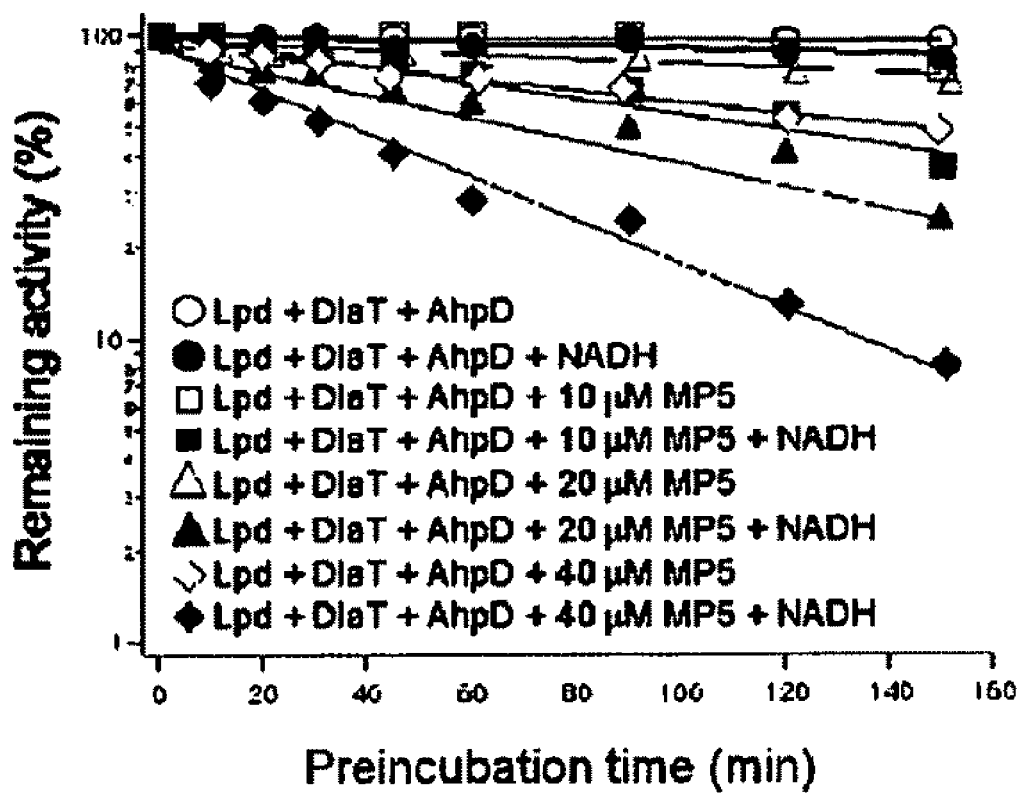
FIG. 3 is a graph showing percent remaining activity versus preincubation time for various concentrations and mixtures of dihydrolipoamide acyltransferase (DlaT), lipoamide dehydrogenase (Lpd), alkylhydroperoxide reductase subunit D (AhpD), NADH and mycopyrin 5.

Reaction mixtures containing 200 nM Lpd, 350 nM DlaT, 200 nM AceE with or without 1 mM NAD+, 1 mM pyruvate, 250 mM CoA and 10 or 40 mM D155931 were preincubated at room temperature and 100 ml aliquots tested for remaining activity over time by PDH assay. As shown in FIG. 3, Mycopyrin 5 is an irreversible inhibitor of DlaT in presence of NADH. Reaction mixtures containing 200 nM Lpd, 350 nM DlaT, 36 nM AhpD with or without 500 µM NADH and 10, 20 or 40 µM of Mycopyrin 5 were preincubated at room temperature and 50 µl aliquots tested for remaining activity over time by DTNB assay.

Figure 4:
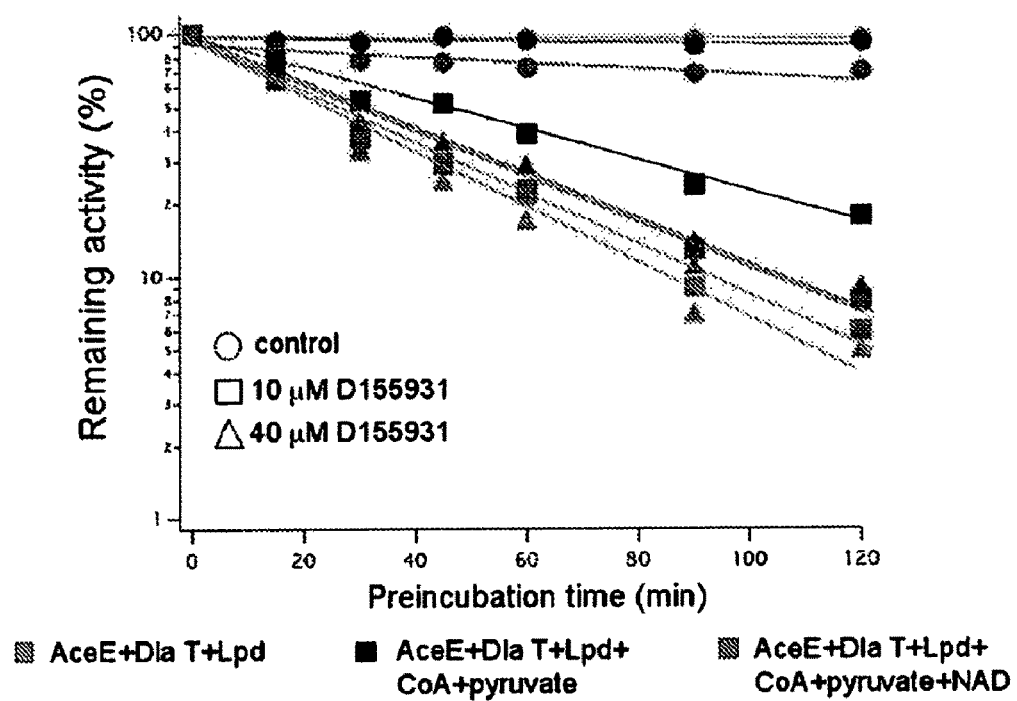
FIG. 4 is a graph showing percent remaining activity versus preincubation time for various concentrations and mixtures of dihydrolipoamide acyltransferase (DlaT), lipoamide dehydrogenase (Lpd), NAD, the E1 component of pyruvate dehydrogenase (AceE), pyruvate, Coenzyme A and mycopyrin 5.

Reaction mixtures containing 200 nM Lpd, 350 nM DlaT, 36 nM AhpD with or without 500 µM NADH and 10, 20, or 40 µM Mycopyrin 5 were preincubated at room temperature and 50 µl aliquots tested for remaining activity over time by DTNB assay. As shown in FIG. 4, Mycopyrin 5 is a time-dependent, substrate-independent inhibitor of Mtb's PDH.

Figure 5:
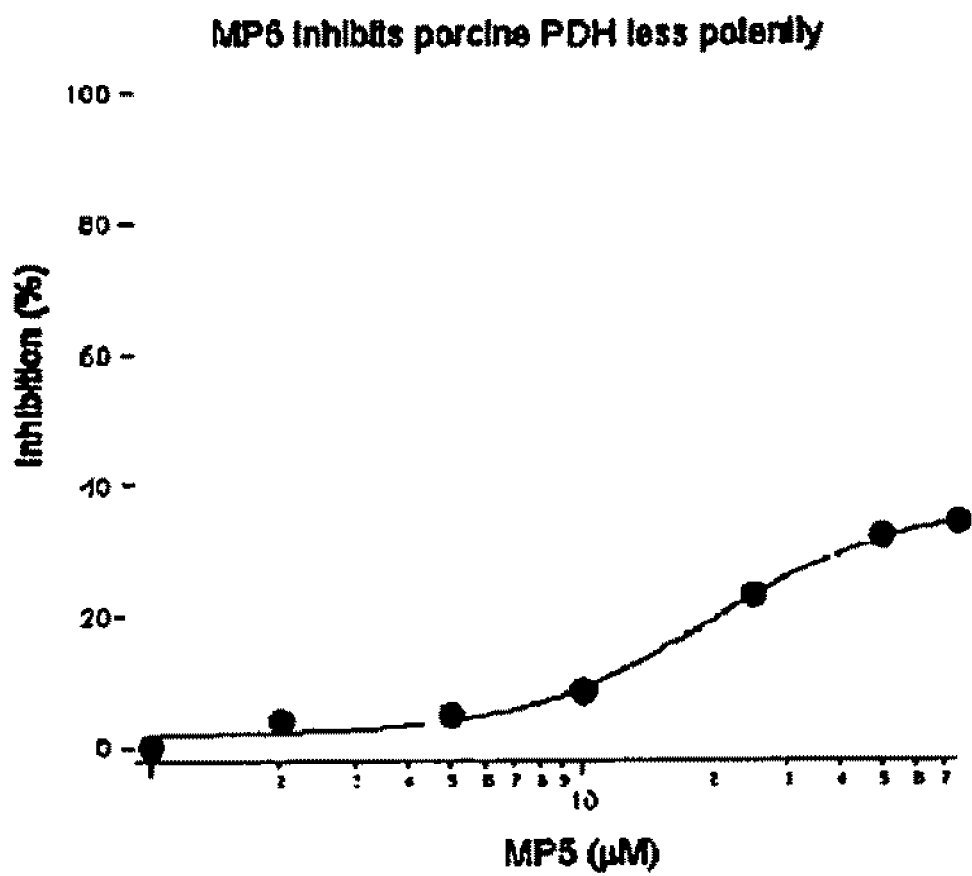
FIG. 5 is a graph showing the percent inhibition of porcine pyruvate dehydrogenase (PDH) as a function of the concentration of mycopyrin 5.

PDH complex from porcine heart (Sigma) was gel filtered on Sephadex G-100 to remove excess BSA (bovine serum albumin) and tested for activity using PDH assay in the presence of increasing concentrations of Mycopyrin 5. As shown in FIG. 5, Mycopyrin 5 does not inhibit porcine PDH up the limit of its solubility.

Figure 6:
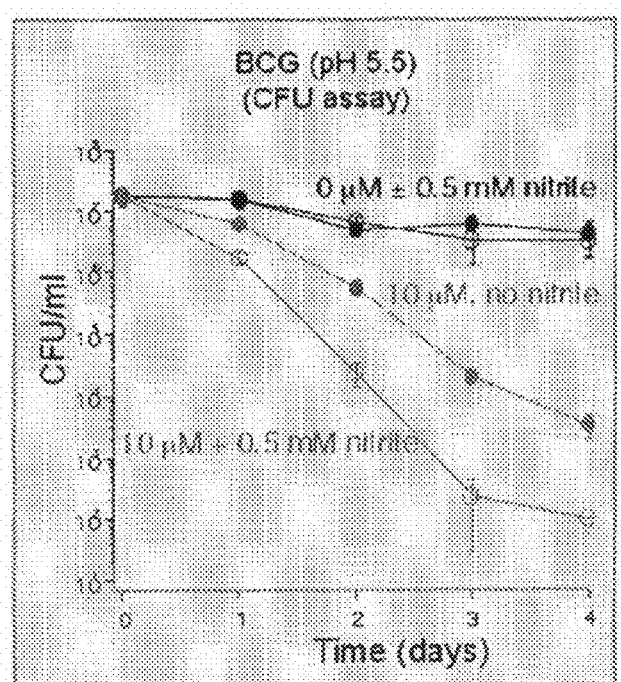
FIG. 6 is a graph showing the number of colony forming units (CFU) of *Mycobacterium bovis* var. Bacille Calmette Guerin (BCG) per mL as a function of time in the presence of 0.5 mM nitrite and 10 μM mycopyrin In some embodiments, Y in the compound of Formula I is chosen from $(C_1-C_{10})$alkylene; $(C_1-C_{10})$oxaalkylene; $(C_1-C_{10})$alkylene in which one or more hydrogens is replaced with aryl, substituted aryl or heteroaryl; aryl; and substituted aryl.
Figure 7:
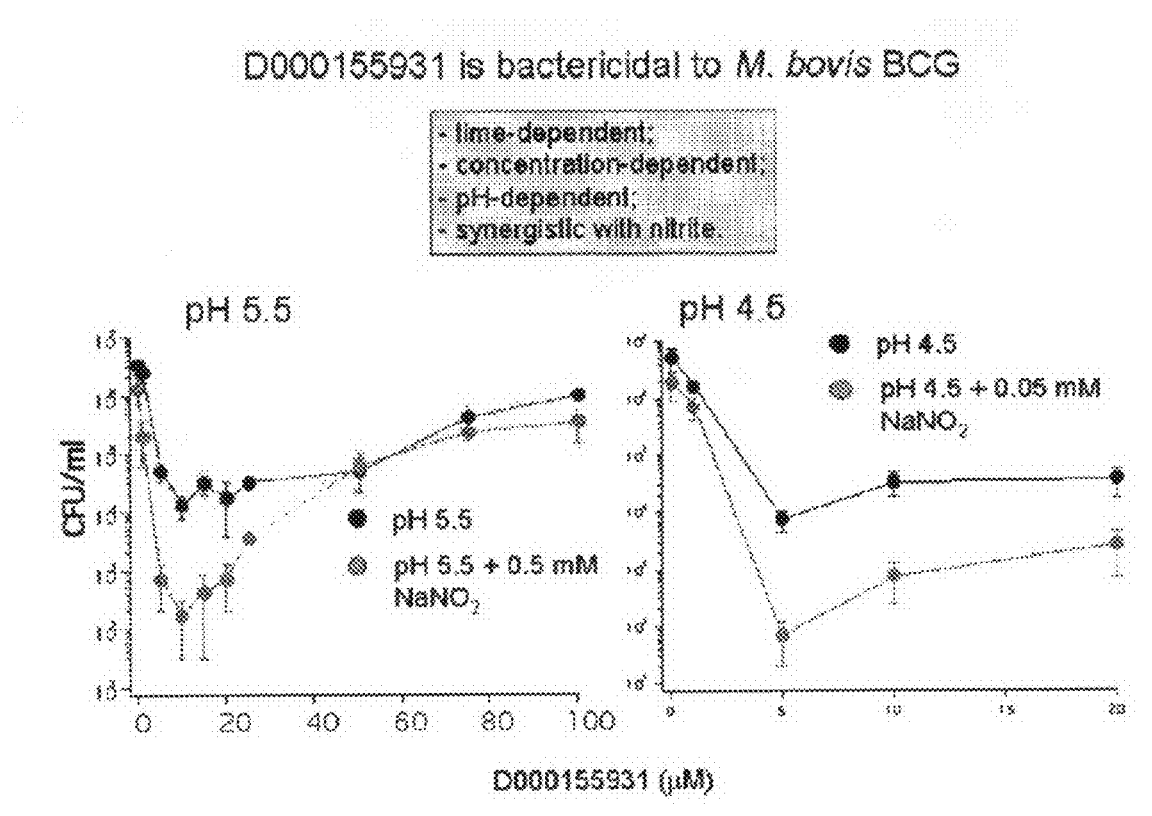

As shown in FIGS. 6 and 7, Mycopyrin 5 is bactericidal to M. bovis BCG. Mycopyrin 5 kills Mycobacterium bovis var. Bacille Calmette Guerin (BCG) when the BCG is non-replicating, and does so in synergy with nitrite at mildly acidic pH.

(pH 5.5) or 0.05 mM NaNO$_2$ (pH 4.5) in 96 well plates in 200 µl for 4 days and plated for CFU counts after serial dilution in 7H9, pH 6.6.

Figure 8:
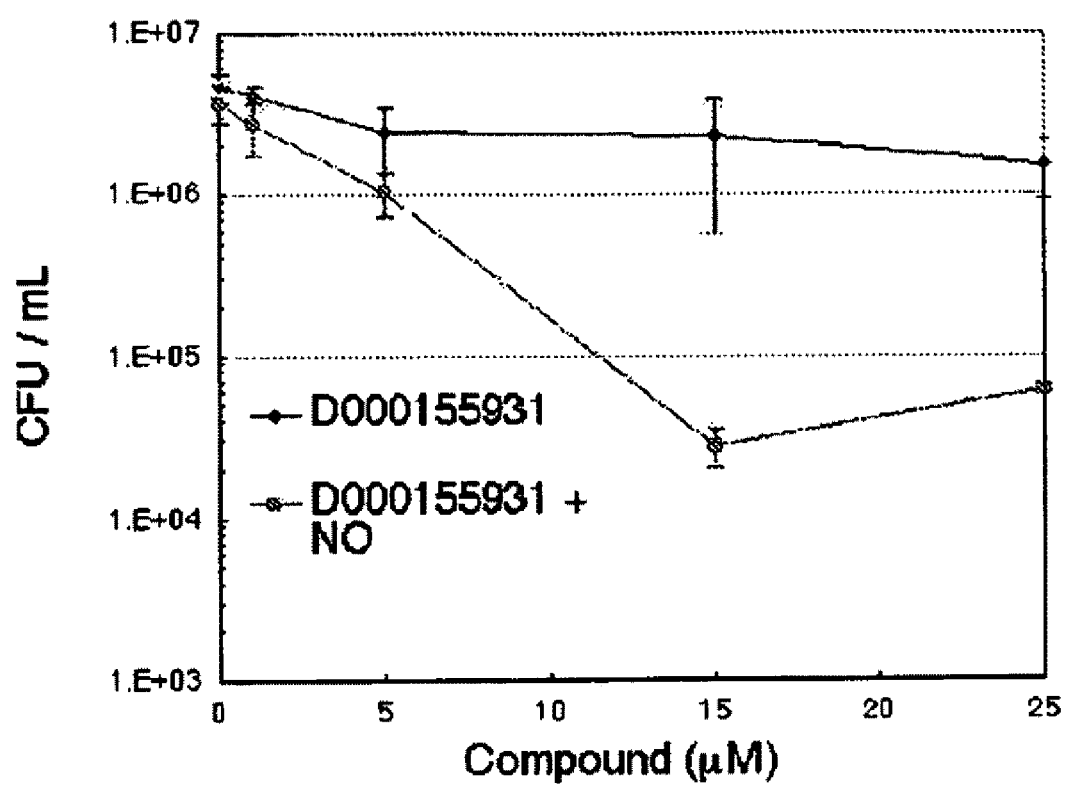

Mycopyrin 5 is also bactericidal to *Mycobacterium tuberculosis*. *M. tuberculosis* was grown in 7H9+0.2% glycerol+ 0.05% Tween-80+10% ADN, pH 6.6. CFU were enumerated on 7H11 agar plates with 10% OADC enrichment. Mid-log cultures (A$_{580}$ 0.8-1.0) were prepared as single cell suspensions in 7H9 at pH 5.5 or pH 4.5 and diluted to 0.1 (A$_{580}$). Inoculum was determined by CFU. Bacteria were incubated with compounds plus or minus 0.5 mM NaNO$_2$ (pH 5.5) or 0.05 NaNO$_2$ (pH 4.5) in 96 well plates in 200 µl for 4 days and plated for CFU counts after serial dilution in 7H9, pH 6.6. The results are shown in FIG. 8.

Figure 9:
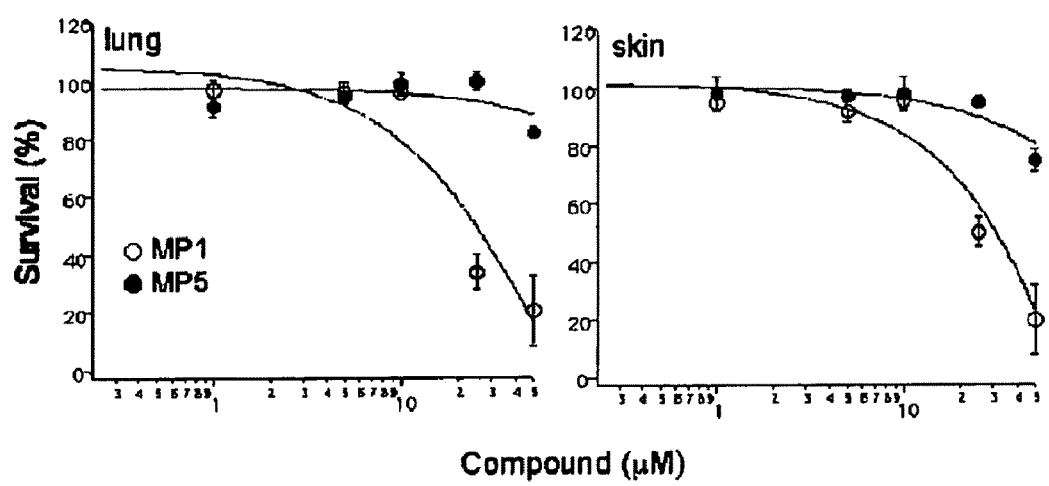

Primary human fibroblasts from skin (ATCC CRL-1634) or lung (ATCC CCL-202) were seeded in 96-wells at 1×10$^4$ cells/well in 100 p. 1 of DMEM media. Next day compounds were added at 1, 5, 10, 25 and 50 µM and incubated with cells for additional 24 hours. MTT assay (Sigma) was used to determine cell viability. DMSO was used as vehicle control. As shown in FIG. 9, Mycopyrin 5 does not kill primary, normal human skin or lung fibroblasts.

As shown in Table 22, Mycopyrin 5 kills gram positive bacterial pathogens *Staphylococcus aureus* and *Enterococcus faecalis*. Bacteria were grown to mid-logarithmic phase, diluted to A$_{600}$=0.1 and inoculated in 200 µl in 96-well plates in the presence of serial dilutions of compounds or vehicle control (DMSO). MICs (minimal concentrations that prevented bacterial growth) were determined at A$_{600}$ after 24 hours incubation at 37° C.

TABLE 22

Bacterial and yeast MICs for Mycopyrin 5 at 10$^4$-10$^5$ CFU/mL inoculum

|  | MIC pH 6.6 | | MIC pH 5.5 | |
|---|---|---|---|---|
|  | µM | µg/ml | µM | µg/ml |
| *Escherichia coli* | >50 | >22 | >50 | >22 |
| *Salmonella tryphimurium* | >50 | >22 | >50 | >22 |
| *Pseudomonas aeruginosa* | >50 | >22 | >50 | >22 |
| *Staphylococcus aureus* (brain heart infusion) | >50 | >22 | 5 | 2.2 |
| *Staphylococcus aureus* (nutrient broth) | 2.5 | 1.1 | 1 | 0.43 |
| *Enterococcus faecalis* | >50 | >22 | 5 | 2.2 |
| *Candida albicans* | >50 | >22 | >50 | >22 |

While embodiments of the invention have been described in conjunction with the detailed description thereof, the foregoing description is intended to illustrate and not limit the scope of the invention, which is defined by the scope of the appended claims. Other aspects, advantages, and modification are within the scope of the following claims.

What is claimed is:

1. A method of treating infection with *Mycobacterium tuberculosis* comprising administering to a subject a therapeutically effective amount of a compound of formula I:

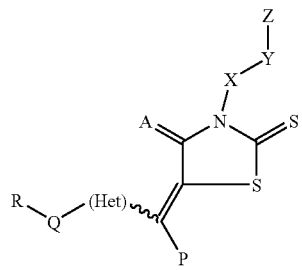

wherein:
A is chosen from oxygen and sulfur;
X is chosen from the group consisting of a direct bond, (C$_1$-C$_6$)alkylene in which one of the hydrogens is optionally replaced with a group —(CH$_2$)$_q$COOH wherein q is 0-6, —NH—, —NHSO$_2$—, and —NHC(=O)—;
Y is chosen from the group consisting of
(C$_1$-C$_{10}$)alkylene,
(C$_1$-C$_{10}$)oxaalkylene,
(C$_1$-C$_{10}$)alkylene in which one or more hydrogens is replaced with (C$_1$-C$_6$)alkyl, substituted (C$_1$-C$_6$) alkyl, aryl, substituted aryl or heteroaryl,
aryl,
substituted aryl,
heterocyclyl, and
cycloalkyl;
Z is (CH$_2$)$_p$—R$^1$ where p is 0-6;
Q is chosen from the group consisting of a direct bond, -oxygen-, —CH$_2$—, —CH$_2$O—, —CH$_2$S—, —O—C(=O)—, —C(=O)O— and —C(=O)—NR$^{13}$—;
R$^1$ is chosen from the group consisting of —COOR$^3$, —OR$^4$, —P(=O)(OR$^5$)$_2$, —O—C(=O)NR$^6$R$^7$, —SO$_2$NR$^8$R$^9$, —CONR$^{10}$R$^{11}$, —OCH$_2$—COOR$^3$, —CO—(C$_1$-C$_6$alkyl), —CO—(C$_1$-C$_6$alkyl)-OH, and —CO—(C$_1$-C$_6$alkyl)COOH;
R$^3$ is chosen from the group consisting of H, (C$_1$-C$_{10}$)alkyl, (C$_1$-C$_{10}$)oxaalkyl, hydroxy(C$_1$-C$_{10}$)alkyl, hydroxy(C$_1$-C$_{10}$)oxaalkyl, (C$_1$-C$_{10}$)azaalkyl, hydroxy(C$_1$-C$_{10}$) azaalkyl and (C$_1$-C$_{10}$)alkyl-OPO$_3$H;
R$^4$, R$^5$, R$^6$, R$^7$, R$^8$, and R$^{13}$ are chosen from H and (C$_1$-C$_6$) alkyl;
R$^9$ is chosen from the group consisting of H, (C$_1$-C$_6$)alkyl and —C(=O)R$^{12}$;
R$^{10}$ and R$^{11}$ are each independently chosen from the group consisting of H, (C$_1$-C$_6$)alkyl and (C$_1$-C$_6$)hydroxyalkyl;
R$^{12}$ is chosen from the group consisting of (C$_1$-C$_6$)alkyl, aryl and heteroaryl;
P is chosen from the group consisting of H, (C$_1$-C$_6$)alkyl, O(C$_1$-C$_6$)alkyl and F;
Het is a 5-membered or 6-membered heterocyclic ring; and
R is chosen from optionally substituted aryl and heterocyclyl;
with the provisos that when —X—Y—Z is CH$_2$CH$_2$COOH, -Het-Q-R is not 5-(3-trifluoromethylphenyl)-furan-2-yl, and when —X—Y—Z is CH$_2$COOH, -Het-Q-R is not 5-(2,3-dichlorophenyl)-furan-2-yl.

2. A method for inhibiting bacterial dihydrolipoamide acyltransferase (DlaT), which comprises contacting the DlaT enzyme with a therapeutically effective amount of a compound of formula I:

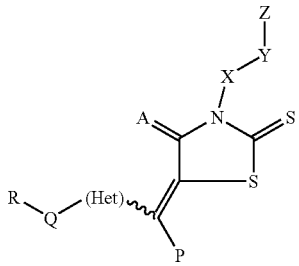

wherein:

A is chosen from oxygen and sulfur;

X is chosen from the group consisting of a direct bond, $(C_1-C_6)$alkylene in which one of the hydrogens is optionally replaced with a group —$(CH_2)_q$COOH wherein q is 0-6, —NH—, —NHSO$_2$—, and —NHC(=O)—;

Y is chosen from the group consisting of $(C_1-C_{10})$alkylene, $(C_1-C_{10})$oxaalkylene, $(C_1-C_{10})$alkylene in which one or more hydrogens is replaced with (a) $(C_1-C_6)$alkyl, (b) substituted $(C_1-C_6)$alkyl, (c) aryl, (d) substituted aryl or (e) heteroaryl, aryl, substituted aryl, heterocyclyl, and cycloalkyl;

Z is $(CH_2)_p$—$R^1$ where p is 0-6;

Q is chosen from the group consisting of a direct bond, -oxygen-, —CH$_2$—, —CH$_2$O—, —CH$_2$S—, —O—C(=O)—, —C(=O)O— and —C(=O)—NR$^{13}$—;

$R^1$ is chosen from the group consisting of —COOR$^3$, —OR$^4$, —P(=O)(OR$^5$)$_2$, —O—C(=O)NR$^6$R$^7$, —SO$_2$NR$^8$R$^9$, —CONR$^{10}$R$^{11}$, —OCH$_2$—COOR$^3$, —CO—(C$_1$-C$_6$alkyl), —CO—(C$_1$-C$_6$alkyl)-OH, and —CO—(C$_1$-C$_6$alkyl)COOH;

$R^3$ is chosen from the group consisting of H, $(C_1-C_{10})$alkyl, $(C_1-C_{10})$oxaalkyl, hydroxy$(C_1-C_{10})$alkyl, hydroxy$(C_1-C_{10})$oxaalkyl, $(C_1-C_{10})$azaalkyl, hydroxy$(C_1-C_{10})$azaalkyl and $(C_1-C_{10})$alkyl-OPO$_3$H;

$R^4$, $R^5$, $R^6$, $R^7$, $R^8$, and $R^{13}$ are chosen from H and $(C_1-C_6)$alkyl;

$R^9$ is chosen from the group consisting of H, $(C_1-C_6)$alkyl and —C(=O)R$^{12}$;

$R^{10}$ and $R^{11}$ are each independently chosen from the group consisting of H, $(C_1-C_6)$alkyl and $(C_1-C_6)$hydroxyalkyl;

$R^{12}$ is chosen from the group consisting of $(C_1-C_6)$alkyl, aryl and heteroaryl;

P is chosen from the group consisting of H, $(C_1-C_6)$alkyl, O$(C_1-C_6)$alkyl and F;

Het is a 5-membered or 6-membered heterocyclic ring; and

R is chosen from optionally substituted aryl and heterocyclyl;

with the provisos that when —X—Y—Z is CH$_2$CH$_2$COOH, -Het-Q-R is not 5-(3-trifluoromethylphenyl)-furan-2-yl, and when —X—Y—Z is CH$_2$COOH, -Het-Q-R is not 5-(2,3-dichlorophenyl)-furan-2-yl.

3. A method for treating tuberculosis and/or an infection caused by *Staphylococcus aureus* or *Enterococcus faecalis*, comprising administering to a mammal in need of such treatment a therapeutically effective amount of a compound of formula I.

4. A method of treating tuberculosis in a subject infected with a mycobacterium other than *Mycobacterium leprae*, comprising administering to a subject (a) a therapeutically effective amount of a compound of formula I of claim 1; and (b) a therapeutically effective amount of a second therapeutic agent having established or presumptive activity in the treatment of tuberculosis.

5. A method according to claim 4, wherein said second therapeutic agent is selected from the group consisting of rifampin, isoniazid, pyrazinamide, ethambutol, streptomycin, cycloserine, PA-824, and moxafloxacin.

6. A method according to claim 1 in which said compound of formula I is administered together with at least one second therapeutic agent.

7. A method according to claim 4 in which said compound of formula I is administered simultaneously with said at least one second therapeutic agent.

8. A method according to claim 4 in which said compound of formula I is administered sequentially with said at least one second therapeutic agent.

9. A method according to claim 6 wherein said at least one other therapeutic agent is selected from the group consisting of rifampin, isoniazid, pyrazinamide, ethambutol, streptomycin, cycloserine, PA-824, and moxafloxacin.

10. A method according to claim 1 wherein the compound is a compound of formula I where (a) when X is a direct bond, Y is phenyl, Z is —COOH and is located at the 3-position of the phenyl ring, P is H, HET is furan-2-yl, and -Q-R is at the 5-position of the furan ring, then -Q-R is 2-chlorophenyl, i.e, the compound is 3-[5[[5-(2-chlorophenyl)-2-furanyl]methylene]-4-oxo-2-thioxo-3-thiazolidinyl]benzoic acid, (b) when X is a direct bond, Y is phenyl, Z is COOR$^3$ or CONR$^{10}$R$^{11}$ wherein R$^3$ is $(C_1-C_{10})$oxaalkyl, hydroxy$(C_1-C_{10})$oxaalkyl, hydroxy$(C_1-C_{10})$alkyl, $(C_1-C_{10})$azaalkyl, hydroxy$(C_1-C_{10})$azaalkyl or $(C_1-C_{10})$alkyl-OPO$_3$H, R$^{10}$ is H and R$^{11}$ is $(C_1-C_6)$hydroxyalkyl, A is oxygen, P is H, Het is furan-2-yl, and Q is a direct bond at the 5-position of the furan ring, then R is halogen-substituted phenyl, or (c) when X is a direct bond or $(C_1-C_6)$alkylene, Y is heterocyclyl or cycloalkyl.

11. A method according to claim 1 wherein A in the compound of Formula I is oxygen.

12. A method according to claim 1 wherein Y in the compound of Formula I is chosen from the group consisting of $(C_1-C_{10})$alkylene; $(C_1-C_{10})$oxaalkylene; $(C_1-C_{10})$alkylene in which one or more hydrogens is replaced with aryl, substituted aryl or heteroaryl; aryl; and substituted aryl.

13. A method according to claim 1 wherein X in the compound of Formula I is a direct bond or $(C_1-C_3)$alkylene.

14. A method according to claim 1 wherein X in the compound of Formula I is a direct bond and Y is aryl or substituted aryl.

15. A method according to claim 1 wherein X in the compound of Formula I is $(C_1-C_{10})$alkylene in which one or more hydrogens is replaced with aryl or heteroaryl.

16. A method according to claim 1 wherein Z in the compound of Formula I is chosen from the group consisting of —OR$^4$, —COOR$^S$, —SO$_2$NR$^8$R$^9$ and —CONR$^{10}$R$^{11}$, and R$^3$ is chosen from H and $(C_1-C_6)$alkyl.

17. A method according to claim 1 wherein P in the compound of Formula I is H or CH$_3$.

18. A method according to claim 1 wherein Het in the compound of Formula I is chosen from the group consisting of furan, pyridine, thiazole, oxazole and benzofuran.

19. A method according to claim 1 wherein Q in the compound of Formula I is a direct bond, oxygen or CH$_2$.

20. A method according to claim 1 wherein R in the compound of Formula I is aryl or heterocyclyl.

21. A method according to claim 1 wherein X in the compound of Formula I is a direct bond; Y is chosen from $(C_1\text{-}C_{10})$alkylene and $(C_1\text{-}C_{10})$alkylene in which one or more hydrogens is replaced with phenyl or substituted phenyl; and Z is —COOH.

22. A method according to claim 1 wherein $R^1$ in the compound of Formula I is chosen from —COOR$^3$, —OR$^4$, —P(=O)(OR$^5$)$_2$, —O—C(=O)NR$^6$R$^7$, —SO$_2$NR$^8$R$^9$, and —CONR$^{10}$R$^{11}$, and $R^3$ is chosen from $(C_1\text{-}C_{10})$alkyl and $(C_1\text{-}C_{10})$oxaalkyl.

23. A method according to claim 1 wherein $R^3$ in the compound of Formula I is chosen from H, $(C_1\text{-}C_{10})$alkyl and $(C_1\text{-}C_{10})$oxaalkyl.

24. A method according to claim 1 wherein said compound of formula I has the structure:

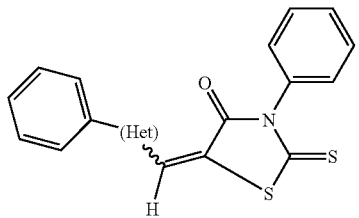

wherein the phenyl ring attached to Het is optionally substituted and the phenyl ring attached to the rhodanine ring is substituted with a group corresponding to Z and optionally further substituted.

25. A method according to claim 24 wherein said compound of formula I has the structure:

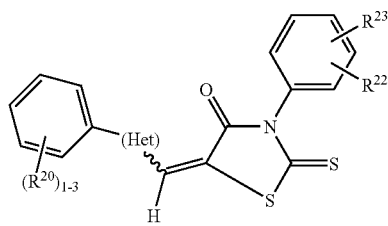

wherein $R^{20}$, Het, $R^{22}$ and $R^{23}$ have the following combinations of identities:

| Compound | $R^{20}$ | Het | $R^{22}$ | $R^{23}$ |
|---|---|---|---|---|
| A1 | 2-Cl | 2,5-furan | 3-COOH | H |
| A2 | 3-CF$_3$ | 2,5-furan | 3-COOH | H |
| A3 | 4-CH$_2$Ph | 2,5-furan | 3-COOH | H |
| A4 | 3-Cl | 2,5-furan | 3-COOH | H |
| A5 | 2-Cl | 2,6-pyridine | 3-COOH | H |
| A6 | 2-Cl | 2,5-furan | 4-SO$_2$NH$_2$ | H |
| A7 | 3,4-di-Cl | 2,5-furan | 3-COOH | H |
| A8 | 3,4-di-Cl | 2,5-furan | 4-COOH | H |
| A9 | 3,4-di-Cl | 2,5-furan | 4-SO$_2$NH$_2$ | H |
| A10 | 3-CF$_3$ | 2,5-furan | 4-COOH | H |
| A11 | 4-CH$_2$Ph | 2,5-furan | 4-COOH | H |
| A12 | 4-CH$_2$Ph | 2,5-furan | 4-SO$_2$NH$_2$ | H |
| A13 | 4-OPh | 2,5-furan | 3-COOH | H |
| A14 | 4-OPh | 2,5-furan | 4-COOH | H |
| A15 | 4-OPh | 2,5-furan | 4-SO$_2$NH$_2$ | H |
| A16 | 2-Cl | 2,5-furan | 4-COOH | H |
| A17 | 4-Cl | 2,5-furan | 4-SO$_2$NH$_2$ | H |
| A18 | 3-CF$_3$ | 2,5-furan | 4-SO$_2$NH$_2$ | H |
| A19 | 3-Cl | 2,5-furan | 4-SO$_2$NH$_2$ | H |
| A20 | 4-Cl | 2,5-furan | 4-COOH | H |
| A21 | 4-Cl | 2,5-furan | 3-COOH | H |
| A22 | 2-Cl | 2,5-furan | 4-OH | H |
| A23 | 3-CF$_3$ | 2,5-furan | 4-OH | H |
| A24 | 4-Cl | 2,5-furan | 4-OH | H |
| A25 | 2-Cl | 2,5-furan | 3-SO$_2$NH$_2$ | H |
| A26 | 3-CF$_3$ | 2,5-furan | 3-SO$_2$NH$_2$ | H |
| A27 | 4-Cl | 2,5-furan | 3-SO$_2$NH$_2$ | H |
| A28 | 3-CF$_3$ | 2,4-furan | 3-COOH | H |
| A29 | 3-CF$_3$ | 2,4-furan | 4-COOH | H |
| A30 | 3,4-di-Cl | 2,5-furan | 4-SO$_2$NHCOCH$_3$ | H |
| A31 | 3-CF$_3$ | 2,5-furan | 4-SO$_2$NHCOCH$_3$ | H |
| A32 | 3-CF$_3$ | 2,5-furan | 3-COOH | 4-OH |
| A33 | 2-Cl | 2,5-furan | 3-COOH | 4-OH |
| A34 | 4-Cl | 2,5-furan | 3-COOH | 4-OH |
| A35 | 2,4-di-Cl | 2,5-furan | 3-COOH | H |
| A36 | 2,5-di-Cl | 2,5-furan | 3-COOH | H |
| A37 | 2-Cl | 2,5-furan | 3-SO$_2$NHCOCH$_3$ | H |
| A38 | 3-CF$_3$ | 2,5-furan | 3-SO$_2$NHCOCH$_3$ | H |
| A39 | 2,6-di-Cl | 2,5-furan | 3-COOH | H |
| A40 | 2,4-di-Cl | 2,5-furan | 3-COOH | 4-OH |
| A41 | 2,5-di-Cl | 2,5-furan | 3-COOH | 4-OH |
| A42 | 2,6-di-Cl | 2,5-furan | 3-COOH | 4-OH |
| A43 | 3-CF$_3$ | 2,5-furan | 3-COOH | H |

-continued

| Compound | $R^{20}$ | Het | $R^{22}$ | $R^{23}$ |
| --- | --- | --- | --- | --- |
| A44 | 2-Cl-5-CF$_3$ | 2,5-furan | 3-COOH | H |
| A45 | 4-Cl | 2,5-furan | 4-OCH$_2$COOH | H |
| A46 | 4-CH(CH$_3$)$_2$ | 2,5-furan | 3-COOH | H |
| A47 | 4-CH(CH$_3$)$_2$ | 2,5-furan | 3-COOH | 4-OH |
| A48 | 4-COPh | 2,5-furan | 3-COOH | H |
| A49 | 2-Cl | 2,5-furan | 3-OH | H |
| A50 | 3-CF$_3$ | 2,5-furan | 3-OH | H |
| A51 | 4-Cl | 2,5-furan | 3-OH | H |
| A52 | 4-CH(CH$_3$)$_2$ | 2,5-furan | 3-OH | H |
| A53 | 4-CH$_2$SPh | 2,5-furan | 3-COOH | H |
| A54 | 3-CH(CH$_3$)$_2$ | 2,5-furan | 3-COOH | H |
| A55 | 3-CH(CH$_3$)$_2$ | 2,5-furan | 3-OH | H |
| A56 | 4-cyclohexyl | 2,5-furan | 3-COOH | H |
| A57 | 4-cyclohexyl | 2,5-furan | 3-COOH | 4-OH |
| A58 | 4-C(CH$_3$)$_3$ | 2,5-furan | 3-COOH | H |
| A59 | 4-C(CH$_3$)$_3$ | 2,5-furan | 3-COOH | 4-OH |
| A60 | 4-Cl | 2,5-furan | 3-OCH$_2$COOH | H |
| A61 | 3-CH(CH$_3$)$_2$ | 2,5-furan | 3-COOH | 4-OH |
| A62 | 4-CH$_2$SPh | 2,5-furan | 3-COOH | 4-OH |
| A63 | 3-CH(CH$_3$)$_2$ | 2,5-furan | 3-OCH$_2$COOH | H |
| A64 | 4-CH$_2$CH(CH$_3$)$_2$ | 2,5-furan | 3-COOH | H |
| A65 | 4-CH$_2$CH(CH$_3$)$_2$ | 2,5-furan | 3-COOH | 4-OH |
| A66 | 2-Cl | 2,5-furan | 3-COOH | 4-Cl |
| A67 | 3-CF$_3$ | 2,5-furan | 3-COOH | 4-Cl |
| A68 | 4-Cl | 2,5-furan | 3-COOH | 4-Cl |
| A69 | 2-OCF$_3$ | 2,5-furan | 3-COOH | 4-Cl |
| A70 | 2-OCF$_3$ | 2,5-furan | 3-COOH | H |
| A71 | 2-Cl | 2,5-furan | 3-COOH | 6-Cl |
| A72 | 4-Cl | 2,5-furan | 3-COOH | 6-Cl |
| A73 | 3-CF$_3$ | 2,5-furan | 3-COOH | 6-Cl |
| A74 | 2-Cl | 2,5-furan | 3-COOH | 6-OCH$_3$ |
| A75 | 2-Cl | 2,5-furan | 3-CONH$_2$ | H |
| A76 | 3-CF$_3$ | 2,5-furan | 3-CONH$_2$ | H |
| A77 | 4-Cl | 2,5-furan | 3-CONH$_2$ | H |
| A78 | 2-Cl | 2,5-furan | 3-COOH | 6-CH$_3$ |
| A79 | 2-Cl | 2,5-furan | 3-COOH | 2-CH$_3$ |
| A80 | 4-C(CH$_3$)$_3$ | 2,5-furan | 3-COOH | 6-CH$_3$ |
| A81 | 4-C(CH$_3$)$_3$ | 2,5-furan | 3-COOH | 2-CH$_3$ |
| A82 | 4-cyclohexyl | 2,5-furan | 3-COOH | 6-CH3 |
| A83 | 4-cyclohexyl | 2,5-furan | 3-COOH | 2-CH$_3$ |
| A84 | 4-CH$_2$(4-Cl—Ph) | 2,5-furan | 3-COOH | H |
| A86 | 3-CF$_3$ | 2,5-furan | 3-COOH | 6-OCH$_3$ |
| A87 | 4-Cl | 2,5-furan | 3-COOH | 6-OCH$_3$ |
| A88 | 2-Cl | 2,5-furan | 3-COOH | 5-NO$_2$ |
| A89 | 3-CF$_3$ | 2,5-furan | 3-COOH | 5-NO$_2$ |
| A90 | 4-Cl | 2,5-furan | 3-COOH | 5-NO$_2$ |
| A91 | 4-CH$_2$CH(CH$_3$)$_2$ | 2,5-furan | 3-COOH | 6-OCH$_3$ |
| A92 | 4-CH$_2$CH(CH$_3$)$_2$ | 2,5-furan | 3-COOH | 6-Cl |
| A93 | 3-CH(CH$_3$)$_2$ | 2,5-furan | 3-COOH | 6-OCH$_3$ |
| A94 | 4-cyclopentyl | 2,5-furan | 3-COOH | H |
| A95 | 4-C(CH$_3$)$_2$Ph | 2,5-furan | 3-COOH | H |
| A96 | 4-C(CH$_3$)$_2$Ph | 2,5-furan | 3-COOH | 6-Cl |
| A97 | 4-C(CH$_3$)$_2$Ph | 2,5-furan | 3-COOH | 6-OCH$_3$ |
| A98 | 4-C(CH$_3$)$_2$Ph | 2,5-furan | 3-COOH | 2-CH$_3$ |
| A99 | 2-Cl | 2,5-furan | 3-COOH | 6-F |
| A100 | 4-C(CH$_3$)$_3$ | 2,5-furan | 3-COOH | 6-F |
| A101 | 4-cyclohexyl | 2,5-furan | 3-COOH | 6-F |
| A102 | 4-C(CH$_3$)$_2$Ph | 2,5-furan | 3-COOH | 6-CH$_3$ |
| A103 | 3-CF$_3$ | 2,5-furan | 3-COOH | 6-F |
| A104 | 4-Cl | 2,5-furan | 3-COOH | 6-F |
| A105 | 3,4-di-Cl | 2,5-furan | 3-COOH | 6-F |
| A106 | 2,6-di-Cl | 2,5-furan | 3-COOH | 6-F |
| A107 | 3,4-di-Cl | 2,5-furan | 3-COOH | 6-Cl |
| A108 | 3,4-di-Cl | 2,5-furan | 3-COOH | 4-Cl |
| A109 | 2,6-di-Cl | 2,5-furan | 3-COOH | 4-Cl |
| A110 | 2,6-di-Cl | 2,5-furan | 3-COOH | 6-Cl |
| A111 | 3,4-di-Cl | 2,5-furan | 3-COOH | 2-CH$_3$ |
| A112 | 2,6-di-Cl | 2,5-furan | 3-COOH | 2-CH$_3$ |
| A113 | 3,4-di-Cl | 2,5-furan | 3-COOH | 6-CH$_3$ |
| A114 | 2,6-di-Cl | 2,5-furan | 3-COOH | 6-CH$_3$ |
| A115 | 3-OH-4-COOH | 2,5-furan | 3-COOH | H |
| A116 | 4-N(Me)$_2$ | 2,5-furan | 3-COOH | H |
| A117 | 2,3-di-Cl | 2,5-furan | 3-COOH | H |
| A118 | 2-Cl | 2,5-furan | 3-(CH$_2$)$_2$COOH | H |
| A119 | 3-Cl | 2,5-furan | 3-(CH$_2$)$_2$COOH | H |
| A120 | 4-Cl | 2,5-furan | 3-(CH$_2$)$_2$COOH | H |
| A121 | 3,5-di-Cl | 2,5-furan | 3-COOH | H |
| A122 | 4-CH$_2$N(Me)$_2$ | 2,5-furan | 3-COOH | H |

-continued

| Compound | $R^{20}$ | Het | $R^{22}$ | $R^{23}$ |
|---|---|---|---|---|
| A123 | 4-Br | 2,5-furan | 3-COOH | H |
| A124 | 2-Cl-4-OH | 2,5-furan | 3-COOH | H |
| A125 | 3-N(Me)$_2$ | 2,5-furan | 3-COOH | H |
| A126 | 4-acetylene | 2,5-furan | 3-COOH | H |
| A127 | 3-NO$_2$ | 2,5-furan | 3-COOH | H |
| A128 | 3-NO$_2$ | 2,5-furan | 3-COOH | 6-Cl |
| A129 | 2-NO$_2$ | 2,5-furan | 3-COOH | H |
| A130 | 4-NO$_2$ | 2,5-furan | 3-COOH | H |
| A131 | 2-NO$_2$-4-Cl | 2,5-furan | 3-COOH | H |
| A132 | 2-Br | 2,5-furan | 3-COOH | H |
| A133 | 2-OH-4-C(CH$_3$)$_3$ | 2,5-furan | 3-COOH | H |
| A134 | 2-CH$_3$ | 2,5-furan | 3-COOH | H |
| A135 | 2-OCH$_3$ | 2,5-furan | 3-COOH | H |
| A136 | 4-morpholine | 2,5-furan | 3-COOH | H |
| A137 | 4-morpholine | 2,5-furan | 3-COOH | 6-Cl |
| A138 | 2-F | 2,5-furan | 3-COOH | H |
| A139 | 2-OCH$_3$ | 2,5-furan | 3-COOH | 6-F |
| A140 | 2-OCH$_3$ | 2,5-furan | 3-COOH | 6-Cl |
| A141 | 2-OCH$_3$ | 2,5-furan | 3-COOH | 6-CH$_3$ |
| A142 | 2-OCH$_3$ | 2,5-furan | 3-COOH | 2-CH$_3$ |
| A143 | 2-CN-3-F | 2,5-furan | 3-COOH | H |
| A144 | 2-CH$_3$ | 2,5-furan | 3-COOH | 6-F |
| A145 | 2-CH$_3$ | 2,5-furan | 3-COOH | 6-CH$_3$ |
| A146 | 3-Cl-4-OCH$_3$ | 2,5-furan | 3-COOH | H |
| A147 | 4-CH$_3$ | 2,5-furan | 3-COOH | H |
| A148 | 2-CH$_3$-4-F | 2,5-furan | 3-COOH | H |
| A149 | 2-CH$_3$-4-F | 2,5-furan | 3-COOH | 6-F |
| A150 | 2-F-4-CH$_3$ | 2,5-furan | 3-COOH | H |
| A151 | 2-F-4-CH$_3$ | 2,5-furan | 3-COOH | 6-F |
| A152 | 4-OCH$_3$ | 2,5-furan | 3-COOH | H |
| A153 | 2,4-di-F | 2,5-furan | 3-COOH | H |
| A154 | 2,4-di-F | 2,5-furan | 3-COOH | 6-F |
| A155 | 2,4-di-CH$_3$ | 2,5-furan | 3-COOH | H |
| A156 | 2,4-di-CH$_3$ | 2,5-furan | 3-COOH | 6-F |
| A157 | 2-NHCOOC(CH$_3$)$_3$ | 2,5-furan | 3-COOH | H |
| A158 | 2-NH$_2$•HCl | 2,5-furan | 3-COOH | H |
| A159 | 2-CH$_3$-4-OCH$_3$ | 2,5-furan | 3-COOH | H |
| A160 | 2-CH$_3$-4-OCH$_3$ | 2,5-furan | 3-COOH | 6-F |
| A161 | 2-CH$_3$ | 2,6-pyridine | 3-COOH | 6-F |
| A162 | 2-OH | 2,5-furan | 3-COOH | H |
| A163 | 2-OH | 2,5-furan | 3-COOH | 6-F |
| A164 | 2-NHCOOC(CH$_3$)$_3$ | 2,5-furan | 3-COOH | 6-F |
| A165 | 4-CH$_3$ | 2,5-furan | 3-COOH | 6-F |
| A166 | 4-OCH$_3$ | 2,5-furan | 3-COOH | 6-F |
| A167 | 2,4-di-OCH$_3$ | 2,5-furan | 3-COOH | H |
| A168 | 2,4-di-OCH$_3$ | 2,5-furan | 3-COOH | 6-F |
| A169 | 2-CH$_3$-4-Cl | 2,5-furan | 3-COOH | H |
| A170 | 2-CH$_3$-4-Cl | 2,5-furan | 3-COOH | 6-F |
| A171 | 2,6-di-CH$_3$ | 2,5-furan | 3-COOH | H |
| A172 | 2,6-di-CH$_3$ | 2,5-furan | 3-COOH | 6-F |
| A173 | 2-CH$_3$ | 1,3-phenyl | 3-COOH | H |
| A174 | 2-CH$_3$ | 1,3-phenyl | 3-COOH | 6-F |
| A175 | 2-OCH$_3$-4-F | 2,5-furan | 3-COOH | H |
| A176 | 2-OCH$_3$-4-F | 2,5-furan | 3-COOH | 6-F |
| A177 | 3-F-4-OCH$_3$ | 2,5-furan | 3-COOH | H |
| A178 | 3-F-4-OCH$_3$ | 2,5-furan | 3-COOH | 6-F |
| A179 | 2-OCH$_2$Ph | 2,5-furan | 3-COOH | H |
| A180 | 2-OCH$_2$Ph | 2,5-furan | 3-COOH | 6-F |
| A181 | 2,4,6-tri-CH$_3$ | 2,5-furan | 3-COOH | 6-F |
| A182 | 2-CH$_3$-4-N(CH$_3$)$_2$ | 2,5-furan | 3-COOH | H |
| A183 | 2-CH$_3$-4-N(CH$_3$)$_2$ | 2,5-furan | 3-COOH | 6-F |
| A184 | 2,4,6-tri-CH$_3$ | 2,5-furan | 3-COOH | H |
| A185 | 2-SCH$_3$ | 2,5-furan | 3-COOH | H |
| A186 | 2-SCH$_3$ | 2,5-furan | 3-COOH | 6-F |
| A187 | 2-CH$_3$ | 2,5-thiophene | 3-COOH | H |
| A188 | 2-CH$_3$ | 2,5-thiophene | 3-COOH | 6-F |
| A189 | 2-Cl | 2,5-thiophene | 3-COOH | H |
| A190 | 2-Cl | 2,5-thiophene | 3-COOH | 6-F |
| A191 | 4-N(CH$_3$)$_2$ | 2,5-furan | 3-COOH | 6-F |
| A192 | 2-OCH$_2$(2-Cl—Ph) | 1,2-phenyl | 3-COOH | H |
| A193 | 2-OPh | 2,5-furan | 3-COOH | H |
| A194 | 2-OPh | 2,5-furan | 3-COOH | 6-F |
| A195 | 2-F | 2,5-thiophene | 3-COOH | H |
| A196 | 2-F | 2,5-thiophene | 3-COOH | H |
| A197 | 2-OCH$_2$(2-Cl—Ph) | 1,2-phenyl | 3-COOH | 6-F |
| A198 | 2,6-di-CH$_3$ | 2,5-furan | 3-COOH | H |
| A199 | 2,6-di-CH$_3$ | 2,5-furan | 3-COOH | 6-F |
| A200 | 4-CF$_3$ | 2,5-furan | 3-COOH | H |

-continued

| Compound | $R^{20}$ | Het | $R^{22}$ | $R^{23}$ |
| --- | --- | --- | --- | --- |
| A201 | 4-CF$_3$ | 2,5-furan | 3-COOH | 6-F |
| A202 | 3-Ph | 2,5-furan | 3-COOH | H |
| A203 | 3-Ph | 2,5-furan | 3-COOH | 6-F |
| A204 | 4-NHCOCH$_3$ | 2,5-furan | 3-COOH | H |
| A205 | 4-NHCOCH$_3$ | 2,5-furan | 3-COOH | 6-F |
| A206 | 4-COCH$_3$ | 2,5-furan | 3-COOH | H |
| A207 | 4-COCH$_3$ | 2,5-furan | 3-COOH | 6-F |
| A208 | 2-F | 2,5-furan | 3-COOH | 6-F |
| A209 | 3-CH$_2$OH | 2,5-furan | 3-COOH | H |
| A210 | 3-CH$_2$OH | 2,5-furan | 3-COOH | 6-F |
| A211 | 4-F | 2,5-furan | 3-COOH | H |
| A212 | 4-F | 2,5-furan | 3-COOH | 6-F |
| A217 | 4-OCH$_2$CH$_3$ | 2,5-furan | 3-COOH | H |
| A218 | 4-OCH$_2$CH$_3$ | 2,5-furan | 3-COOH | 6-F |
| A219 | 4-OCH2Ph | 2,5-furan | 3-COOH | H |
| A220 | 4-OCH2Ph | 2,5-furan | 3-COOH | 6-F |
| A221 | 2-Cl | 2,5-furan | 3-COOH | 5-CF$_3$ |
| A222 | 2-F | 2,5-furan | 3-COOH | 5-CF$_3$ |
| A223 | 4-Cl | 2,5-furan | 3-COOH | 5-CF$_3$ |
| A224 | 4-CH$_3$ | 2,5-furan | 3-COOH | 5-CF$_3$ |
| A225 | 4-CH$_2$CH$_3$ | 2,5-furan | 3-COOH | 5-CF$_3$ |
| A226 | 4-O(CH$_2$)$_3$CH$_3$ | 2,5-furan | 3-COOH | H |
| A227 | 4-O(CH$_2$)$_3$CH$_3$ | 2,5-furan | 3-COOH | 6-F |
| A228 | 4-SO$_2$CH$_3$ | 2,5-furan | 3-COOH | H |
| A229 | 4-SO$_2$CH$_3$ | 2,5-furan | 3-COOH | 6-F |
| A230 | 2-Cl | 2,5-furan | 3-COOH | 5-COOH |
| A231 | 2-F | 2,5-furan | 3-COOH | 5-COOH |
| A232 | 4-Cl | 2,5-furan | 3-COOH | 5-COOH |
| A233 | 4-CH$_2$CH$_3$ | 2,5-furan | 3-COOH | 5-COOH |
| A234 | 2-CH$_3$ | 2,5-furan | 3-COOH | 5-CF$_3$ |
| A235 | 2-CH$_3$ | 2,5-furan | 3-COOH | 5-COOH |
| A236 | 3-SCH$_3$ | 2,5-furan | 3-COOH | H |
| A237 | 3-SCH$_3$ | 2,5-furan | 3-COOH | 6-F |
| A238 | 4-SCH$_3$ | 2,5-furan | 3-COOH | H |
| A239 | 4-SCH$_3$ | 2,5-furan | 3-COOH | 6-F |
| A240 | 4-OCH(CH$_3$)$_2$ | 2,5-furan | 3-COOH | H |
| A241 | 4-OCH(CH$_3$)$_2$ | 2,5-furan | 3-COOH | 6-F |
| A242 | 4-CH$_3$ | 1,3-phenyl | 3-COOH | H |
| A243 | 4-CH$_3$ | 1,3-phenyl | 3-COOH | 6-F |
| A244 | 2-Ph | 2,5-furan | 3-COOH | H |
| A245 | 2-Ph | 2,5-furan | 3-COOH | 6-F |
| A246 | 4-CH$_3$ | 1,4-phenyl | 3-COOH | H |
| A247 | 4-CH$_3$ | 1,4-phenyl | 3-COOH | 6-F |
| A248 | 4-CH$_3$ | 1,4-phenyl | 3-COOH | 5-CF$_3$ |
| A249 | 2-CH$_2$CH$_3$ | 2,5-furan | 3-COOH | H |
| A250 | 2-CH$_2$CH$_3$ | 2,5-furan | 3-COOH | 6-F |
| A251 | H | 2,4-thiazole | 3-COOH | H |
| A252 | H | 2,4-thiazole | 3-COOH | 6-F |
| A253 | 2-OCH$_3$-5-CH$_3$ | 2,5-furan | 3-COOH | H |
| A254 | 2-OCH$_3$-5-CH$_3$ | 2,5-furan | 3-COOH | 6-F |
| A255 | 2-Cl | 2,5-furan | 3-COOH | 4-F |
| A256 | 2-F | 2,5-furan | 3-COOH | 4-F |
| A257 | 2-CH$_3$ | 2,5-furan | 3-COOH | 4-F |
| A258 | 4-Cl | 2,5-furan | 3-COOH | 4-F |
| A259 | 4-F | 2,5-furan | 3-COOH | 4-F |
| A260 | 4-CH$_3$ | 2,5-furan | 3-COOH | 4-F |
| A261 | 4-NHCOCH$_3$ | 2,5-furan | 3-COOH | 5-CF$_3$ |
| A262 | 4-NHCOCH$_3$ | 2,5-furan | 3-COOH | 4-F |
| A263 | 4-(CH$_2$)$_3$CH$_3$ | 2,5-furan | 3-COOH | H |
| A264 | 4-(CH$_2$)$_3$CH$_3$ | 2,5-furan | 3-COOH | 6-F |
| A265 | 4-(CH$_2$)$_3$CH$_3$ | 2,5-furan | 3-COOH | 4-F |
| A266 | 4-(CH$_2$)$_3$CH$_3$ | 2,5-furan | 3-COOH | 5-CF$_3$ |
| A267 | 4-SO$_2$CH$_3$ | 2,5-furan | 3-COOH | 5-CF$_3$ |
| A268 | 4-SO$_2$CH$_3$ | 2,5-furan | 3-COOH | 4-F |
| A269 | 4-(CH$_2$)$_2$CH$_3$ | 2,5-furan | 3-COOH | H |
| A270 | 4-(CH$_2$)$_2$CH$_3$ | 2,5-furan | 3-COOH | 6-F |
| A271 | 4-(CH$_2$)$_2$CH$_3$ | 2,5-furan | 3-COOH | 4-F |
| A272 | 4-(CH$_2$)$_2$CH$_3$ | 2,5-furan | 3-COOH | 5-CF$_3$ |
| A274 | 2-Cl | 2,5-furan | 3-COOH | 4-N(CH$_3$)$_2$ |
| A275 | 3-Cl | 2,5-furan | 3-COOH | 4-N(CH$_3$)$_2$ |
| A279 | 2-OCH$_2$Ph | 2,5-furan | 3-COOH | 4-F |
| A280 | 2-CF$_3$ | 2,5-furan | 3-COOH | 4-F |
| A281 | 2-OCF$_3$ | 2,5-furan | 3-COOH | 4-F |
| A282 | 2-SCH$_3$ | 2,5-furan | 3-COOH | 4-F |
| A283 | 2-OPh | 2,5-furan | 3-COOH | 4-F |
| A284 | 2-Ph | 2,5-furan | 3-COOH | 4-F |
| A286 | 4-SO$_2$NHCH$_3$ | 2,5-furan | 3-COOH | H |
| A287 | 4-SO$_2$NHCH$_3$ | 2,5-furan | 3-COOH | 4-F |

-continued

| Compound | R20 | Het | R22 | R23 |
|---|---|---|---|---|
| A288 | 4-SO2NH2 | 2,5-furan | 3-COOH | H |
| A289 | 3-OH-4-COOH | 2,5-furan | H | H |
| A290 | 4-COOH | 2,5-furan | 3-OH | H |
| A291 | 4-COOH | 2,5-furan | 4-OH | H |
| A293 | 4-COOH | 2,5-furan | 3-CONH2 | H |
| A294 | 4-COOH | 2,5-furan | 4-SO2NH2 | H. |

26. A method according to claim 1 wherein said compound of formula I has the structure:

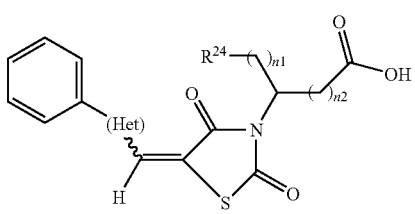

wherein n1 is 0 or 1, n2 is 0 to 4, $R^{24}$ is H, $(C_1-C_3)$alkyl or phenyl, and each of the phenyl rings is optionally substituted.

27. A method according to claim 26 wherein the compound of formula I has the structure:

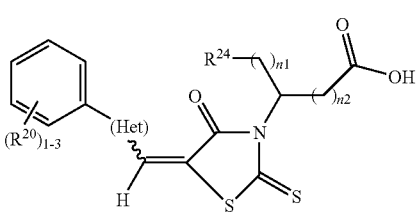

and Het, n1, n2 and $R^{24}$ have the following combinations of identities:

| Compound | R20 | Het | n1 | n2 | R24 |
|---|---|---|---|---|---|
| B1 | 2-Cl | 2,5-furan | 0 | 0 | Ph |
| B2 | 3-Cl | 2,5-furan | 0 | 0 | Ph |
| B3 | 3-CF3 | 2,5-furan | 0 | 1 | H |
| B4 | 2-CF3 | 2,5-furan | 0 | 1 | H |
| B5 | 2-Cl | 2,5-furan | 0 | 1 | H |
| B6 | 2-Cl | 2,5-furan | 0 | 0 | H |
| B7 | 2-Cl | 2,6-pyridine | 0 | 1 | H |
| B8 | 2-Cl | 2,6-pyridine | 0 | 0 | H |
| B9 | 4-Cl | 2,5-furan | 0 | 0 | Ph |
| B10 | 3,4-di-Cl | 2,5-furan | 0 | 0 | Ph |
| B11 | 2-Cl | 2,5-furan | 0 | 4 | H |
| B12 | 3-Cl | 2,5-furan | 0 | 4 | H |
| B13 | 4-Cl | 2,5-furan | 0 | 4 | H |
| B14 | 3,4-di-Cl | 2,5-furan | 0 | 4 | H |
| B15 | 2-Cl | 2,6-pyridine | 0 | 4 | H |
| B16 | 4-Ph | 2,5-furan | 0 | 0 | H |
| B17 | 4-Ph | 2,5-furan | 0 | 1 | H |
| B18 | 4-Ph | 2,5-furan | 0 | 4 | H |
| B19 | 4-Ph | 2,5-furan | 0 | 0 | Ph |
| B20 | 2-Cl-5-CF3 | 2,5-furan | 0 | 4 | H |
| B21 | 3-Cl-4-OCH3 | 2,5-furan | 0 | 4 | H |
| B22 | 3-CF3 | 2,5-furan | 0 | 4 | H |
| B23 | 2-CF3 | 2,5-furan | 0 | 4 | H |
| B24 | 2-OCF3 | 2,5-furan | 0 | 4 | H |
| B25 | 3-CF3 | 2,5-thiazole | 0 | 0 | Ph |

-continued

| Compound | R20 | Het | n1 | n2 | R24 |
|---|---|---|---|---|---|
| B26 | 4-OH | 2,5-furan | 0 | 1 | H |
| B27 | 4-OH | 2,5-furan | 0 | 4 | H |
| B28 | 4-OPh | 2,5-furan | 0 | 0 | Ph |
| B29 | 4-OH | 2,5-furan | 0 | 0 | Ph |
| B30 | 4-CH2Ph | 2,5-furan | 0 | 0 | H |
| B31 | 4-CH2Ph | 2,5-furan | 0 | 1 | H |
| B32 | 4-CH2Ph | 2,5-furan | 0 | 0 | Ph |
| B33 | 4-CH2Ph | 2,5-furan | 0 | 4 | H |
| B34 | 3-Cl | 2,5-oxazole | 0 | 4 | H |
| B35 | 3-Cl | 2,5-oxazole | 0 | 0 | Ph |
| B36 | 4-Cl | 2,5-furan | 0 | 0 | (R)-Ph |
| B37 | 4-Cl | 2,5-furan | 0 | 0 | (S)-Ph |
| B38 | 3-CF3 | 2,4-furan | 0 | 0 | Ph |
| B39 | 3-CF3 | 2,4-furan | 0 | 4 | H |
| B40 | 3-CF3 | 2,5-furan | 1 | 0 | Ph |
| B41 | 2-Cl | 2,5-furan | 1 | 0 | Ph |
| B42 | 4-Cl | 2,5-furan | 1 | 0 | Ph |
| B43 | 2,4-di-Cl | 2,5-furan | 0 | 0 | H |
| B44 | 2,4-di-Cl | 2,5-furan | 0 | 0 | Ph |
| B45 | 2,4-di-Cl | 2,5-furan | 1 | 0 | Ph |
| B46 | 2,5-di-Cl | 2,5-furan | 0 | 0 | Ph |
| B47 | 2,5-di-Cl | 2,5-furan | 1 | 0 | Ph |
| B48 | 2,6-di-Cl | 2,5-furan | 0 | 0 | Ph |
| B49 | 2,6-di-Cl | 2,5-furan | 1 | 0 | Ph |
| B50 | 3-CF3 | 2,5-furan | 0 | 0 | Ph |
| B51 | 2-Cl | 2,5-furan | 1 | 0 | Ph-(4-OH) |
| B52 | 3-CF3 | 2,5-furan | 1 | 0 | Ph-(4-OH) |
| B53 | 4-Cl | 2,5-furan | 1 | 0 | Ph-(4-OH) |
| B54 | 2-Cl | 2,5-furan | 1 | 0 | Ph-(3,4-di-OH) |
| B55 | 3-CF3 | 2,5-furan | 1 | 0 | Ph-(3,4-di-OH) |
| B56 | 4-Cl | 2,5-furan | 1 | 0 | Ph-(3,4-di-OH) |
| B57 | 4-CH2Ph | 2,5-furan | 1 | 0 | Ph |
| B58 | 4-CH2Ph | 2,5-furan | 1 | 0 | Ph-(4-OH) |
| B59 | 4-CH2Ph | 2,5-furan | 1 | 0 | Ph-(3,4-di-OH) |
| B60 | 4-Cl | 2,5-furan | 0 | 0 | H |
| B61 | 2-Cl-5-CF3 | 2,5-furan | 0 | 0 | H |
| B62 | 2,5-di-Cl | 2,5-furan | 1 | 0 | Ph-(4-OH) |
| B63 | 2-Cl-5-CF3 | 2,5-furan | 1 | 0 | Ph-(4-OH) |
| B64 | 2,5-di-Cl | 2,5-furan | 1 | 0 | Ph-(3,4-di-OH) |
| B65 | 2-Cl-5-CF3 | 2,5-furan | 1 | 0 | Ph-(3,4-di-OH) |
| B66 | 4-CH(CH3)2 | 2,5-furan | 0 | 0 | Ph |
| B67 | 4-CH(CH3)2 | 2,5-furan | 1 | 0 | Ph |
| B68 | 4-CH(CH3)2 | 2,5-furan | 1 | 0 | Ph-(3,4-di-OH) |
| B69 | 4-COPh | 2,5-furan | 0 | 0 | H |
| B70 | 4-CH(CH3)2 | 2,5-furan | 0 | 0 | H |
| B71 | 4-CH2SPh | 2,5-furan | 0 | 0 | H |
| B72 | 3-CH(CH3)2 | 2,5-furan | 0 | 0 | H |
| B73 | 4-cyclohexyl | 2,5-furan | 0 | 0 | H |
| B74 | 4-C(CH3)3 | 2,5-furan | 0 | 0 | H |
| B75 | 3-CH(CH3)2 | 2,5-furan | 1 | 0 | Ph |
| B76 | 4-CH2SPh | 2,5-furan | 1 | 0 | Ph |
| B77 | 4-CH2CH(CH3)2 | 2,5-furan | 0 | 0 | H |
| B78 | 4-CH2CH(CH3)2 | 2,5-furan | 0 | 0 | Ph |
| B79 | 4-CH2(4-Cl—Ph) | 2,5-furan | 0 | 0 | H |
| B80 | 4-C—(OH)—Ph | 2,5-furan | 0 | 0 | H |
| B81 | 4-cyclopentyl | 2,5-furan | 0 | 0 | H |
| B82 | 4-C(=CH2)—Ph | 2,5-furan | 0 | 0 | H |
| B83 | 4-dimethylbenzyl | 2,5-furan | 0 | 0 | H |
| B84 | 4-N(CH3)2 | 2,5-furan | 0 | 0 | H |
| B85 | 2,3-di-Cl | 2,5-furan | 0 | 0 | H |
| B86 | 4-N(CH3)2 | 2,5-furan | 0 | 0 | H |
| B87 | 2-CH3 | 2,5-furan | 0 | 0 | H |
| B88 | 2-OCH3 | 2,5-furan | 0 | 0 | H |
| B89 | 2-CN-3-F | 2,5-furan | 0 | 0 | Ph |

-continued

| Compound | $R^{20}$ | Het | n1 | n2 | $R^{24}$ |
|---|---|---|---|---|---|
| B90 | 2-Cl | 2,5-furan | 0 | 2 | H |
| B91 | 3-CF$_3$ | 2,5-furan | 0 | 2 | H |
| B92 | 2-CH$_3$-4-N(CH$_3$)$_2$ | 2,5-furan | 0 | 2 | H |
| B93 | 4-SO$_2$CH$_3$ | 2,5-furan | 0 | 2 | H |
| B94 | 2-Cl | 2,5-furan | 0 | 0 | CH$_3$ |
| B95 | 3-Cl | 2,5-furan | 0 | 0 | CH$_3$ |
| B96 | 4-Cl | 2,5-furan | 0 | 0 | CH$_3$ |
| B97 | 2-CH$_3$ | 2,5-furan | 0 | 0 | CH$_3$ |
| B98 | 4-F | 2,5-furan | 0 | 0 | CH$_3$ |
| B99 | 2-CF$_3$ | 2,5-furan | 0 | 0 | CH$_3$ |
| B100 | 3-CF$_3$ | 2,5-furan | 0 | 0 | CH$_3$ |
| B101 | 2-Cl | 2,5-furan | 0 | 0 | CH(CH$_3$)$_2$ |
| B102 | 3-Cl | 2,5-furan | 0 | 0 | CH(CH$_3$)$_2$ |
| B103 | 4-Cl | 2,5-furan | 0 | 0 | CH(CH$_3$)$_2$ |
| B104 | 2-CF3 | 2,5-furan | 0 | 0 | CH(CH$_3$)$_2$ |
| B105 | 3-CF$_3$ | 2,5-furan | 0 | 0 | CH(CH$_3$)$_2$ |
| B106 | 2-CH$_3$ | 2,5-furan | 0 | 0 | CH(CH$_3$)$_2$ |
| B107 | 4-F | 2,5-furan | 0 | 0 | CH(CH$_3$)$_2$ |
| B108 | 2,4-di-Cl | 2,5-furan | 0 | 0 | CH(CH$_3$)$_2$ |
| B109 | 3-Cl-4-OCH$_3$ | 2,5-furan | 0 | 0 | CH(CH$_3$)$_2$ |
| B110 | 2-NO$_2$-4-Cl | 2,5-furan | 0 | 0 | CH(CH$_3$)$_2$ |
| B111 | 3,4-di-Cl | 2,5-furan | 0 | 0 | CH(CH$_3$)$_2$ |
| B112 | 3,4-di-Cl | 2,5-furan | 0 | 0 | CH$_3$ |
| B113 | 3-Cl-4-OCH$_3$ | 2,5-furan | 0 | 0 | CH$_3$ |
| B114 | 2-NO$_2$-4-Cl | 2,5-furan | 0 | 0 | CH$_3$ |
| B115 | 4-SO$_2$NHCH$_3$ | 2,5-furan | 0 | 2 | H. |

28. A method according to claim 1 wherein the compound of formula I has the structure:

wherein the phenyl ring is optionally substituted and the cyclohexyl ring is substituted with a group corresponding to Z.

29. A method according to claim 28 wherein the compound of formula I has the structure:

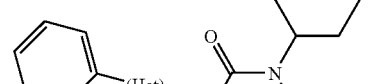

wherein $R^{20}$, Het and $R^{22}$ have the following combinations of identities:

| Compound | $R^{24}$ | Het | $R^{22}$ |
|---|---|---|---|
| C1 | 2-Cl | 2,5-furan | 3-COOH |
| C2 | 4-cyclohexyl | 2,5-furan | 3-COOH |
| C3 | 4-tert-butyl | 2,5-furan | 3-COOH |
| C4 | 4-isobutyl | 2,5-furan | 3-COOH |

-continued

| Compound | $R^{24}$ | Het | $R^{22}$ |
|---|---|---|---|
| C5 | 3-CF$_3$ | 2,5-furan | 3-COOH |
| C6 | 4-CH$_2$Ph | 2,5-furan | 3-COOH |
| C7 | 2,4-di-F | 2,5-furan | 3-COOH |
| C8 | 2,4-di-Me | 2,5-furan | 3-COOH |
| C9 | 2-Me-4-OMe | 2,5-furan | 3-COOH |
| C10 | 2-Me | 2,6-pyridine | 3-COOH |
| C11 | 2-Me-4-F | 2,5-furan | 3-COOH |
| C12 | 2-F-4-Me | 2,5-furan | 3-COOH |
| C13 | 2-OH | 2,5-furan | 3-COOH |
| C14 | 4-Me | 2,5-furan | 3-COOH |
| C15 | 4-OMe | 2,5-furan | 3-COOH |
| C16 | 2-Cl | 2,5-furan | 4-COOH |
| C17 | 3-CF$_3$ | 2,5-furan | 4-COOH |
| C18 | 4-Cl | 2,5-furan | 4-COOH |
| C19 | 2,4-di-OMe | 2,5-furan | 3-COOH |
| C20 | 2-Me-4-Cl | 2,5-furan | 3-COOH |
| C21 | 2-Cl | 2,5-furan | 4-OH |
| C22 | 4-Cl | 2,5-furan | 4-OH |
| C23 | 2,6-di-Me | 2,5-furan | 3-COOH |
| C24 | 2-Me | phenyl | 3-COOH |
| C25 | 2-OMe-4-F | 2,5-furan | 3-COOH |
| C26 | 3-F-4-OMe | 2,5-furan | 3-COOH |
| C27 | 2-OCH$_2$Ph | 2,5-furan | 3-COOH |
| C28 | 2,4,6-tri-Me | 2,5-furan | 3-COOH |
| C29 | 2-Me-4-N(Me)2 | 2,5-furan | 3-COOH |
| C30 | 2-SMe | 2,5-furan | 3-COOH |
| C31 | 2-Me | 2,5-thiophene | 3-COOH |
| C32 | 2-Cl | 2,5-thiophene | 3-COOH |
| C33 | 2-OCH$_2$(2-Cl—Ph) | phenyl | 3-COOH |
| C34 | 2-OPh | 2,5-furan | 3-COOH |
| C35 | 2-F | 2,5-thiophene | 3-COOH |
| C36 | 4-CH$_2$CH$_3$ | 2,5-furan | 3-COOH |
| C37 | 4-CF$_3$ | 2,5-furan | 3-COOH |
| C38 | 3-Ph | 2,5-furan | 3-COOH |
| C39 | 4-NHCOCH$_3$ | 2,5-furan | 3-COOH |
| C40 | 4-COCH$_3$ | 2,5-furan | 3-COOH |
| C41 | 2-F | 2,5-furan | 3-COOH |
| C42 | 3-CH$_2$OH | 2,5-furan | 3-COOH |
| C43 | 4-F | 2,5-furan | 3-COOH |
| C44 | 2-F | 2,5-furan | 4-COOH |
| C45 | 4-Me | 2,5-furan | 4-COOH |
| C46 | 2-F-4-Me | 2,5-furan | 4-COOH |
| C47 | 2-F | 2,5-thiophene | 4-COOH |
| C51 | 4-OCH$_2$CH$_3$ | 2,5-furan | 3-COOH |
| C52 | 4-OCH$_2$CH$_3$ | 2,5-furan | 4-COOH |
| C53 | 3-F-4-OMe | 2,5-furan | 4-COOH |
| C54 | 2-SMe | 2,5-furan | 4-COOH |
| C55 | 4-CF$_3$ | 2,5-furan | 4-COOH |
| C56 | 4-Cl | 2,5-furan | 3-COOH |
| C57 | 4-O(CH$_2$)$_3$CH$_3$ | 2,5-furan | 4-COOH |
| C58 | 4-SO$_2$Me | 2,5-furan | 3-COOH |
| C59 | 4-SO$_2$Me | 2,5-furan | 4-COOH |
| C60 | 2-Me | 2,5-furan | 3-COOH |
| C61 | 2-Me | 2,5-furan | 4-COOH |
| C62 | 3-SMe | 2,5-furan | 3-COOH |
| C63 | 3-SMe | 2,5-furan | 4-COOH |
| C64 | 4-SMe | 2,5-furan | 3-COOH |
| C65 | 4-SMe | 2,5-furan | 4-COOH |
| C66 | 4-OCH(CH$_3$)$_2$ | 2,5-furan | 3-COOH |
| C67 | 4-OCH(CH$_3$)$_2$ | 2,5-furan | 4-COOH |
| C68 | 3-(4-Me—Ph) | phenyl | 3-COOH |
| C69 | 3-(4-Me—Ph) | phenyl | 4-COOH |
| C70 | 2-Ph | 2,5-furan | 3-COOH |
| C71 | 2-Ph | 2,5-furan | 4-COOH |
| C72 | 4-(4-Me—Ph) | phenyl | 3-COOH |
| C73 | 4-(4-Me—Ph) | phenyl | 4-COOH |
| C74 | 2-OMe-5-Me | 2,5-furan | 3-COOH |
| C75 | 2-OMe-5-Me | 2,5-furan | 4-COOH |
| C76 | 4-NHCOCH$_3$ | 2,5-furan | 4-COOH |
| C77 | 4-(CH$_2$)$_3$CH$_3$ | 2,5-furan | 3-COOH |
| C78 | 4-(CH$_2$)$_3$CH$_3$ | 2,5-furan | 4-COOH |
| C79 | 4-(CH$_2$)$_2$CH$_3$ | 2,5-furan | 3-COOH |
| C80 | 4-(CH$_2$)$_2$CH$_3$ | 2,5-furan | 4-COOH |
| C83 | 4-SO$_2$NHMe | 2,5-furan | 3-COOH |
| C84 | 4-SO$_2$NHMe | 2,5-furan | 4-COOH |
| C85 | 4-SO$_2$N(Me)$_2$ | 2,5-furan | 3-COOH |
| C86 | 4-SO$_2$N(Me)$_2$ | 2,5-furan | 4-COOH. |

30. A method according to claim 1 wherein the compound of formula I has the structure:

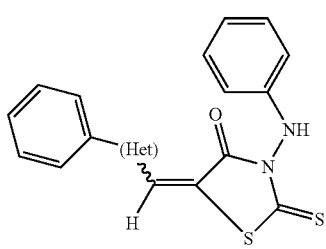

wherein the phenyl ring attached to Het is optionally substituted and the phenyl moiety of the aniline ring is substituted with a group corresponding to Z.

31. A method according to claim 30 wherein the compound of formula I has the structure:

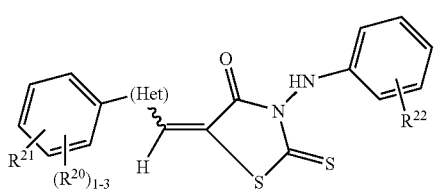

wherein $R^{20}$, $R^{21}$, Het and $R^{22}$ have the following combinations of identities:

| Compound | $R^{20}$ | $R^{21}$ | Het | $R^{22}$ |
|---|---|---|---|---|
| D1 | 2-Cl | H | 2,5-furan | 2-COOH |
| D2 | 4-tert-butyl | H | 2,5-furan | 2-COOH |
| D3 | 3-$CF_3$ | H | 2,5-furan | 2-COOH |
| D4 | 3-$NO_2$ | H | 2,5-furan | 2-COOH |
| D5 | 5-tert-butyl | 2-OH | 2,5-furan | 2-COOH |
| D6 | 4-morpholine | H | 2,5-furan | 2-COOH |
| D7 | 2,4-di-F | H | 2,5-furan | 2-COOH |
| D8 | 2,4-di-Me | H | 2,5-furan | 2-COOH |
| D9 | 2-Me | 4-OMe | 2,5-furan | 2-COOH |
| D10 | 2-Me | 4-F | 2,5-furan | 2-COOH |
| D11 | 2-F | 4-Me | 2,5-furan | 2-COOH |
| D12 | 2-OH | H | 2,5-furan | 2-COOH |
| D13 | 4-Me | H | 2,5-furan | 2-COOH |
| D14 | 4-OMe | H | 2,5-furan | 2-COOH |
| D15 | 2-Me | H | 2,6-pyridine | 2-COOH |
| D16 | 2-Cl | H | 2,5-furan | 3-COOH |
| D17 | 3-$CF_3$ | H | 2,5-furan | 3-COOH |
| D18 | 4-Cl | H | 2,5-furan | 3-COOH |
| D19 | 2,4-di-OMe | H | 2,5-furan | 2-COOH |
| D20 | 2-Cl | H | 2,5-furan | 4-COOH |
| D21 | 4-Cl | H | 2,5-furan | 4-COOH |
| D22 | 5-indolyl | H | 2,5-furan | 2-COOH |
| D23 | 2-Me | 4-Cl | 2,5-furan | 2-COOH |
| D24 | 2,6-di-Me | H | 2,5-furan | 2-COOH |
| D25 | 2-OMe | 4-F | 2,5-furan | 2-COOH |
| D26 | 3-F | 4-OMe | 2,5-furan | 2-COOH |
| D27 | 2-$OCH_2$Ph | H | 2,5-furan | 2-COOH |
| D28 | 2,4,6-tri-Me | H | 2,5-furan | 2-COOH |
| D29 | 2-Me | 4-$N(Me)_2$ | 2,5-furan | 2-COOH |
| D30 | 2-Sme | H | 2,5-furan | 2-COOH |
| D31 | 4-$N(Me)_2$ | H | 2,5-furan | 2-COOH |
| D32 | 2-$OCH_2$(2-Cl—Ph) | H | phenyl | 2-COOH |
| D33 | 2-OPh | H | 2,5-furan | 2-COOH |
| D34 | 2-Me | H | 2,5-thiophene | 2-COOH |
| D35 | 2-Cl | H | 2,5-thiophene | 2-COOH |
| D36 | 2-F | H | 2,5-thiophene | 2-COOH |
| D37 | 3-$CF_3$ | H | 2,5-furan | 4-COOH |
| D38 | 4-$CH_2CH_3$ | H | 2,5-furan | 2-COOH |
| D39 | 4-$CF_3$ | H | 2,5-furan | 2-COOH |
| D40 | 3-Ph | H | 2,5-furan | 2-COOH |
| D41 | 4-$NHCOCH_3$ | H | 2,5-furan | 2-COOH |
| D42 | 4-$COCH_3$ | H | 2,5-furan | 2-COOH |
| D43 | 2-F | H | 2,5-furan | 2-COOH |
| D44 | 3-$CH_2OH$ | H | 2,5-furan | 2-COOH |
| D45 | 4-F | H | 2,5-furan | 2-COOH |
| D48 | 4-$OCH_2$Ph | H | 2,5-furan | 2-COOH |
| D49 | 4-$O(CH_2)_3CH_3$ | H | 2,5-furan | 2-COOH |
| D50 | 4-$SO_2$Me | H | 2,5-furan | 2-COOH |
| D51 | 2-Me | H | 2,5-furan | 2-COOH |
| D52 | 3-SMe | H | 2,5-furan | 2-COOH |
| D53 | 4-SMe | H | 2,5-furan | 2-COOH |
| D54 | 4-$OCH(CH_3)_2$ | H | 2,5-furan | 2-COOH |
| D55 | 3-(4-Me—Ph) | H | phenyl | 2-COOH |
| D56 | 4-(4-Me—Ph) | H | phenyl | 2-COOH |
| D57 | 2-Ph | H | 2,5-furan | 2-COOH |
| D58 | 2-$CH_2CH_3$ | H | 2,5-furan | 2-COOH |
| D59 | 4-$(CH_2)_3CH_3$ | H | 2,5-furan | 2-COOH |
| D60 | 4-$(CH_2)_2CH_3$ | H | 2,5-furan | 2-COOH. |

32. A method according to claim 1 wherein the compound of formula I is selected from the following compounds defined in the tables 5-10, 13-18 and 20-21 in the specification: E1, E2, E3, F1, F2, F3, G1, G2, G3, G4, H1, I1, I2, J1, J2, M1, M2, M3, M4, N1, N2, N3, O1, O2, O3, O4, O5, P1, P2, Q1, Q2, Q3, Q4, Q5, Q6, Q7, Q9, R2, R3, R4, R5, R6, T1, T2, T3, T4, T5, T6, T7, T8, U1, U2, U3, U4, U5, U6, U7, U8, U9 and U10.

33. A method according to claim 1 wherein said administering comprises administering orally, by inhalation, intradermally, intramuscularly, intraperitoneally, intravenously, subcutaneously, or intranasally.

* * * * *